United States Patent
Magano et al.

(10) Patent No.: US 9,352,050 B2
(45) Date of Patent: May 31, 2016

(54) PROCESSES FOR PREPARING PEPTIDE CONJUGATES AND LINKERS

(71) Applicant: PFIZER INC., New York, NY (US)

(72) Inventors: Javier Magano, Quaker Hill, CT (US); Mark Thomas Maloney, East Lyme, CT (US); Olivier J. Marcq, Monroe, NY (US); Durgesh Vasant Nadkarni, Old Lyme, CT (US); Mark John Pozzo, Chesterfield, MO (US); John Joseph Teixeira, Jr., Mystic, CT (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/367,216

(22) PCT Filed: Dec. 10, 2012

(86) PCT No.: PCT/IB2012/057142
§ 371 (c)(1),
(2) Date: Jun. 19, 2014

(87) PCT Pub. No.: WO2013/093705
PCT Pub. Date: Jun. 27, 2013

(65) Prior Publication Data
US 2015/0031108 A1     Jan. 29, 2015

Related U.S. Application Data

(60) Provisional application No. 61/578,150, filed on Dec. 20, 2011.

(51) Int. Cl.
*A61K 47/48*     (2006.01)
*C12N 9/00*      (2006.01)
*C07D 205/08*    (2006.01)

(52) U.S. Cl.
CPC ..... *A61K 47/48507* (2013.01); *A61K 47/48246* (2013.01); *A61K 47/48415* (2013.01); *C07D 205/08* (2013.01); *C12N 9/0002* (2013.01)

(58) Field of Classification Search
None
See application file for complete search history.

(56) References Cited

U.S. PATENT DOCUMENTS 7,521,425 B2 *   4/2009   Bradshaw .................. C07K 7/02
                                                           424/1.49

FOREIGN PATENT DOCUMENTS

| EP | 0485749 A2 * | 5/1992 | ............. A61K 47/48 |
|---|---|---|---|
| WO | 2008056346 A2 | 5/2008 | |
| WO | 2008081418 A1 | 7/2008 | |
| WO | 2009136352 A1 | 11/2009 | |

OTHER PUBLICATIONS

Adamczyk et al. An Easy Preparation of Hapten Active Esters via Solid Supported EDAC. Terrahedron Lerrers, vol. 36. No. 46. pp. 83458346, 1995.*
Almiento, G., et al., "Stereoselective synthesis and conformational analysis of unnatural tetrapeptides. Part 2," Tetrahedron: Asymmetry, 2007, 2695-2711, vol. 18.
Boger, D., et al., "Total Synthesis of L,L-Isodityrosine and Isodityrosine-Derived Agents: K-13, OF4949-III, an dOF4949-IV," The Journal of Organic Chemistry, 1990, 6000-6017, vol. 55.
Cainelli, G., et al., "4-Alkylidene-azetidin-2-ones: Novel Inhibitors of Leukocyte Elastase and Gelatinase," Bioorganic & Medicinal Chemistry, 2003, 5391-5399, vol. 11.
Cainelli, G., et al., "N-Acylation of 4-alkylidene-B-lactams: unexpected results," Tetrahedron Letters, 2003, 6269-6272, vol. 44.
Clark, J., et al., "The Derivatization of Bioplatfornn Molecules by using KF/Alumina Catalysis," ChemSusChem, 2009, 1025-1027, vol. 2.
Feledziak, M., et al., "B-Lactams Derived from a Carbapenem Chiron Are Selective Inhibitors of Human Fatty Acid Amide Hydrolase versus Human Monoacylglycerol Lipase," Journal of Medicinal Chemistry, 2009, 7054-7068, vol. 52.
Firestone, R., et al., "Monocyclic B-Lactam Inhibitors of Human Leukocyte Elastase," Tetrahedron, 1990, 2255-2262, vol. 46, No. 7.
Huang, H., et al., "Specifically Targeting Angiopoietin-2 Inhibits Angiogenesis, Tie2-Expressing Monocyte Infiltration, and Tumor Growth," Clinical Cancer Research, 2011, 1001-1012, vol. 17, No. 5.
International Preliminary Report on Patentability for International Application No. PCT/IB2012/057142 issued on Jun. 24, 2014.
International Search Report for International Application No. PCT/IB2012/057142 completed on Jun. 13, 2013.
Journet, M., et al., "Semisynthesis of an Antifungal Lipopeptide Echinocandin," The Journal of Organic Chemistry, 1999, 2411-2417, vol. 64.

(Continued)

*Primary Examiner* — Karlheinz R Skowronek
*Assistant Examiner* — Jia-Hai Lee
(74) *Attorney, Agent, or Firm* — Pfizer Inc.

(57) ABSTRACT

The present invention provides a process for preparing a compound of Formula 5b, as well as intermediates thereof, and novel classes of compounds useful in process for preparing these and similar compounds.

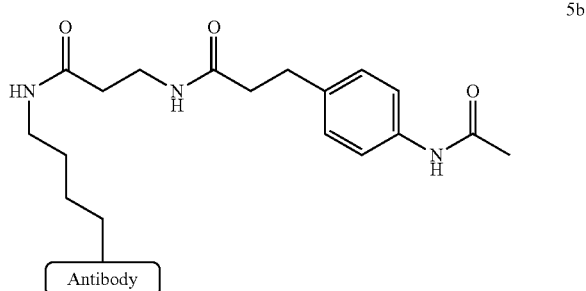

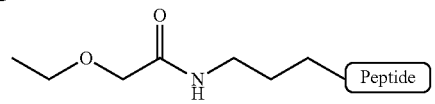

27 Claims, No Drawings

(56) References Cited

OTHER PUBLICATIONS

Llanes Garcia, A., et al., "T3P: A Convenient and Useful Reagent in Organic Synthesis," Synlett, 2007, 1328-1329, No. 8.

Menger, F., et al., "Synthesis and Reactivity of 5-Fluorouracil/Cytarabine Mutual Prodrugs," The Journal of Organic Chemistry, 1997, 9083-9088, vol. 62.

Palanki, M., et al., Development of a long acting human growth hormone analog suitable for once a week dosing, Bioorganic & Medicinal Chemistry Letters, 2013, 402-406, vol. 23.

Rohman, M., et al., "KF-alumina-mediated Bargellini reaction," Tetrahedron Letters, 2010, 4772-4775, vol. 51.

Schneider, J., et al., "Synthesis and Efficacy of Square Planar Copper Complexes Designed to Nucleate B-Sheet Structure," Journal of the American Chemical Society, 1995, 2533-2546, vol. 117.

Shin, I., et al., "Chemoselective ligation of maleimidosugars to peptides/protein for the preparation of neoglycopeptides/neoglycoprotein," Tetrahedron Letters, 2001, 1325-1328, vol. 42.

Staub, I., et al., "B-Lactams as Selective Chemical Probes for the in Vivo Labeling of Bacterial Enzymes Involved in Cell Wall Biosynthesis, Antibiotic Resistance, and Virulence," Journal of the American Chemical Society, 2008, 13400-13409, vol. 130.

Urbach, A., et al., "Large ring 1,3-bridged 2-azetidinones: Experimental and theoretical studies," European Journal of Medicinal Chemistry, 2009, 2071-2080, vol. 44.

Urbach, A., et al., "Novel Large-Ring 1,3-Bridged 2-Azetidinones as Potential Inhibitors of Penicillin-Binding Proteins," European Journal of Organic Chemistry, 2009, 1757-1770, vol. 2009, No. 11.

Van Alsten, J., (Nov. 8, 2010), "Monitoring Reaction Chemistry and Analysis of Reaction Kinetics in Solid Phase Peptide Synthesis," Abstract of Paper Presented at the 2010 Annual Meeting of the American Institute of Chemical Engineers: Food, Pharmaceutical & Bioengineering Division, Salt Lake City, UT.

Written Opinion of the International Searching Authority for International Application No. PCT/IB2012/057142 mailed on Jun. 21, 2013.

Youcef, R., et al., "Stereoselective Synthesis of Dienic Nitrogen Compounds," Synthesis, 2006, 0633-0636, vol. 2006, No. 4.

* cited by examiner

PROCESSES FOR PREPARING PEPTIDE CONJUGATES AND LINKERS

This application is a §371 filing of PCT/IB2012/057142 filed Dec. 10, 2012, which claims the benefit of priority to U.S. Provisional Application No. 61/578,150 filed Dec. 20, 2011; the entire contents of which are incorporated herein by reference.

REFERENCE TO SEQUENCE LISTING

This application is being filed electronically via EFS-Web and includes an electronically submitted sequence listing in .txt format. The .txt file contains a sequence listing entitled "PC71863A_SequenceListing_ST25.txt" created on Jun. 19, 2014, and having a size of 22KB. The sequence listing contained in this .txt file is part of the specification and is herein incorporated by reference in its entirety.

The present invention relates to novel processes, compounds and intermediates useful in the preparation of certain antibody-linker-peptide conjugates.

BACKGROUND

Covalent conjugation of biochemical molecules can be employed to bring together two or more molecules to form a bioconjugate that displays the combined properties of each of the individual components. This technique has been used to increase plasma half-life and decrease immunogenicity of therapeutic agents, such as peptides. Typically, the therapeutic agent is conjugated to a macromolecular carrier directly or via a linker. Common macromolecular carriers include antibodies, albumin and synthetic polymers.

U.S. Pat. Nos. 7,521,425 and 8,288,349 describe processes for preparing compounds useful as linkers.

The reference to any art in this specification is not, and should not be taken as, an acknowledgement of any form or suggestion that the referenced art forms part of the common general knowledge.

Background of Conjugation Process

Antibody-drug conjugate 5 has been described in U.S. Pat. No. 8,288,349 (whose contents are hereby incorporated entirely), the production of which involves several stages. Initially, the peptide 2 and the linker 1 are prepared separately. The peptide 2 is then conjugated to the linker 1 to form the linker-peptide complex (3). After purification, the conjugated linker-peptide complex 3 is combined with the antibody (4) so as to allow the azetidinone moiety of 3 form a covalent bond with the antibody 4, thereby resulting in an assembled peptide-linker-antibody complex; the antibody-drug conjugate 5 (scheme I). The linker peptide complex is prepared by a lengthy multi-step process requiring generation of the linker 1, 8 and conjugation to the peptide 2 (scheme II).

Scheme (I) Preparation of peptide-linker-antibody bioconjugate 5.

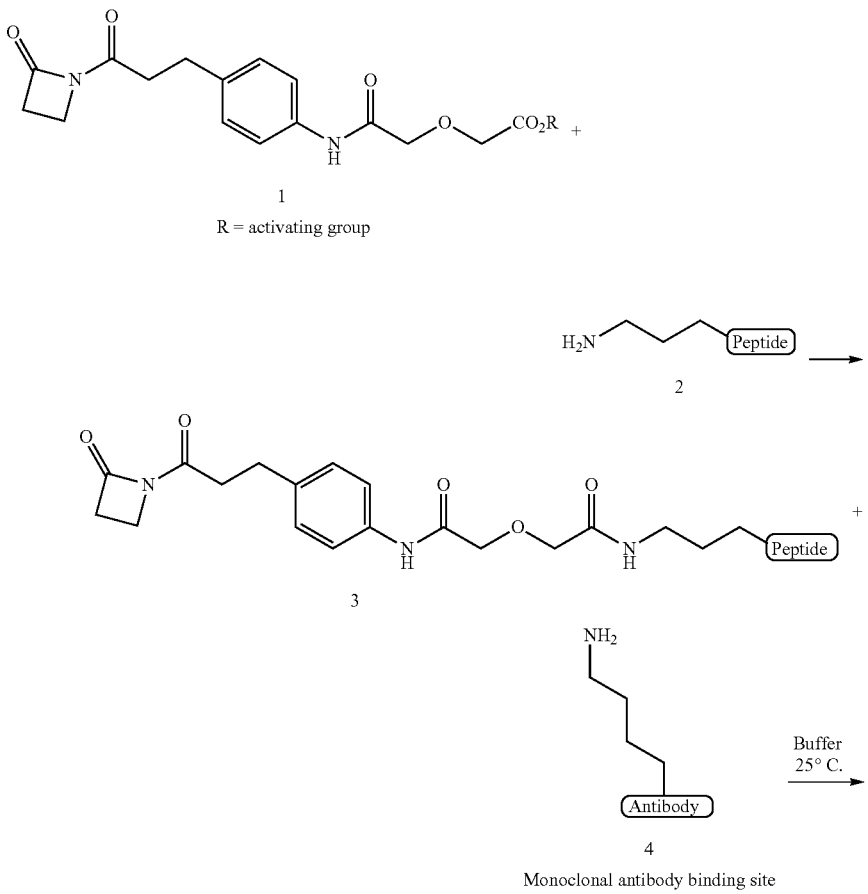

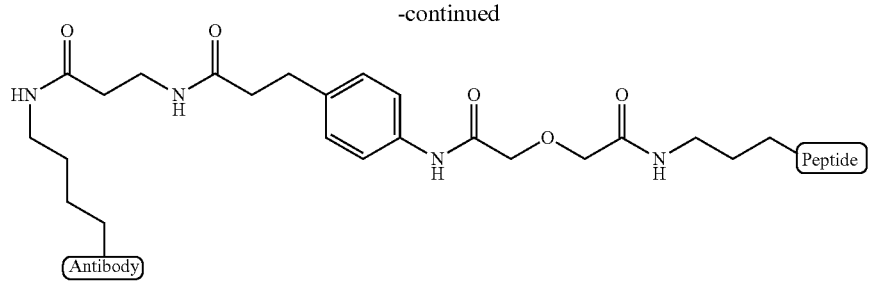

5
Peptide-linker-antibody bioconjugate

The peptide is shown schematically, with the available lysine side-chain indicated. The lysine residue forming the covalent bond with the linker is preferably the only unmodified lysine in the peptide, to avoid multiple species forming. The lysine may be located as the N-terminal residue, the C-terminal residue, or anywhere within the peptide chain (for example SEQ ID NOs:1 and 2). The antibody is also shown schematically, with the reactive side chain indicated. Typically, the antibody is a catalytic antibody such as an aldolase catalytic antibody comprising a reactive lysine in the antibody combining site (antigen recognition site, or CDR), as further described herein and also in U.S. Pat. Nos. 7,521,425, 8,288, 349, and 8,252,902.

Scheme (II) Preparation of peptide-linker 3.

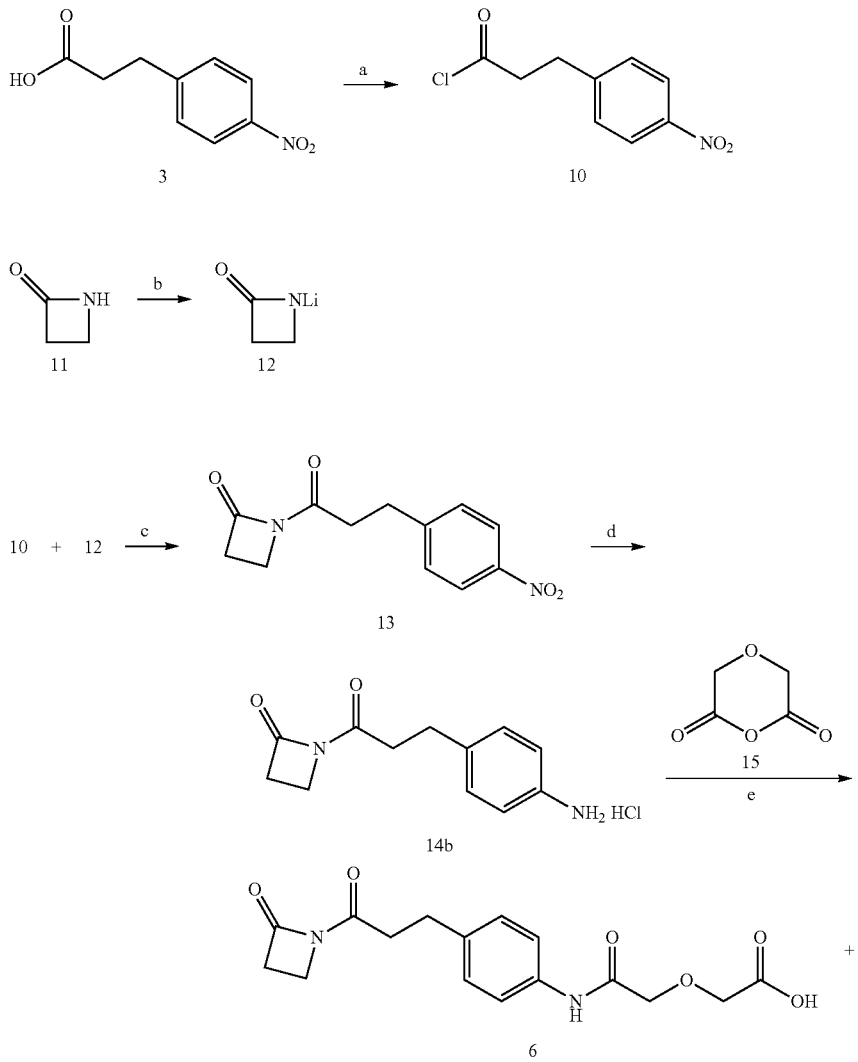

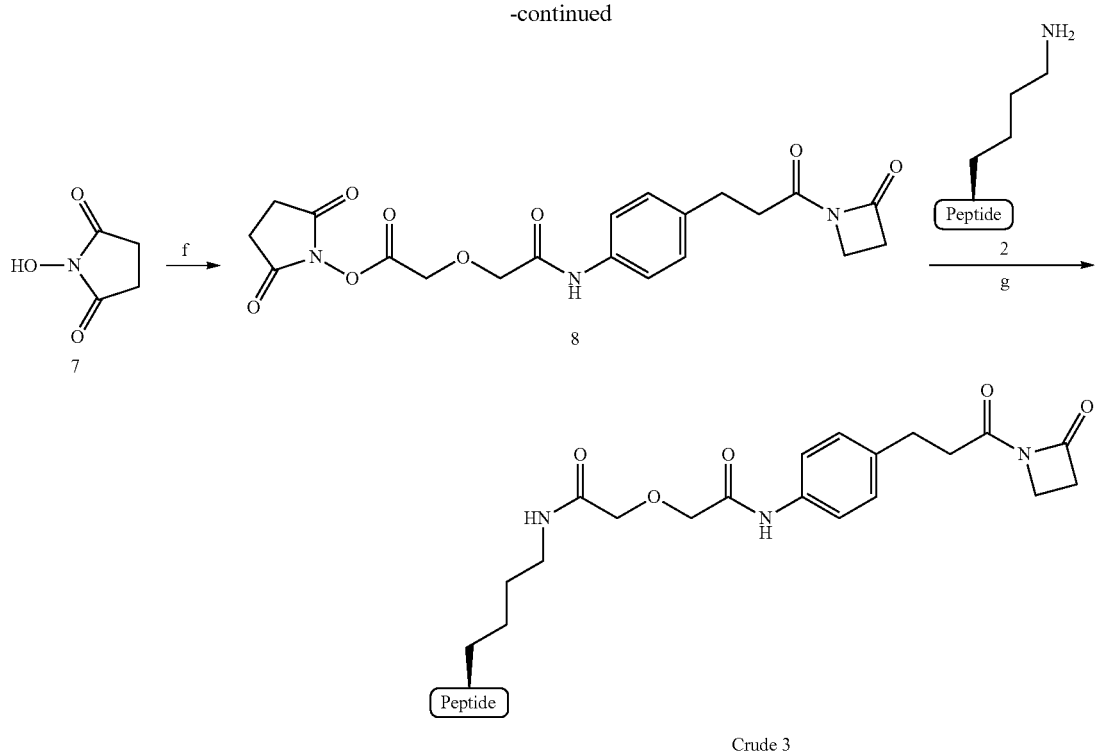

(a) Cl₂SO, reflux.
(b) n-BuLi, -70° C., THF.
(c) 0° C., 91%.
(d) H₂, 10% Pd/C, MeOH, HCl, 40° C., 68%.
(e) DIPEA, CH₂Cl₂, rt, 83%.
(f) DIC, THF, 0° C. to rt, 18 h, 100%.
(g) NMM, DMF, 0-5° C., 10 min.

Synthesis of Acid Linker 6

The original synthesis of acid 6 is shown in scheme II. Acid 9 is treated with Cl₂SO at reflux to provide crude acid chloride 10. In a separate flask, 2-azetidinone 11 is deprotonated at cryogenic temperature with n-BuLi in THF to generate Li anion 12 which, without isolation, is reacted with acid chloride 10 to give intermediate 13 in 91% yield. The nitro group on 13 is then reduced using catalytic hydrogenation with 10% Pd/C in MeOH to give aniline HCl salt 14b in 68% yield. The last step involves the reaction between 14b and diglycolic anhydride (15) in CH₂Cl₂ in the presence of DIPEA to provide acid 6 in 83% yield.

During preliminary experiments to determine the scalability of scheme II, it was found that the yield for the coupling between acid chloride 10 and azetidinone 11 was not reproducible and dropped to about 40-55% when the reaction was run on about 200-g scale. There therefore exists a need to find an alternative mechanism to generate acid 6 with the additional goal of avoiding running the process at cryogenic temperature.

Synthesis of Peptide-Linker 3

Acid 6 and N-hydroxysuccinimide (7) undergo reaction with N,N'-diisopropylcarbodiimide (DIC) as coupling reagent to afford N-hydroxysuccinimido ester 8 in quantitative yield after urea byproduct filtration and trituration in petroleum ether (scheme 2, reaction f). Crude 8 is immediately used in the subsequent reaction with peptide 2 with N-methylmorpholine (NMM) as base in DMF to provide conjugate 3 in a process that takes about 2 days. The isolation of crude 3 from the reaction mixture involves neutralization to pH=6.0 with acetic acid, removal of DMF under vacuum, and dissolution of the resulting residue in 0.1 M ammonium acetate buffer.

Crude 3 is then subjected to chromatographic purification (0.1 M NaClO₄/MeCN buffer). The fractions with low purity (<60%) are discarded and the fractions in the 60-95% purity range re-chromatographed (0.1% TFA water/MeCN buffer). The fractions in the 80-95% purity range are re-chromatographed under the same conditions and the fractions with purity below 80% discarded. The fractions with >96% purity and no single impurity above 1.5% are pooled and lyophilized to give clean 3 in 40.4% yield (molar basis). This chromatographic purification of 3 takes about 2 days. The lyophilized fractions are then reconstituted (in other words, a full redissolution of the solid in an appropriate solvent), in a 1:1 CH₃CN/H₂O mixture to generate a homogeneous lot of intermediate 3, in a process that takes about 2 days.

After filtration of some insoluble material, the filtrates are subjected to a second lyophilization to generate 3 in about 11.9% yield, in a process that takes about 2 days. While this lengthy and energy- and solvent-intensive process is quite suitable for the generation of small batches of material (~50 g), its implementation in the manufacture of larger quantities of 3 is relatively impractical due to the very low throughput, high scale-up costs, and lengthy process time of about 10 days. There therefore exists a need to develop a process to generate large amounts of peptide-linker conjugate 3, capable of producing multi-hundred gram quantities under cGMP conditions in a time- and cost-effective manner.

SUMMARY OF THE INVENTION

The present invention provides an improved process for the preparation of peptide-linker antibody conjugate according to formula 5a:

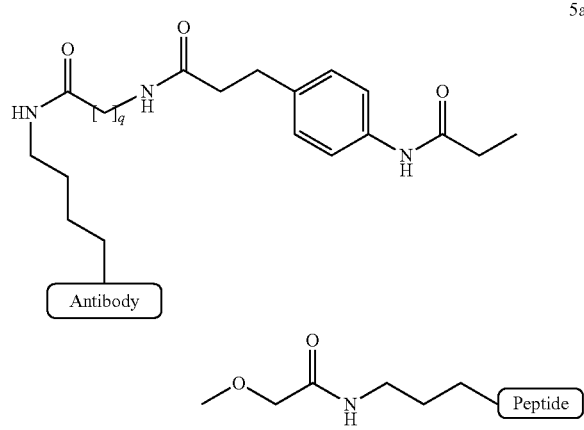

5a comprising
(i) reacting 9a and 11 together in the presence of 1-propanephosphonic acid anhydride (T3P) to create compound 13a Scheme IIIa

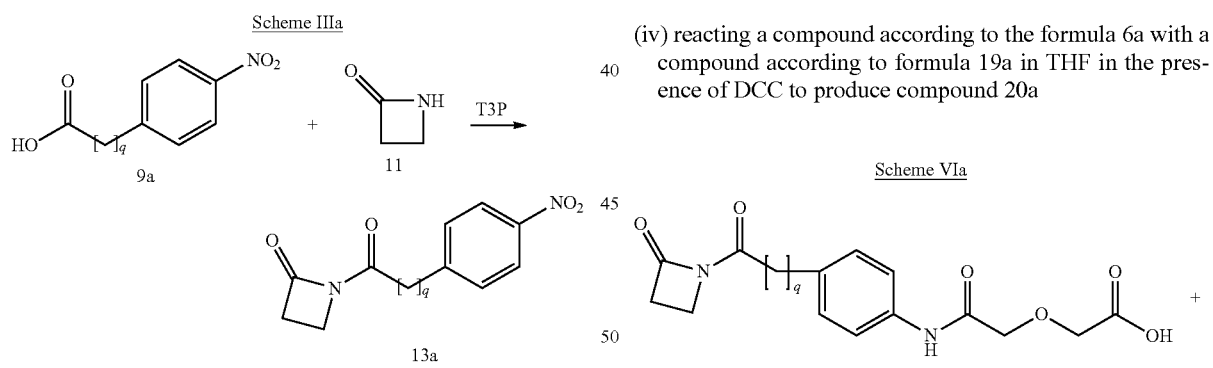

(ii) catalytic hydrogenation with Pd/C of compound 13a in a THF:H$_2$O solution of at least about 50% THF to produce a compound of formula 14a Scheme IVa

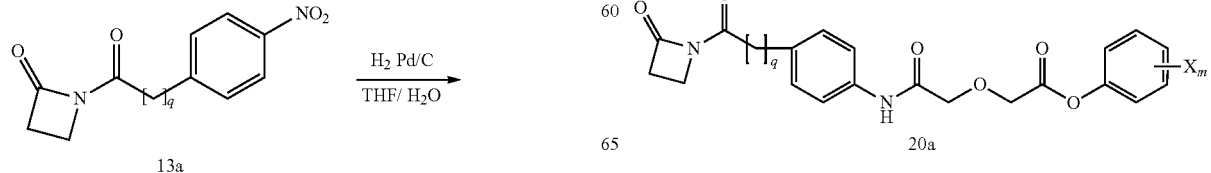

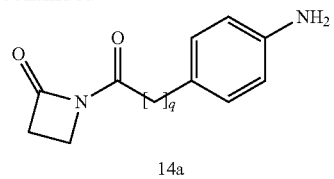

14a (iii) combining a solution of 14a in THF with a compound according to formula 15 in a reaction substantially free of base to produce compound 6a Scheme Va

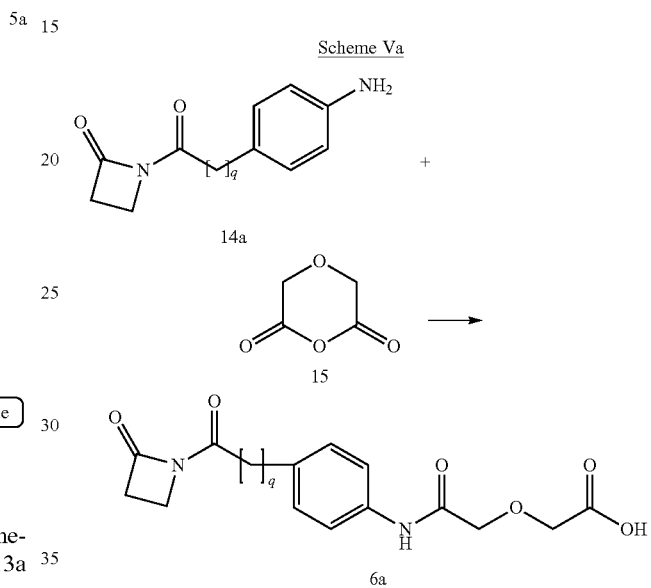

(iv) reacting a compound according to the formula 6a with a compound according to formula 19a in THF in the presence of DCC to produce compound 20a Scheme VIa (v) combining 20a with a ε-amino containing peptide 2 dissolved in an aprotic polar [15th] solvent to produce bioconjugate 3a The present invention further provides an improved process for the preparation of peptide-linker according to formula 3a

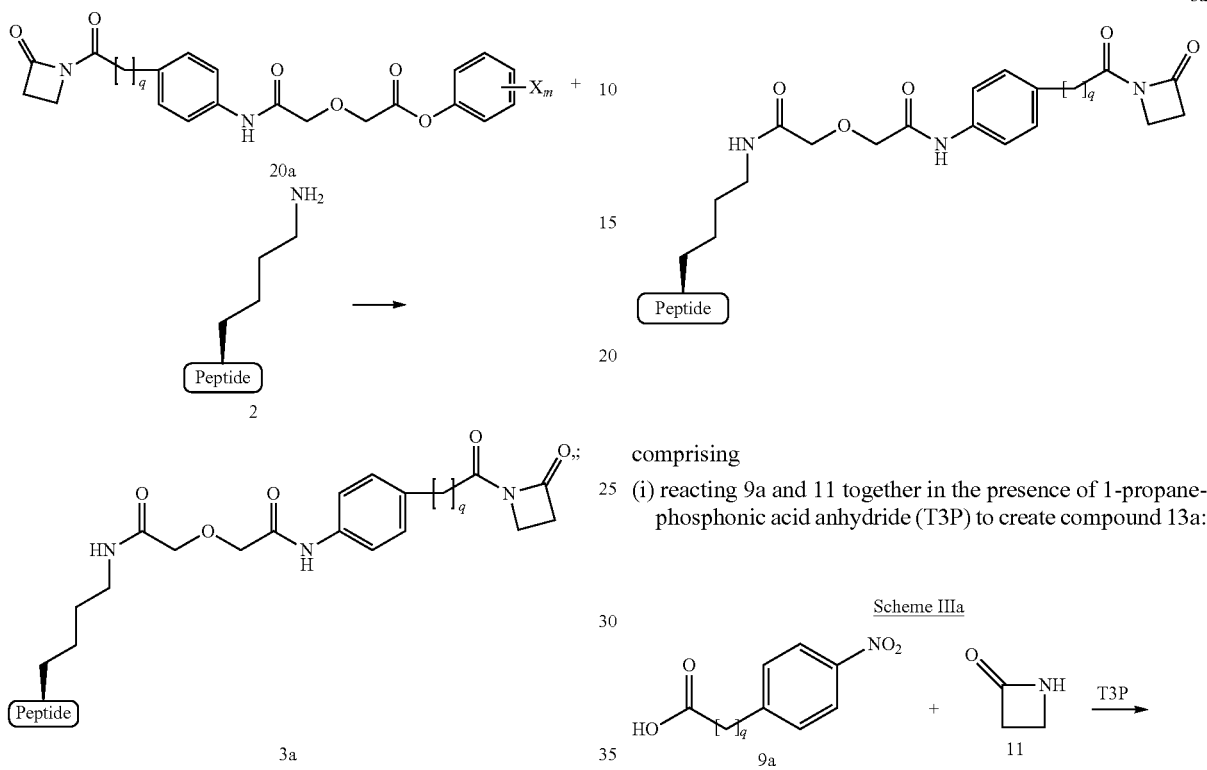

comprising (i) reacting 9a and 11 together in the presence of 1-propane-phosphonic acid anhydride (T3P) to create compound 13a:

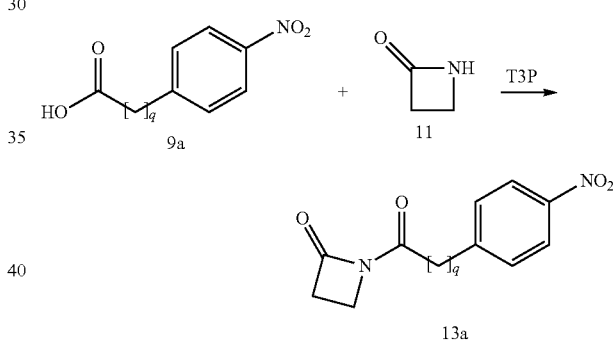

(vi) dissolving compound 3a in DMSO:
(vii) adding histidine buffer at pH between about 5.5 to about 7.5 to the solution of DMSO and 3a of step (vi);
(viii) Adding an antibody comprising comprises a variable light region comprising SEQ ID NO:5 and a variable heavy region comprising SEQ ID NO:6 to the solution of step (vii), so as to have a peptide:antibody molar ratio of between about 1.8:1 to about 3:1;
(ix) Agitating the mixture formed in step (viii) at a medium speed so as to avoid foaming the reaction mixture for at least about 1 hr at between about pH 5.5 and about pH7.5 and at a temperature of between about 5° C. and 35° C.;
(x) Filtration of the solution from (ix) to extract the resultant peptide-linker antibody conjugate 5a.

(ii) catalytic hydrogenation with Pd/C of compound 13a in a THF:H$_2$O solution of at least about 50% THF to produce a compound of formula 14a

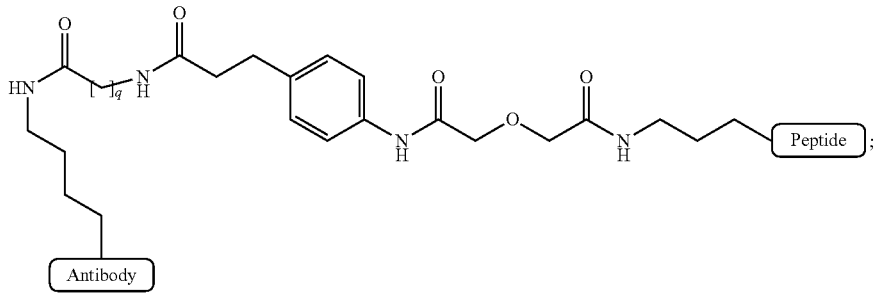

wherein q=1, 2, 3, 4, or 5, X=F or Cl, m=3, 4, or 5.

Scheme IVa

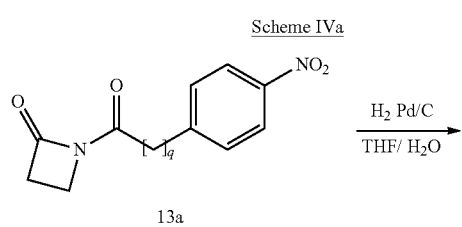

13a

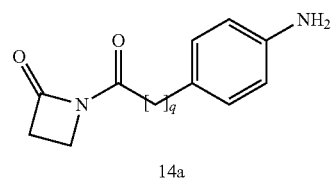

14a (iii) combining a solution of 14a in THF with a compound according to formula 15 in a reaction substantially free of base to produce compound 6a Scheme Va

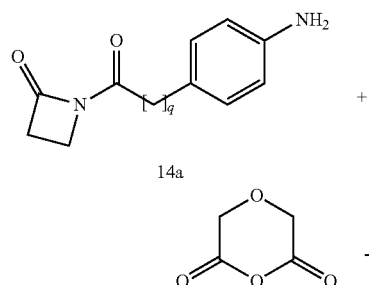

14a

+

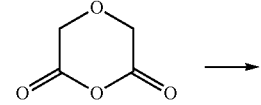

15

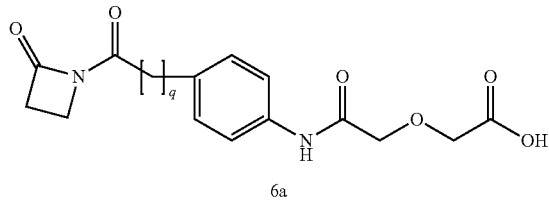

6a (iv) reacting compound 6a with a compound according to formula 19a in THF in the presence of DCC to produce compound 20a Scheme VIa

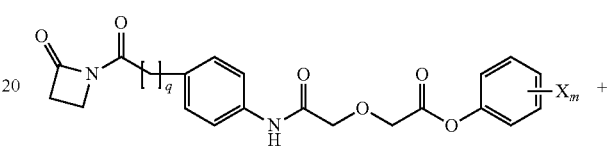

20a (v) optionally crystallizing compound 20a;
(vi) combining 20a with a ε-amino containing peptide 2 dissolved in an aprotic polar 15th solvent to produce peptide-linker 3a Scheme VIIa

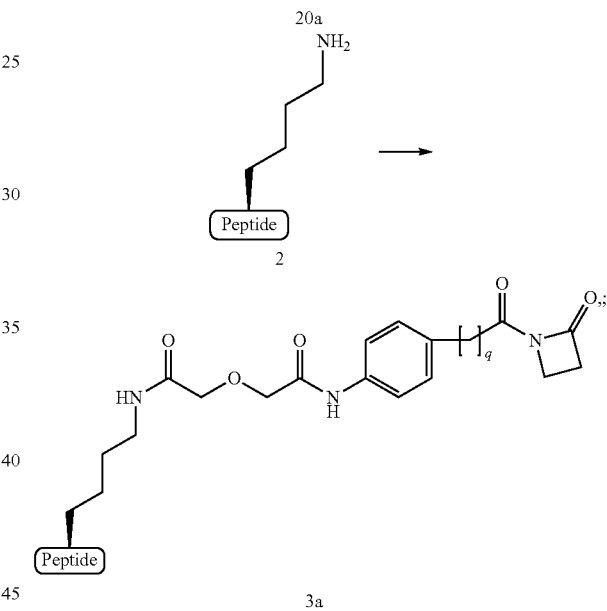

3a (vii) optionally precipitating peptide-linker 3a by adding a DMF solution of 3a to MeCN;
wherein q=1, 2, 3, 4, or 5, X=F or Cl, and m=3, 4, or 5.

In some aspects of the invention, the improved process provides a reduction in cost based on the improved yield, with an increase in the yield of peptide-linker conjugate 3a from starting peptide 2 from about 30% to about 85%. There are other components such as energy savings and solvent savings, which are also significant, but likely have a smaller economic impact. In particular, the elimination of 2 chromatographies in the improved process results in a solvent savings estimated at 1500-2000 liters/kg product. The reduction in solvent also provides energy savings since elution solvent does not have to be removed via distillation. Significant energy saving are also associated with elimination of 2 lyophilization steps in the improved process.

In some aspects of the invention, the improved process provides a reduction in cycle time by avoiding chromatography and lyophilization after the synthesis of the peptide-linker conjugate 3a. For the cycle time, the new process delivers material in about 2 days, compared with the existing cycle time of about 10 days. Therefore, the new process delivers a reduction in cycle time of 80% or greater.

In some aspects of the invention, the peptide 2 comprises the specific sequence of SEQ ID NO:1, wherein AcK is acyl lysine, to form peptide 2a. SEQ ID NO:1: C(O)CH$_3$-Q(AcK)YQPLDE(AcK)DKTLYDQFMLQQG-NH$_2$ 2a

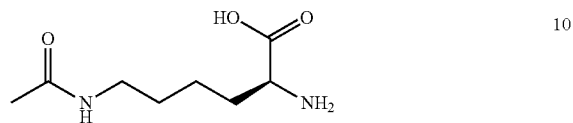

Acyl lysine

In some aspects of the invention, the peptide-linker conjugate 3b comprises the formula:

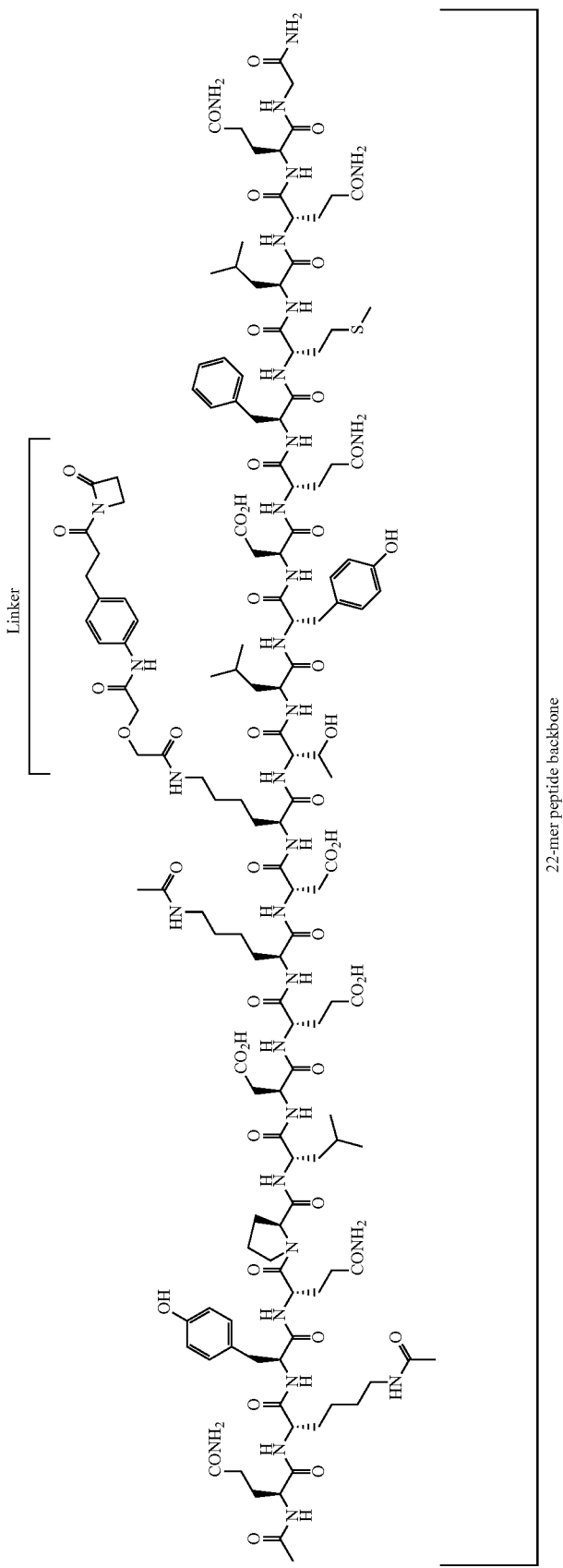

It will be appreciated that other peptides and non-peptidic agents may usefully be conjugated to the linkers of the invention.

The present invention provides an optimized and scalable process to manufacture peptide-linker conjugate 3a that avoids the chromatographic purification and lyophilization that is typically required for the isolation of this type of compound and results in significantly higher yields.

The invention provides an operationally simple protocol that couples the peptide to the linker in DMF, optionally followed by precipitation with MeCN as anti-solvent and filtration to give material that meets specifications for use in clinical batches. A scalable synthesis of the linker is also described which features the N-acylation of 2-azetidinone 11 promoted by 1-propanephosphonic acid anhydride (T3P) under mild conditions in the first step. This new protocol provides reproducible yields, does not resort to chromatographic purification, and avoids both the need for performing the reaction at cryogenic temperatures and the use of n-BuLi as was required in the original route.

The number of operations during the second step of the synthesis (13a reduction to 14a) has been simplified by telescoping compound 14a into the next step (reaction with diglycolic anhydride to form acid 6a), thus avoiding an additional isolation.

Furthermore, an efficient activation method for acid 6a has been developed by means of the corresponding ester of formula 20a, which display an excellent balance between stability for isolation purposes and reactivity during the conjugation with peptide 2.

The present invention further provides an improved and efficient conjugation protocol for the coupling of a linker and a peptide as part of a program to manufacture a peptide-linker-antibody bioconjugate for the treatment of cancer. This novel approach allows for the isolation of peptide-linker conjugate 3a via direct precipitation from a MeCN/DMF mixture followed by filtration. The resource-intensive isolation protocol performed originally, and common to this class of compounds, involving extensive chromatographic purification and lyophilization has thus been avoided. One of the major improvements is the dramatic increase in yield for this step, which has gone up from 12% to 83%. Further advantages are the reduction in solvent and energy consumption, which substantially lowers the cost per gram and turns the process into a greener alternative. An extensive screen of all the key parameters resulted in reaction conditions that provided material of satisfactory quality to meet stringent specifications in terms of purity and residual solvent content. This method represents an innovative approach toward the isolation of this type of material that departs from the traditional chromatographic purification.

The present invention also provides an optimized route to the activated linker that eliminates cryogenic conditions and the use of n-BuLi, avoids the isolation of one of the intermediates through telescoping, and further provides a novel pentafluorophenol ester as a suitable substrate with the desired balance between stability for isolation purposes and reactivity in the final conjugation step with the peptide therapeutic agent.

All these improvements have translated into the manufacture of significant quantities of peptide-linker conjugate 3a under cGMP conditions.

In some aspects, the invention provides for a new process for preparing compound 13a, comprising reacting 9a and 11 together in the presence of 1-propanephosphonic acid anhydride (T3P) to create compound 13a Scheme IIIa

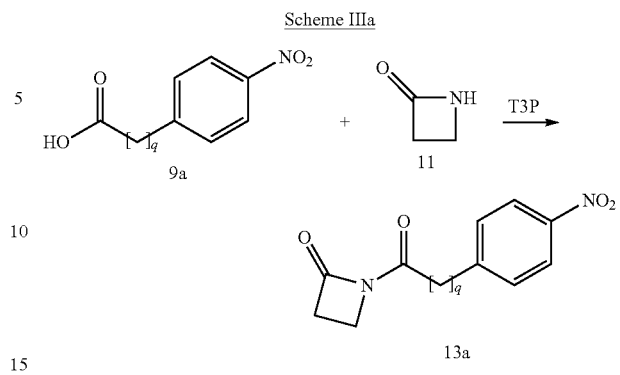

wherein q is 1, 2, 3, 4, or 5. Where q is 2, the reaction may comprise 9 and 11 in the presence of T3P to produce 13:

Scheme III

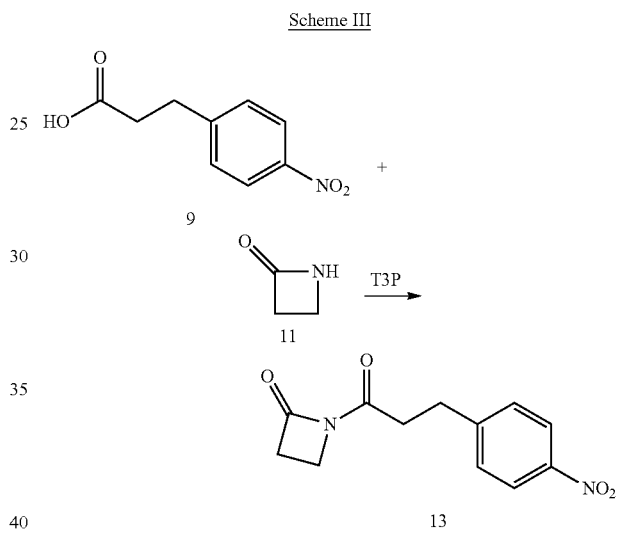

The improved process of the invention provides significant advantages over the original process, as 2-azetidinone 11 is typically quite unreactive toward amide bond formation. In addition, this improved process is reproducible at least on several hundred gram-scale. In some aspects, the invention provides a compound prepared according to such a process.

The reaction may be carried out in a $1^{st}$ solvent selected from the group consisting of tetrahydrofuran (THF), 2-methyltetrahydrofuran, NMP, N,N-dimethylformamide (DMF), N,N-dimethylacetamide (DMAc), 1-methyl-2-pyrrolidinone, ethyl acetate (EtOAc), and acetonitrile (MeCN). Particularly suitable $1^{st}$ solvents include DMF, EtOAc, and MeCN. In some aspects, the $1^{st}$ solvent is selected between EtOAc and MeCN. In some aspects, the $1^{st}$ solvent is DMF. In some aspects, the $1^{st}$ solvent may be MeCN.

In some aspects, the reaction is carried out in the presence of a $1^{st}$ base. The $1^{st}$ base may be selected from the group consisting of trimethylamine, triethylamine, tributylamine, DIPEA, pyridine, DBU, DABCO, 2,3-lutidine, 2,4-lutidine, 2,5-lutidine, 2,6-lutidine, 3,4-lutidine, 3,5-lutidine. Particularly suitable $1^{st}$ bases include DIPEA, triethylamine and pyridine. In some aspects, the $1^{st}$ base is DIPEA.

The $1^{st}$ base may be present in an amount relative to acid 9a in a range whose lower limit is selected from the group consisting of about 0.5, 1, 1.5, 2, 2.5, 3, 3.5, 4, 4.5, and 5; and whose upper limit is selected from the group consisting of about 2.5, 3, 3.5, 4, 4.5, 5, 6, 7, 8, 9 and 10. In some aspects, the 1$^{st}$ base is present in an amount between about 1 and about 10 equivalents of acid 9. In some aspects, the 1$^{st}$ base is present in an amount between about 2 and about 5 equivalents of acid 9a. In some aspects, the 1$^{st}$ base is present in an amount between about 2 and about 4 equivalents of acid 9a. In some aspects, the 1$^{st}$ base is present in an amount between about 2.5 and about 3.5 equivalents of acid 9a. In some aspects, the 1$^{st}$ base is present in an amount of about 3 equivalents of acid 9a. In some aspects, the 1$^{st}$ base is DIPEA and is present in an amount of about 3 equivalents of acid 9a.

The 2-azetidinone 11 may be present in an amount relative to acid 9a in a range whose lower limit is selected from the group consisting of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, and 5; and whose upper limit is selected from the group consisting of about 1.3, 1.4, 1.5, 1.6, 1.7, 1.8, 1.9, 2, 2.5, 3, 3.5, 4, 4.5, 5, 6, 7, 8, 9 and 10. In some aspects, the 2-azetidinone 11 is present in an amount between about 0.1 and about 10 equivalents of acid 9a. In some aspects, the 2-azetidinone 11 is present in an amount between about 0.5 and about 3 equivalents of acid 9a. In some aspects, the 2-azetidinone 11 is present in an amount between about 0.5 and about 5 equivalents of acid 9a. In some aspects, the 2-azetidinone 11 is present in an amount between about 0.5 and about 1.5 equivalents of acid 9a. In some aspects, the 2-azetidinone 11 is present in an amount between about 1.0 and about 1.5 equivalents of acid 9a. In some aspects, the 2-azetidinone 11 is present in an amount of about 1.2 equivalents of acid 9a.

The T3P may be present in an amount relative to acid 9a in a range whose lower limit is selected from the group consisting of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, and 5; and whose upper limit is selected from the group consisting of about 1.3, 1.4, 1.5, 1.6, 1.7, 1.8, 1.9, 2, 2.5, 3, 3.5, 4, 4.5, 5, 6, 7, 8, 9 and 10. In some aspects, the T3P is present in an amount between about 0.1 and about 10 equivalents of acid 9a. In some aspects, the T3P is present in an amount between about 0.5 and about 3 equivalents of acid 9a. In some aspects, the T3P is present in an amount between about 0.5 and about 5 equivalents of acid 9a. In some aspects, the T3P is present in an amount between about 0.5 and about 1.5 equivalents of acid 9a. In some aspects, the T3P is present in an amount between about 1.0 and about 1.5 equivalents of acid 9a. In some aspects, the T3P is present in an amount of about 1.3 equivalents of acid 9a.

In some aspects, the T3P may be provided in a 2$^{nd}$ solvent selected from the group consisting of EtOAc N,N-dimethylformamide and butyl acetate. In some aspects, the T3P may be present in an amount between 1% and 99% in the solution, provided that molar ratio between T3P and substrate is kept between about 0.1:1 and about 10:1. The T3P may be provided in the second solvent in a range whose lower limit is selected from the group consisting of about 1%, about 5%, about 10%, about 15%, about 20%, about 25%, about 30%, about 35%, about 40% about 45% and about 50%; and whose upper limit is selected from the group consisting of about 50%, about 55%, about 60%, about 65%, about 70%, about 75%, about 80%, about 85%, about 90%, about 95% and about 99%. In some aspects, the T3P is provided in an about 50% solvent solution. The T3P may be provided in an about 50% EtOAc solution.

Accordingly, in some aspects, the addition of T3P to a mixture of compounds 9a and 11 in DMF and pyridine as base gave desired product in about 20% to about 45% yield. In some aspects, the ratio of reaction constituents is about 3 equiv of DIPEA, about 1.2 equiv of 11 and about 1.2 equiv of T3P (in about 50% EtOAc) in MeCN to about 1 equivalent of acid 9a. The advantage of these proportions is to provide consistent yields of at least about 20%. In some aspects, this combination yields at least about 25%. In some aspects, this combination yields at least about 30%. In some aspects, this combination yields at least about 35%. In some aspects, this combination yields at least about 40%. In some aspects, these proportions provide about 40% yield.

In some aspects, about 5 equivalents of DIPEA, about 1.5 equiv of 11 and about 1.5 equiv of T3P are used, in MeCN. The advantage of these proportions is to provide consistent yields of about 55-60%, in particular when the reaction was performed at RT (i.e. about 15° C. to about 25° C., preferably 18° C. to about 22° C., and most preferably about 20° C.) for about 2 h.

Some of the advantages of this method are the operational simplicity (slow addition of a 50% T3P solution in EtOAc to a mixture containing the 2 coupling partners and base in MeCN), mild reaction conditions, and yield reproducibility.

In some aspects, the reaction may be performed at RT (e.g. about 20° C.) for about 18 hr. In some aspects, the temperature of the reaction may be operated at a range whose lowest value is selected from the group consisting of about 0, 1, 2, 3, 4, 5, 6, 7, 8, 9, 10, 12, 15, 16, 17, 18, 19, 20, 21, 22, 23, 24, 25, 26, 27, 28, 29, and 30° C., and whose upper value is selected from the group consisting of about 25, 26, 27, 28, 29, 30, 32, 35, 36, 37, 40, 45, and 50° C. In some aspects, the temperature range is between about 0° C. and about 50° C. In some aspects, the temperature range is between about 10° C. and about 30° C. In some aspects, the temperature is room temperature. In some aspects, the temperature is 20° C.

Upon reaction completion the MeCN may be removed under vacuum and the residue redissolved in a 3$^{rd}$ solvent comprising a $C_1$-$C_4$ alkyl acetate. The $C_1$-$C_4$ alkyl acetate may be selected from the group consisting of i-propyl acetate, methyl acetate, ethyl acetate, n-propyl acetate, and n-butyl acetate. In some aspects, the residue may be redissolved in i-propyl acetate The organic phase may then be washed with aqueous citric acid (other acids, such as acetic acid may also be used), and, after a solvent switch from the 3$^{rd}$ solvent to a 4$^{th}$ solvent selected from the group consisting of 2-propanol, 1-propanol, 1-butanol, 2-butanol, and tert-butanol, intermediate 13a precipitates from solution in high purity (>98%). In some aspects, the 3$^{rd}$ to 4$^{th}$ solvent switch may be from i-propyl acetate to 2-propanol.

In some aspects, it can be advantageous to treat the intermediate 13a with activated carbon to remove some color and trace impurities present before using this material in the next nitro-reduction step (i.e. the conversion of intermediate 13a to salt 14a). The activated carbon treatment may be carried out in a 5$^{th}$ solvent, such as EtOAc. Other suitable 5$^{th}$ solvents are tetrahydrofuran, 2-methyltetrahydrofuran, methanol, ethanol, methyl acetate, and i-propyl acetate. The activated carbon may be selected from the group consisting of, SX-Plus, Darco® S-51 HF, E Supra USP, SX-Ultra, CASP, Darco® G-60 and CGSP (all available from Norit®). In some aspects of the invention, the activated carbon is Darco® G-60, which provides the lowest amount of the trace impurity 16a (where q=1, 2, 3, 4, or 5), or 16 where q=2.

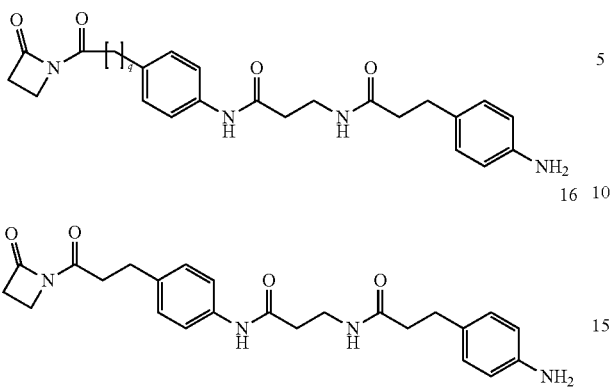

16a

16

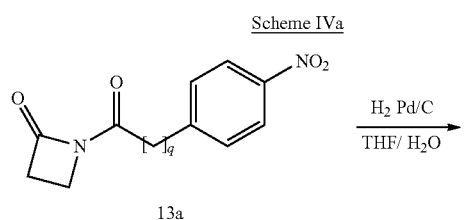

In some aspects, the purity of acid 9a is at least about 85%. In some aspects, the purity of acid 9a is at least about 90%. In some aspects, the purity of acid 9a is at least about 95%. In some aspects, the purity of acid 9a is at least about 96%. In some aspects, the purity of acid 9a is at least about 97%. In some aspects, the purity of acid 9a is at least about 98%. In some aspects, the purity of acid 9a is at least about 99%. The purity of the acid 9a can have a great impact on the reproducibility of the reaction. When 9a of purity less than 85% is used, 2 carbon treatments may be necessary to remove highly colored impurities, which causes the yield of coupling product 13a to drop to 48%.

A further benefit of carbon treatment was that the level of impurity 16a, resulting from the opening of the azetidinone ring by the newly formed amino group in the subsequent nitro reduction step, may be kept below acceptable levels. When the carbon treatment used Darco® G-60 in EtOAc, the level of impurity of 16a can be about 0.3%.

In some aspects, the invention provides for a new process for preparing compound 14a, comprising catalytic hydrogenation with Pd/C of compound 13a in a THF:H$_2$O solution of at least about 50% THF to produce a compound of formula 14a:

Scheme IVa

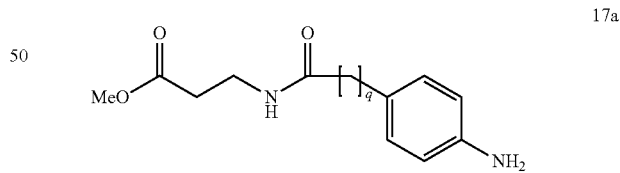

wherein q=1, 2, 3, 4, or 5. Where q=2, 13a may be 13 and 14a may be 14:

Scheme IV

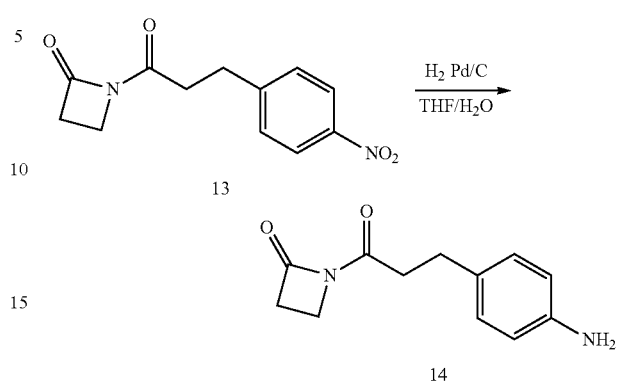

In some aspects, the THF:H$_2$O solution comprises at least about 60% THF. In some aspects, the THF:H$_2$O solution comprises at least about 70% THF. In some aspects, the THF:H$_2$O solution comprises at least about 80% THF. In some aspects, the THF:H$_2$O solution comprises at least about 90% THF. In some aspects, the THF:H$_2$O solution comprises about 90% THF. In some aspects, the THF:H$_2$O solution comprises up to about 99% THF. In some aspects, the THF:H$_2$O solution comprises up to about 95% THF. In some aspects, the ratio of THF:H$_2$O is between about 8-10:1. In some aspects, the ratio of THF:H$_2$O is about 9:1.

In some aspects, the 5% or 10% Pd/C is employed and used in 1-100% weight/weight ratio with respect to 13a. In some aspects, the catalytic hydrogenation takes place at a pressure of between about 1-50 psig. In some aspects, the catalytic hydrogenation takes place at about 15 psig. In some aspects, 13a is subjected to charcoal treatment substantially as described herein before the reaction. In some aspects, the catalyst may be filtered off and the filtrates treated with about 1 equiv of a strong acid (such as HCl (e.g. 12M), or similar, as discussed above) to generate and isolate the corresponding (HCl) salt.

Previously, the nitro-reduction step of compound 13a to compound 14a was carried out in methanol (MeOH) and provided approximately 68% yield of 14a. However, it has been found that using methanol results in a considerable amount of the impurity 17a (17, where q=2) (between about 1 and about 5%):

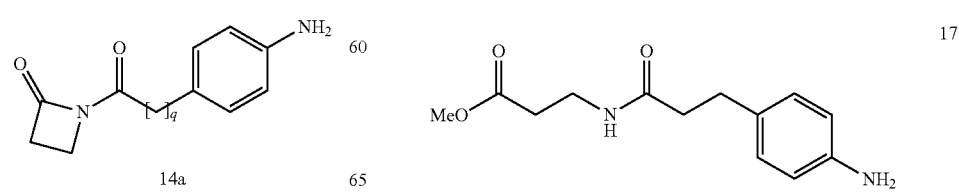

where q=1, 2, 3, 4, or 5

There therefore exists a need to improve the process of converting compound 13a to compound 14a. One potential solution to avoid the generation of 17a would be to use dioxane to prevent its formation. However, dioxane is a known carcinogen, and there therefore exists a need to find a safer alternative.

A proposed solution comprises the use of THF in conjunction with catalytic hydrogenation at a pressure range of between 1-50 psig (pound-force per square inch gauge). 15 psig with 10% Pd/C (10 wt %) in THF gave a fast reaction (<1 h) but the formation of variable levels of 16a were observed (1-5%) (other amounts of Pd metal by weight of the C support may also be useful; from 1-100%). Several additives were tested to prevent or reduce the formation of 16a (HCl, HOAc, $H_2O$, all at 10%) but compound 16a was still detected (1.8%, 1.9% and 1.6% respectively), as well as slower conversion.

The presence of water was a concern due to the potential opening of the azetidinone ring, but running the reaction in THF/$H_2O$ 9:1 (vol/vol) only caused a modest increase in impurity level.

The best results were obtained when starting material 13a was subjected to a charcoal treatment as described above, which kept the amount of impurity 16a at low levels (<0.3%) in the absence of additives.

Once full conversion of 13a to 14a (in some aspects, 13 to aniline 14) was attained, the catalyst (10% Pd/C) may be removed by filtration and the filtrates treated with 1 equiv of 12 M HCl to generate and isolate the corresponding HCl salt (which is the preferred form for long-term storage, as anilines have a tendency to undergo oxidation, giving rise to highly colored products). Other strong acids are suitable, such as sulphuric and nitric. The selection of the concentration and acid is largely determined so as to minimize volume and material loss.

In some aspects, the invention provides a process for preparing compound 6a, comprising combining a solution of 14a in a $6^{th}$ solvent with a compound according to formula 15 in a reaction substantially free of base to produce compound 6a Scheme Va

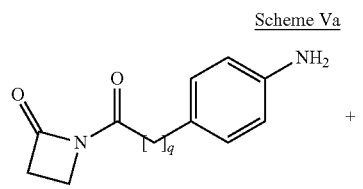

+

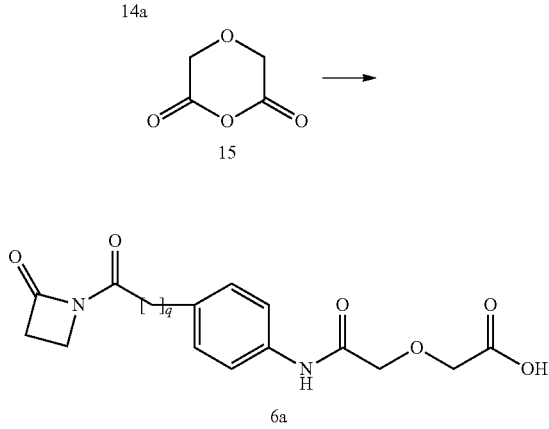

wherein q=1, 2, 3, 4 or 5;
from a solution of compound 14a

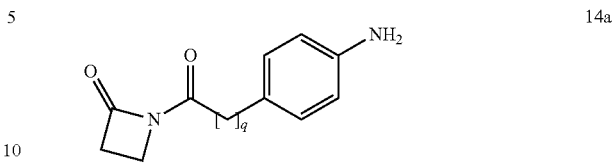

in THF,

Compound 15 may be added as a solution or as a solid. The $6^{th}$ solvent may be selected from the group consisting of THF, C1-C4 alkyl acetate, toluene, chloroform, methyl THF. In some aspects, the $6^{th}$ solvent is THF. In some aspects, the reaction is conducted in the absence of $H_2O$.

Where q=2, compound 6 may be prepared as described above using compound 14:

Scheme V

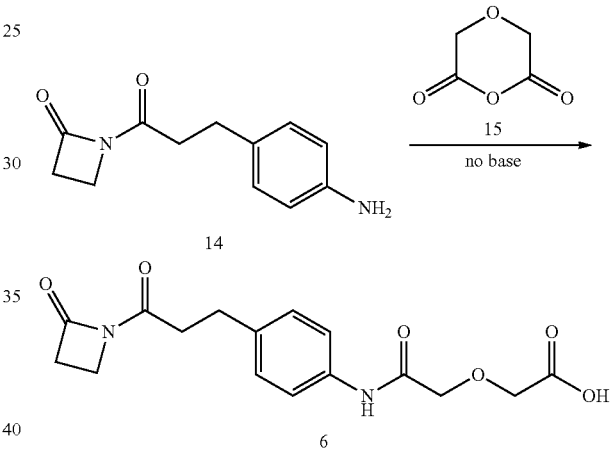

In part, some aspects of the invention are based on the surprising discovery that treating the THF filtrates containing 14a with about 1 equiv of diglycolic anhydride (15) in the absence of base led to the efficient formation of 6a. Compounds of the formula 14a, (such as aniline, 14), are only poorly nucleophillic, and require typically deprotonation with a base to increase their reactivity. Moreover, the HCL salt of compound 14, compound 14b, is solid, and can be stored for long periods of time, whereas a solution of 14 or 14a generally requires immediate usage. However, these disadvantages were outweighed by the surprising advantage of the present process of reduction in overall cycle time and cost of the reaction and purification.

In some aspects, compound 14a is reacted with about 1 equivalent of compound 15. In some aspects, compound 14a is reacted with at least about 1 equivalent of compound 15. In some aspects, compound 14a is reacted with between about 1 and about 10 equivalents of compound 15.

As a result, after reaction completion to form 6a, the present invention also provides for an additional process step; wherein the solution of compound 6a is distilled under vacuum to remove THF, following which, a $7^{th}$ solvent comprising $C_1$-$C_4$ alkyl acetate is added to attain a solvent composition of between about 25% THF/75% $C_1$-$C_4$ alkyl acetate and about 100% $C_1$-$C_4$ alkyl acetate. This may represent a total solvent volume of between about 5 and about 15 mls of solvent per gram of 6a. In some aspects, the $7^{th}$ solvent may comprise one of methyl acetate, ethyl acetate, i-propyl acetate, n-propyl acetate, n-butyl acetate. In some aspects, the $7^{th}$ solvent is either methyl acetate or i-propyl acetate. In some aspects, the $7^{th}$ solvent is methyl acetate. In some aspects, the $7^{th}$ solvent is i-propyl acetate.

Isolation in this manner results in a yield of 85-90% and typical residual solvent levels of 0.2 and 0.5 wt % for THF and i-PrOAc, respectively.

No change in yield or quality is seen when a final solvent ratio of between 25:75 $6^{th}$ solvent: $7^{th}$ solvent (THF:i-PrOAc) and 100& $7^{th}$ solvent (i-PrOAc) is employed. The telescoping of the THF solution of free base allows for a much simpler process and saves a considerable amount of time.

The reaction of 14a with 15 to form 6a is very fast (for example, <15 min in 60 volumes of solvent) and, after concentration of the THF solution, the addition of the $7^{th}$ solvent (e.g. i-propyl acetate) and cooling causes acid 6a to precipitate from solution in excellent yield (85-90%) and purity (>98%). This isolation method, while high yielding and fast, can result in relatively high residual solvent levels (e.g. 0.5-1% THF, 1-2% i-propyl acetate). Consequently, it was desirable to develop an alternative solvent exchange method to better control the final crystallization.

Crystallization of 6a from the $7^{th}$ solvent comprising a $C_1$-$C_4$ alkyl acetate (e.g. i-PrOAc) at a high temperature (e.g. 70° C.) causes product degradation (high temperature was needed to dissolve the material in a reasonable volume of solvent), whereas dissolution in acetone followed by solvent displacement with i-PrOAc and crystallization provided material that contained 0.5% residual i-PrOAc. Therefore, there exists a need to develop an optimized crystallization protocol, in order to further reduce the residual amount of solvent, (<0.25 wt %).

Accordingly, in some aspects, the invention provides for a further process step to crystallize acid 6a, comprising:
(i) dissolving acid 6a in an $8^{th}$ solvent comprising THF;
(ii) treating with activated carbon and then filtering off said activated carbon;
(iii) concentrating the acid 6a in THF solution to between about 2 and about 20 vol;
(iv) adding between about 1 and about 50 vol of a $1^{st}$ alcohol consisting of $C_1$-$C_6$ alkyl alcohol;
(v) concentrating the solution of acid 6a in THF and 2-propanol to between about 2 and about 50 vol;
(vi) cooling the concentrated solution of acid 6 to between about −25° C. and about 10° C.

In some aspects, the $8^{th}$ solvent is selected from the group consisting of THF, $C_1$-$C_4$ alkyl acetate, toluene, and acetonitrile. In some aspects the $8^{th}$ solvent is THF. In some aspects, 6a may be dissolved in the $8^{th}$ solvent at a temperature of between about 10° C. and about 67° C. The $8^{th}$ solvent may be present in an amount of between about 10 to about 50 volumes, and may be about 35 volumes.

In some aspects of the invention, such as where 6a is provided in a solution containing $C_1$-$C_4$ alkyl acetate, the solute may be removed, and 6a redissolved in the $8^{th}$ solvent, which may be THF. In some aspects of the invention, acid 6a may be dissolved in between about 20 to about 50 volumes of $8^{th}$ solvent, and in some aspects about 35 vol. In some aspects, acid 6a may be dissolved in the $8^{th}$ solvent at between about 15° C. and about 60° C. In some aspects, the temperature is between about 20° C. and about 40° C. In some aspects, the temperature is about 30° C.

After being dissolved in the $8^{th}$ solvent at step (i), the acid 6a may be subjected to an additional step; (ii): wherein the acid 6a is treated with activated carbon. The carbon treatment provides the advantage that removal of colour appears to lead to more predictable crystallization behavior The activated carbon may be selected from the group consisting of CGSP, SX-Plus, Darco S-51 HF, E Supra USP, SX-Ultra, CASP, Darco G-60 and Darco-KBB. In some aspects of the invention, the activated carbon is Darco-KBB. In some aspects, the activated carbon is added to a final amount of at least about 5% by weight of 6a. In some aspects, the activated carbon is added to a final amount of at least about 10% by weight of 6a. In some aspects, the activated carbon is added to a final amount of at least about 15% by weight of 6a. In some aspects, the activated carbon is added to a final amount of about 20% by weight of 6a.

The acid 6a/$8^{th}$ solvent solution may be treated with activated carbon for at least about 15 mins, and in some aspects, at least about 1 hr, and may be between about 1 and about 24 hrs.

In some aspects, the activated carbon is filtered off (for example, using a filter aid, such as celite). In some aspects, the solution (filtrates) may then be concentrated (for example, under reduced pressure, such as between about 0 and about 1 atmospheres pressure) at step (iii) to between about 2 and about 20 volumes. In some aspects, the filtrates may then be concentrated to between about 5 and about 15 volumes. In some aspects, the filtrates may then be concentrated to about 10 volumes.

In some aspects, between about 1 and about 50 volumes of $1^{st}$ alcohol may be added to the solution at step (iv). In some aspects, excess $1^{st}$ alcohol may be added to initiate precipitation of 6a from the $8^{th}$ solvent. In some aspects, between about 1 and about 30 volumes of $1^{st}$ alcohol may be added. In some aspects, between about 1 and about 20 volumes of $1^{st}$ alcohol may be added. In some aspects, between about 5 and about 50 volumes of $1^{st}$ alcohol may be added. In some aspects, between about 5 and about 30 volumes of $1^{st}$ alcohol may be added. In some aspects, between about 12 and about 16 volumes of 1st alcohol may be added. In some aspects, about 14 volumes of $1^{st}$ alcohol may be added.

The $1^{st}$ alcohol may be selected from the group consisting of $C_1$-$C_6$ alkyl alcohols, including methanol, ethanol, 1-propanol, 2-propanol, 1-butanol, 2, butanol, 1-pentanol, 2-pentanol, 3-pentanol, 1-hexanol, 2-hexanol, 3-hexanol, 3-methyl-1-butanol, 2-methyl-1-butanol, 2,2-dimethyl-1-propanol, 3-methyl-2-butanol, and 2-methyl-2-butanol. In some aspects, the $1^{st}$ alcohol may be a primary or secondary $C_1$-$C_6$ alkyl alcohol. In some aspects, the $1^{st}$ alcohol may secondary $C_1$-$C_6$ alkyl alcohol. In some aspects, the $1^{st}$ alcohol may be 2-propanol.

In some aspects, $1^{st}$ alcohol may be added to the concentrated solution of acid 6 at step (iv) at a ratio of between about 0.5 to about 10:about 1. In some aspects, the ratio is between about 0.5:1 and about 5:1. In some aspects, excess $1^{st}$ alcohol is added. In some aspects, the ratio is between about 1:1 and about 3:1. In some aspects, the ratio is between about 1:1 and about 2:1. In some aspects, the ratio is between about 1.2:1 and about 6:1. In some aspects, the ratio is between about 1:3 and about 1.5:1. In some aspects, the ratio is about 1.4:1.

In some aspects, the solution of acid 6a in $8^{th}$ solvent and $1^{st}$ alcohol from step (iv) may then be concentrated to between about 1 and about 50 vol. In some aspects, the solution of acid 6a in $8^{th}$ solvent and $1^{st}$ alcohol may be concentrated to between about 1 and about 30 vol. In some aspects, the solution of acid 6a in $8^{th}$ solvent and $1^{st}$ alcohol may be concentrated to between about 5 and about 20 vol. In some aspects, the solution of acid 6a in $8^{th}$ solvent and $1^{st}$ alcohol may be concentrated to between about 5 and about 20 vol. In some aspects, the solution of acid 6a in 8$^{th}$ solvent and 1$^{st}$ alcohol may be concentrated to between about 5 and about 15 vol. In some aspects, the solution of acid 6a in 8$^{th}$ solvent and 1$^{st}$ alcohol may be concentrated to about 10 vol.

In some aspects, the solution of acid 6a in 8$^{th}$ solvent and 1$^{st}$ alcohol from step (iv) may be concentrated, ideally under reduced pressure. In some aspects, atmospheric pressure may be used. In some aspects, between a full vacuum and 1 atmosphere may be used to concentrate 6a.

In some aspects, the solution from step (v) may then be cooled so as to enable acid 6a to crystallize. In some aspects, the solution from step (v) may be cooled to between about −25° C. to about 10° C. In some aspects, the solution from step (v) may be cooled to between about −20° C. to about 10° C. In some aspects, the solution from step (v) may be cooled to between about −20° C. to about 5° C. In some aspects, the solution from step (v) may be cooled to between about −5° C. to about 10° C. In some aspects, the solution from step (v) may be cooled to between about −5° C. to about 5° C. In some aspects, the solution from step (v) may be cooled to between about −5° C. to about 0° C. In some aspects, the solution from step (v) may be cooled to between about −1° C. to about 4° C. In some aspects, the solution from step (v) may be cooled to between about −0° C. to about 4° C. In some aspects, the solution from step (v) may be cooled to between about 0° C. to about 5° C.

In some aspects, after filtering the carbon off, the mixture may be concentrated (for example, by distillation at reduced pressure (0-1 atm) to 10 vol, to which about 14 vol of 1$^{st}$ alcohol may be added. The solution may then be further concentrated to about 10 vol, and then cooled to between about −20° C. to about 10° C., and preferably between about 0 and about 5° C. Such a protocol affords acid 6a in 80% recovery and >99% chemical purity. This especially advantageous embodiment of the invention delivers significantly smaller particles (~30μ) than the original THF/i-PrOAc crystallization (100-200μ) and the smaller particle size may explain why less solvent was trapped in the crystals.

In some aspects, the invention is based on the successful identification of activated esters that may be easily prepared in high yield and stored over prolonged periods of time before being conjugated to peptides and proteins and the like, and methods of making said activated esters.

A need was identified to develop a process for the conjugation of peptide 2 to acid 6a that allowed for the isolation of peptide-linker conjugate 3a in high yield and purity without resorting to the time and resource expensive chromatographic purifications and lyophilizations present in the original synthesis. It is further desirable that the improved process provides a chemical purity of ≥95% with no single impurity above 2% and residual solvent content below 0.25% (wt/wt) for each individual solvent.

Accordingly, in some aspects, the invention provides for compounds and intermediates of the formulae:

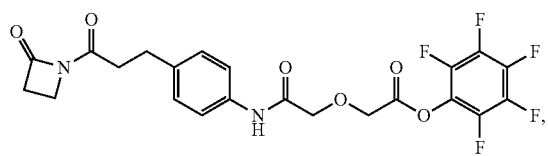

20

-continued

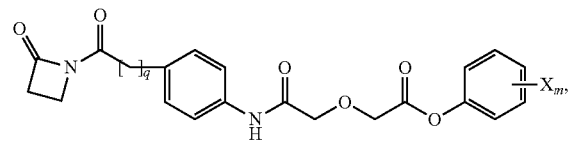

20a

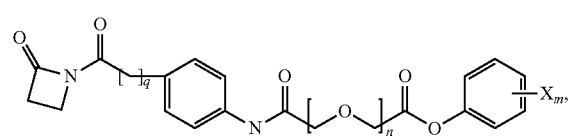

20b

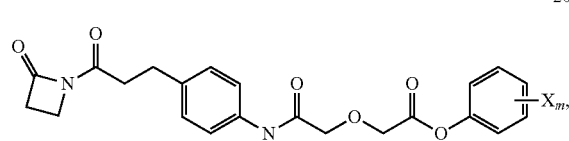

20c

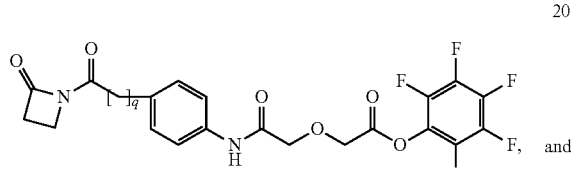

20d

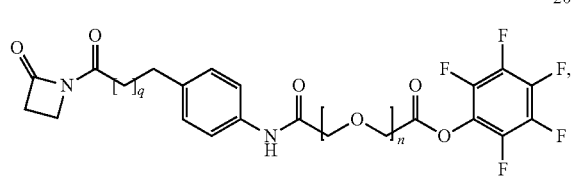

20e wherein q is 1, 2, 3, 4, or 5, n=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and X is any halogen, and m=3, 4 or 5. X may be F or Cl, and preferably is F. M may be 4 or 5, and preferably is 5. In some aspects, n=1-10. In some aspects, n=1, 2, 3, 4, 5, or 6. In some aspects, q=1, 2, or 3. In some aspects, q=2.

In some aspects, the invention provides a method of generating activated esters of formula 20 and 20a, 20b, 20c, 20d, and 20e. In some aspects, the invention provides a method of generating activated esters of formula 20, 20a, 20c, and 20d.

The preparation of the acid chloride derivative of 6a with either Cl$_2$SO or (COCl)$_2$ or activation with reagents such as CU or chloroformate was ruled out due to their high reactivity, as the resulting intermediates would readily cyclize to give compounds such as 18a, for example, morpholine-3,5-dione 18, where q=2.

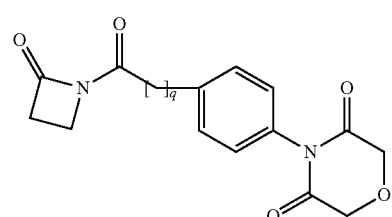

18a q=1, 2, 3, 4, or 5.

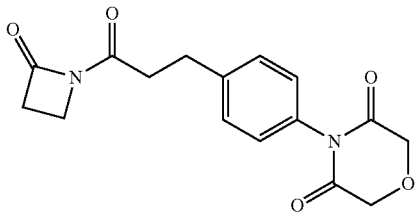

18

In part, the invention is based on the discovery that when acid 6a (such as 6) and compounds such as tri-, tetra-, and penta-halo substituted phenol compounds of formula 19a (such as pentafluorophenol 19) undergo reaction in the presence of DCC in a $10^{th}$ solvent such as THF, esters 20a are obtained in 80-85% yield (such as 20). Other suitable $10^{th}$ solvents in place of THF include dichloromethane, 2-methyltetrahydrofuran, N,N-dimethylformamide, and N,N-dimethylacetamide.

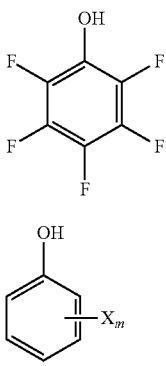

19

19a where X=F or Cl, and m=3, 4, or 5.

Accordingly, in some aspects the invention provides a process where a compound according to formula 6b is reacted with a compound according to formula 19a in a $10^{th}$ solvent in the presence of DCC to form a compound according to formula 20b.

Scheme VIIIb

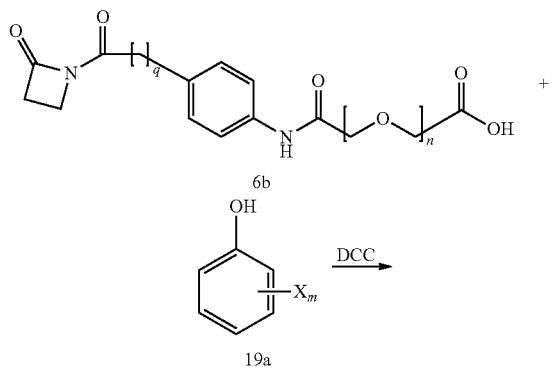

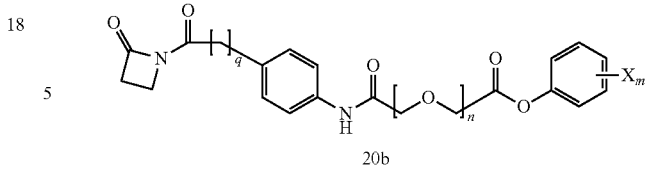

20b wherein q=1, 2, 3, 4, or 5, n=1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, X=F or Cl, and m=3, 4, or 5.

In some aspects, the ratio of 19a relative to 6b is at least about 1. In some aspects, the ratio of 19a:6b is about 1:1. In some aspects, excess 19a is added to 6b. In some aspects, the ratio of 19a:6b is about 2:1.

In some aspects, the reaction takes place in a $10^{th}$ solvent selected from the group consisting of THF, dichloromethane, 2-methyltetrahydrofuran, N,N-dimethylformamide, and N,N-dimethylacetamide. In some aspects, the $10^{th}$ solvent is THF.

In some aspects, the DCC is added to the solution of 6b and 19a at between about −10 to about 10° C., preferably between about 0 to about 10° C., and more preferably between about 3 and about 5° C. After a mixing time of at least about 1 min and preferably at least about 10 mins, the reaction solution may be heated to about RT (for example, between about 15 and about 25° C., preferably between about 18 and about 22° C., most preferably about 20° C.), and stirred for at least 4, preferably at least 6, more preferably at least 12 hrs, most preferably for about 18 hrs.

After reaction, the solution may be filtered (to remove byproducts, such as dicyclohexylurea), and washed with an $11^{th}$ solvent selected from the group consisting of THF, dichloromethane, 2-methyltetrahydrofuran, N,N-dimethylformamide, and N,N-dimethylacetamide. In some aspects, the $11^{th}$ solvent is THF. Following this, the solids may be resuspended in the $11^{th}$ solvent, and mixed with acetone (in some aspects, the acetone may be substitute with $C_1$-$C_4$ alkylacetate, toluene, MTBE, or acetonitrile). The ratio of $11^{th}$ solvent to acetone may be between about 2:1 to about 1:2, and is preferably about 1:1. IN some aspects, it is desirable to use excess acetone.

The solution may be cooled to at least 15° C., and preferably at least about 12° C., and most preferably at least about 10° C., and preferably up to about 0° C. Optionally, the solution may then be stirred for at least 10 mins, and preferably at least 30, at least 60 and at least 80 mins. The solution may then be filtered and the solid washed with acetone (or similar, as discussed above).

The filtrates may be resuspended in a $12^{th}$ solvent selected from the group consisting of THF, dichloromethane, 2-methyltetrahydrofuran, N,N-dimethylformamide, and N,N-dimethylacetamide. In some aspects, the $12^{th}$ solvent is THF. The $12^{th}$ solvent may be mixed with a $2^{nd}$ alcohol (which may be selected from the same group as the $1^{st}$ alcohol, excepting methanol, and may be 2-propanol) to a ratio of between about 2:1 to about 1:2, and preferably about 1:1 to create a slurry. In some aspects, the ration is at least about 1:1 so as to provide an excess of $2^{nd}$ alcohol.

The slurry may be stirred for at least 1 hr, at least 6 hr, at least 12 hr. The slurry may be stirred at between about 4 and about 30° C., or between about 12 and about 25° C. or between about 18 and about 22° C., or about 20, or at RT.

The slurry may be filtered, washed with a $3^{rd}$ alcohol (which may be selected form the same group as the $2^{nd}$ alcohol, and may be 2-propanol), and dried. The obtained solid may be dried under vacuum. The obtained solid may be dried at between RT and about 50° C., and preferably about 40° C. The solid may be dried for at least about 1, at least about 4, at least about 12 and preferably at least about 16 hrs.

Compound 20 may be similarly prepared by the advantageous processes of the invention, using compounds such as 6 and 19 as starting material. Compound 20a may be similarly prepared by the advantageous processes of the invention, using compounds such as 6a and 19a as starting material. Compound 20c may be similarly prepared by the advantageous processes of the invention, using compounds such as 6 and 19a as starting material. Compound 20d may be similarly prepared by the advantageous processes of the invention, using compounds such as 6a and 19 as starting material. Compound 20e may be similarly prepared by the advantageous processes of the invention, using compounds such as 6b and 19 as starting material.

In some aspects, the addition reaction compound 6 and compound 19 in the presence of DCC in THF produces compound 20 at a yield of at least 80%, and in some cases, at least 85%.

In some aspects acid 6b and 19a are reacted together at a temperature of between about −25° C. and about 50° C. In some aspects acid 6b and 19a are reacted together at a temperature range whose lower limit is selected from the group consisting of about −25, −20, −15, −10, −5, −1, 0, 1, 4, 5, 10, 15, 16, 17, 18, 19, 20, 21, and 22° C. and whose upper limit is selected from the group consisting of about −1, 0, 1, 4, 5, 10, 15, 16, 17, 18, 19, 20, 21, 22, 23, 24, 25, 30, 35, 40, 45, and 50° C. In some aspects acid 6b and 19a are reacted together at a temperature of between about −0° C. and about 20° C. In some aspects, the reaction is at about −15° C.

In some aspects acid 6b and 19a are reacted together for at least 1 hr. In some aspects acid 6b and 19a are reacted together for at least 2 hrs. In some aspects acid 6b and 19a are reacted together for at least 3 hrs. In some aspects acid 6b and 19a are reacted together for at least 4 hrs. In some aspects acid 6b and 19a are reacted together for at least 6 hrs. In some aspects acid 6b and 19a are reacted together for at least 8 hrs. In some aspects acid 6b and 19a are reacted together for at least 12 hrs. In some aspects linker 6b and 19a are reacted together for at least 18 hrs. In some aspects linker 6b and 19a are reacted together for about 24 hrs.

In some aspects, acid 6b and 19a are reacted together at between about 1:1 and about 1:10 ratio.

In some aspects, a coupling agent may be added. The role of this coupling agent is the activation of acid 6b to produce a more reactive intermediate that is capable of reacting with phenol 19a to afford the desired ester. In the absence of coupling agent, no ester bond formation occurs. The coupling agent may be selected from the group consisting of DCC, CDI, CDMT, DCMT, DIC, DPPA, EDC, HATU, HBTU, PyBOP, PyBroP, PyCloP, TBTU, and T3P. In some aspects, the coupling agent is DCC.

Esters 20, 20a, 20b, 20c, 20d and 20e may be isolated via chromatographic purification. In a further aspect of the invention, esters 20, 20a, 20b, 20c, 20d and 20e may be precipitated from a $14^{th}$ solvent such as isopropanol (as exemplified in Example 11). Other suitable $14^{th}$ solvents include ethanol and butanol.

Ester 20 is a fine, white solid that is stable for months at room temperature in contact with air, without the need for any special storage conditions, and that shows no detectable amounts of cyclic morpholine-3,5-dione 18. In addition, it displays excellent reactivity in the final conjugation step to form 1 (vide infra).

In some aspects, the invention provides an improved process for generating compound 3b comprising
(i) mixing 1 equiv of peptide 2 in an aprotic, polar $15^{th}$ solvent, and
(ii) combining excess 20b with peptide 2 to produce 3b Scheme VIIb

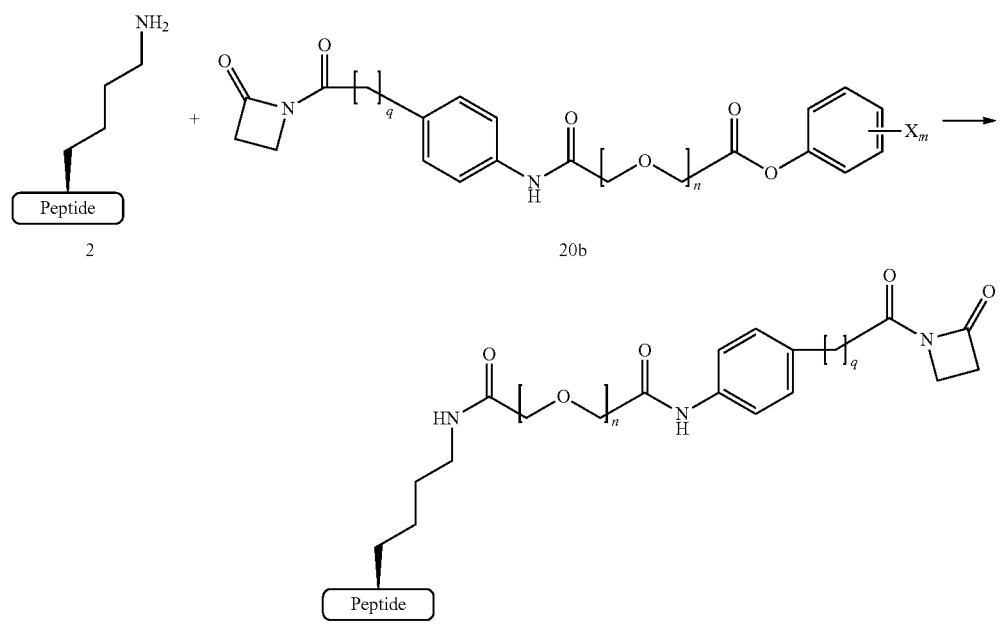

wherein n=1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, q=1, 2, 3, 4, or 5, X=F or Cl, and m=3, 4, or 5.

In some aspects, the aprotic, polar $15^{th}$ solvent is selected from the group consisting of DMF, DMAc, DMSO or NMP. In some aspects, the aprotic polar solvent is DMF.

In some aspects, peptide 2 can be either a salt such as trifluoroacetate salt of 2 or a free base form. Where peptide 2 is a salt, then step (i) is carried out in a $2^{nd}$ base. Where peptide 2 is provided as a free base form, then the $2^{nd}$ base is not required.

In some aspects, peptide 2 is dissolved in between about 5 and about 50 volumes of the aprotic polar $15^{th}$ solvent. In some aspects, peptide 2 is dissolved in between about 10 and about 20 volumes of the aprotic polar $15^{th}$ solvent. In some aspects, peptide 2 is dissolved in about 15 volumes of the aprotic polar $15^{th}$ solvent.

In some aspects of the invention, the $2^{nd}$ base is selected from the group consisting of NMM, TEA, DIPEA, pyridine, DABCO, DBU, and lutidine. In some aspects, the $2^{nd}$ base may be TEA, DIPEA or pyridine.

The $2^{nd}$ base may be present in an amount of between about 1 and about 10 equiv. In some aspects, the $2^{nd}$ base is present in an amount of about 1 to about 5 equiv. In some aspects, the $2^{nd}$ base is present in an amount of about 1 to about 3 equiv. In some aspects, the $2^{nd}$ base is present in an amount of about 1 to about 2 equiv. In some aspects, the $2^{nd}$ base is present in an amount of about 1 to about 1.5 equiv. In some aspects, the $2^{nd}$ base is present in an amount of about 1.2 equiv.

However, both peptide 2 and peptide-linker conjugate 3 tend to form thick gels in aprotic, polar $15^{th}$ solvents such as DMF, DMAc, and DMSO after a few hours, either in the presence or absence of water. The solution to this problem is to react peptide 2 with 20b within about 18 hrs of dissolving peptide 2 in the aprotic polar $15^{th}$ solvent; preferably within about 12 hrs, more preferably within about 8 hrs, more preferably within about 6 hrs more preferably within about 4 hrs, more preferably within about 2 hrs, more preferably within about 1 hr. In addition, the problem of gelification is made less acute by use of at least, 10, and favourably, at least 15 volumes of aprotic polar $15^{th}$ solvent.

In some aspects, between about 1 and about 30 equiv of 20b may be added to about 1 equiv of peptide 2. In some aspects, between about 1 and about 20 equiv of 20b may be added to about 1 equiv of peptide 2. In some aspects, between about 1 and about 10 equiv of 20b may be added to about 1 equiv of peptide 2. In some aspects, between about 2 and about 30 equiv of 20b may be added to about 1 equiv of peptide 2. In some aspects, between about 3 and about 30 equiv of 20b may be added to about 1 equiv of peptide 2. In some aspects, between about 3 and about 20 equiv of 20b may be added to about 1 equiv of peptide 2. In some aspects, between about 3 and about 10 equiv of 20b may be added to about 1 equiv of peptide 2. In some aspects, at least 3 equiv of 20b is added to about 1 equiv of peptide 2. In some aspects, about 3 equiv of 20b may be added to about 1 equiv of peptide 2.

In some aspects, the 20b and 2 are combined in between about 1 to about 10 equiv of $3^{rd}$ base, compared to peptide 2. In some aspects, the 20b and 2 are combined in between about 1 to about 5 equiv of $3^{rd}$ base, compared to peptide 2. In some aspects, the 20b and 2 are combined in between about 1 to about 2 equiv of $3^{rd}$ base, compared to peptide 2. In some aspects, the 20b and 2 are combined in between about 1 to about 1.5 equiv of $3^{rd}$ base, compared to peptide 2. In some aspects, the 20b and 2 are combined in about 1.3 equiv of $3^{rd}$ base, compared to peptide 2. The $3^{rd}$ base may be selected from the group consisting of NMM, TEA, DIPEA and pyridine. The $3^{rd}$ base may be NMM.

Due to the low solubility of peptide 2, no conversion to peptide-linker conjugate 1 was observed in solvents such as MeCN or MeOH. The addition of water to these solvents to help bring peptide 2 into solution led to low conversions due to activated linker decomposition and to the formation of thick gels after a few hours.

In accordance with the present invention, aprotic, polar solvents (such as DMF), may fully dissolve peptide 2 and allow full consumption of the peptide 2 at RT (e.g. about 20° C.) with about 3 equiv of compound 20b. The cleanest reaction was obtained in DMF in combination with NMM as base. Lower purities were obtained in DMSO, NMP and DMAc with bases such as TEA, DIPEA or pyridine. In some aspects, the reaction comprises mixing about 20 volumes of DMF, between about 2 to about 3 equiv of 20b, and about 20 equiv of NMM. The reaction may be at RT. The reaction may be carried out for at least 10 minutes.

Conditions for the isolation of peptide-linker conjugate 3 were also investigated. The simplest approach was the identification of a suitable anti-solvent that would precipitate peptide-linker conjugate 3 from solution followed by filtration. A number of organic solvents were tested for this purpose. Whereas toluene, EtOAc, THF, and MTBE gave sticky, gel-like solids that were difficult to filter, some aspects of the invention are based on the surprising discovery that MeCN produced fine, free-flowing solids that are much more easily handled.

Accordingly, in some aspects of the invention, 3 may be subsequently isolated by precipitation with MeCN, followed by filtration.

In some aspects, the proportion of anti-solvent:aprotic, polar $15^{th}$ solvent is between about 5:1 to about 20:1, and is preferably about 9:1.

Filtration in the presence of an inert gas ($N_2$, Ar, $CO_2$ etc) at this point was desirable to prevent moisture adsorption on the cake, otherwise the product may turn into a gummy solid. The workup procedure involved the slow transfer of the DMF solution of peptide-linker conjugate 3 after reaction completion into MeCN to give a final 9:1 MeCN/DMF mixture. After the resulting precipitate was aged (where the solid is afforded sufficient time to precipitate out of solution), the solid was filtered and dried at between about 0 to about 50° C. under vacuum. In some aspects, the precipitate was aged for up to 24 hrs. In some aspects, the precipitate was aged for up to 12 hrs. In some aspects, the precipitate was aged for up to 6 hrs. In some aspects, the precipitate was aged for up to 3 hrs. In some aspects, the precipitate was aged for up to 2 hrs. In some aspects, further stirring after about 2 hrs makes the solid sticky and difficult to handle. In some aspects, the solid was dried at about 0 to about 40° C. In some aspects, the solid was dried at about 20 to about 50° C. Higher temperatures are likely to have a detrimental effect.

Accordingly, in some aspects of the invention, the filtration may be conducted in the absence of water vapour or atmosphere. In some aspects, the filtration may be conducted under inert gas. The inert gas may be selected from the group consisting of $N_2$, Argon, $CO_2$, etc.

In some aspects of the invention, the peptide 2 and compound 20b may be conjugated together at a temperature of between about −30° C. and about 30° C. In some aspects of the invention, the peptide 3 and the compound 20b may be conjugated together at a temperature range whose lower limit is selected from the group consisting of about −30, −25, −20, −18, −17, −16, −15, −14, −13, −12, −10, −5, −1, 0, 1, 2, 3, 4, 5, 10, 15 and 18° C., and whose upper limit is selected from the group consisting of about −14, −13, −12, −10, −5, −1, 0, 1, 2, 3, 4, 5, 10, 15, 20, 25 and 30° C. In some aspects of the invention, the peptide 2 and compound 20b may be conjugated together at a temperature of between about −30° C. and about 20° C. In some aspects of the invention, the peptide 2 and compound 20b may be conjugated together at a temperature of about −15° C.

In some aspects conjugation between 2 and 20b proceeds even at −30° C. but can require between about 18 to about 20 hrs, and may necessitate up to about 5 equiv of pentafluorophenol ester linker to fully consume the peptide. In addition, the longer reaction times can give more byproduct formation as well as hazy mixtures due to partial product precipitation. After further experimentation, a satisfactory compromise was surprisingly found between the kinetics of the process and a satisfactory impurity profile. Accordingly, in some aspects, the invention provides for a process that runs the reaction in about 15 volumes of DMF, preferably between about 15 to about 50 volumes of DMF, (enough to easily dissolve peptide 2 and prevent gelification) in the presence of about 3 equiv of compound 20b and between about 1 and about 5, and preferably about 1.2 equiv NMM at between about −15 to about −18° C. After about 7 hr, less than about 1% of unreacted 2 remained and the total byproduct of ester 20b was kept at or below about 0.3%.

After 7 hrs, less than 1% of unreacted 2 remained and the total pentafluorophenol ester byproduct level was kept at 0.3%. The mixture may then be filtered through a 0.45 micron in-line filter and slowly added into the anti-solvent, such as MeCN, while using low agitation to promote larger particle size.

The amount of MeCN may be advantageously chosen such that the final desired ratio of MeCN:DMF is achieved. In some aspects, the amount of MeCN is about 5 to about 20 times the amount of aprotic polar solvent, and may be arranged so as to give a final ratio of MeCN:DMF of 9:1.

Solid precipitation typically occurs immediately and, after an aging period (for example, about 1-2 hrs), the solids may be filtered, washed with fresh MeCN, and dried under vacuum.

In some aspects, a DMF content of 4.5% (wt/wt) may still be present in the solid, most likely due to the intentional slow agitation during the quick precipitation of the product from solution and the resulting entrapment of DMF. Screening the solid through a #20 hand-sieve followed by a MeCN reslurry (wherein the solid was suspended in a solvent and stirred without fully dissolving the solid to remove impurities), and subsequent drying at between about 20 and about 50° C., and preferably at about 40° C. provides material in 83% yield.

In some aspects, a high agitation speed or subsurface addition of the product solution into MeCN during the precipitation can minimize the amount of trapped DMF.

Accordingly, in some aspects the invention provides a means to minimize the entrapment of DMF in the isolated product solids, comprising the addition of the product solution into MeCN with vigorous mixing. This can be accomplished using high speed agitation in the isolation vessel, or preferably, by also adding the product solution through an addition tube whose outlet is below the surface of the MeCN and near a region of high shear (close to the impeller blades). The vigorous agitation allows the product solution to be more thoroughly dispersed before precipitation and reduces the concentration of DMF in the region of precipitation.

Room temperature (RT) may be between about 15° C. and about 25° C. In some aspects, RT may be between about 18° C. and about 22° C. In some aspects, RT may be between about 18° C. and about 20° C. In some aspects, RT may be between about 20° C.

In some aspects, the invention provides for use of PNP esters rather than tri-, tetra- and penta-halo substituted phenyls. Accordingly, in some aspects the invention provides for compounds and intermediates of the formulae:

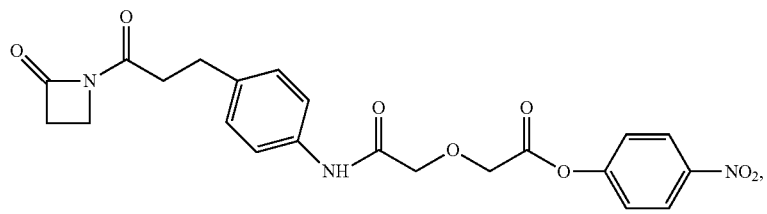

22

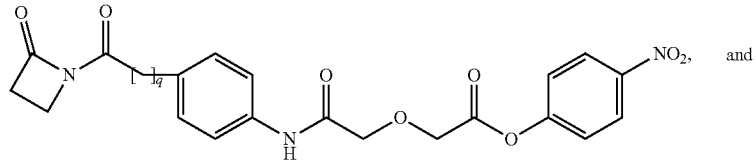

22a and

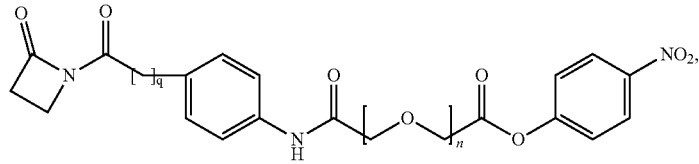

22b wherein q is 1, 2, 3, 4, or 5, n=1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and X is any halogen. In some aspects, n=1-10. In some aspects, n=1, 2, 3, 4, 5, or 6. In some aspects, q=1, 2, or 3. In some aspects, q=2.

In some aspects, the invention provides a method of generating activated esters of formula 22, 22a, and 22b, comprising reacting compound 21 with compound 6, 6a, or 6b respectively (using the same chemistry as described for reaction of 6b and 19b). Compounds 22, 22a, and 22b can be conjugated with ε-amino group-bearing side chains (e.g. a lysine side chain) of peptides 2 to form peptide-linker conjugates 3, 3a, and 3b respectively.

21

The surprising part of this aspect of the invention is that use of PNP esters of the formula 22, 22a and 22b for the coupling with the peptide 2 afford products 3, 3a, 3b respectively that do not contain corresponding PNP ester impurities of 3, 3a, 3b. Possible chemical structures of these impurities are shown below.

impurities in the drug substance (see discussion in example 16). In some aspects, the invention describes a process for preparation of peptide-linker-antibody 5 of the formula shown below. In some aspects, the antibody is h38C2 or variants thereof. In some aspects, the peptide-linker is 3, 3a or 3b.

Abbreviations
n-BuLi: n-butyl lithium
CDI: 1,1'-carbonyldiimidazole
CDMT: 2-chloro-4,6-dimethoxy-1,3,5-triazine
DBU: 1,8-diazabicyclo[5.4.0]undec-7-ene
DABCO: 1,4-diazabicyclo[2.2.2]octane
DCC: N,N'-dicyclohexylcarbodiimide
DCMT: 2,4-dichloro-6-methoxy-1,3,5-triazine
DIC: N,N'-diisopropylcarbodiimide
DIPEA: diisopropylethylamine
DMAc: N,N-dimethylacetamide
DMF: N,N-dimethylformamide
DMSO: dimethylsufoxide

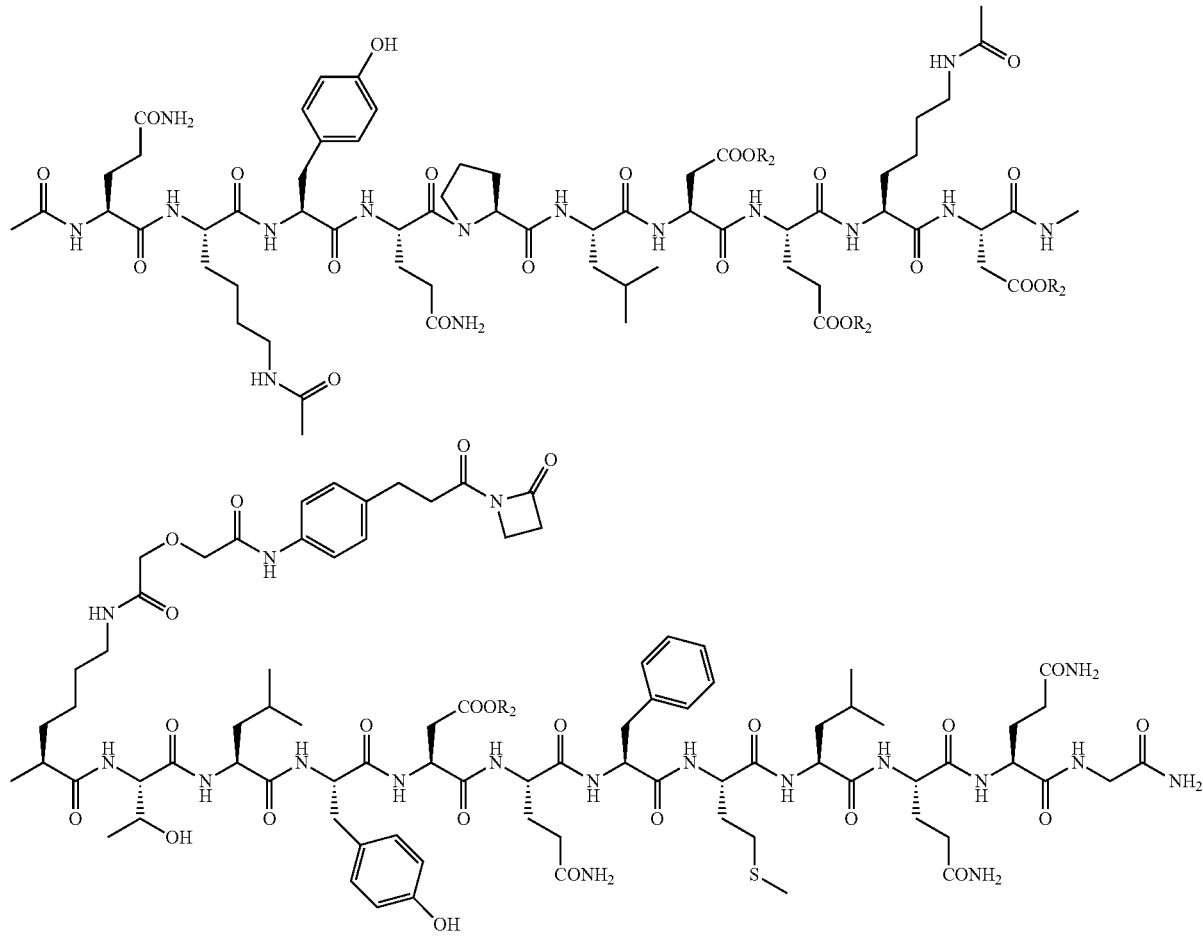

$R_1, R_2, R_3, R_4$ = H or p-nitrophenyl

These types of impurities are typically formed when penta halophenol esters are used as activating groups during coupling reaction of 20b with 2 resulting in the formation of corresponding pentahalo ester impurities (see example 16). These impurities are very reactive and can potentially react with a monoclonal antibody used in subsequent conjugation steps, such as h38C2, resulting in the formation undesired DPPA diphenylphosphoryl azide
EDC: 1-[3-(dimethylaminopropyl]-3-ethylcarbodiimide hydrochloride
EtOAc: ethyl acetate
HATU: O-(7-azabenzotriazol-1-yl)-1,1,3,3-tetramethyluronium hexafluorophosphate HBTU: O-(benzotriazol-1-yl)-1,1,3,3-tetramethyluronium hexafluorophosphate
HOAc: acetic acid
MeCN: acetonitrile
MeOH: methanol
MTBE: tert-butyl methyl ether
$NH_4OAc$: ammonium acetate
NMM: N-methylmorpholine
NMP: 1-methyl-2-pyrrolidinone
PFP pentafluorophenyl
PNP para nitrophenyl
i-PrOAc: i-propyl acetate PyBOP: benzotriazol-1-yloxytri(pyrrolidino)phosphonium hexafluorophosphate
PyBroP: bromotri(pyrrolidino)phosphonium hexafluorophosphate
PyCloP: chlorotri(pyrrolidino)phosphonium hexafluorophosphate
T3P: 1-propanephosphonic acid anhydride
TBTU: O-benzotriazol-1-yl-1,1,3,3-tetramethyluronium tetrafluoroborate
TEA: triethylamine
THF: tetrahydrofuran
HIC Hydrophoboic interaction chromatography
SEC Size Exclusion Chromatography

SEQUENCE LIST

| SEQ ID NO: | Description | Sequence |
|---|---|---|
| 1 | Ang2 binding peptide<br>X2 is Acyl Lysine<br>X9 is acyl lysine | QxYQPLDExD KTLYDQFMLQ QG |
| 2 | Ang2 binding peptide<br>X1 is $C(O)CH_3$<br>X3 is Acyl Lysine<br>X10 is acyl lysine<br>X24 is $NH_2$ | xQxYQPLDEx DKTLYDQFML QQGx |
| 3 | h38C2 light chain | ELQMTQSPSS LSASVGDRVT ITCRSSQSLL HTYGSPYLNW YLQKPGQSPK<br>LLIYKVSNRF SGVPSRFSGS GSGTDFTLTI SSLQPEDFAV YFCSQGTHLP<br>YTFGGGTKVE IKRTVAAPSV FIFPPSDEQL KSGTASVVCL LNNFYPREAK<br>VQWKVDNALQ SGNSQESVTE QDSKDSTYSL SSTLTLSKAD YEKHKVYACE<br>VTHQGLSSPV TKSFNRGEC |
| 4 | h38C2 heavy chain | EVQLVESGGG LVQPGGSLRL SCAASGFTFS NYWMSWVRQS PEKGLEWVSE<br>IRLRSDNYAT HYAESVKGRF TISRDNSKNT LYLQMNSLRA EDTGIYYCKT<br>YFYSFSYWGQ GTLVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPELLGGPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPGK |
| 5 | VL h38C2 | ELQMTQSPSS LSASVGDRVT IT*CRSSQSLL HTYGSPYLNW* YLQKPGQSPK<br>LLIYKVSNRF SGVPSRFSGS GSGTDFTLTI SSLQPEDFAV YFCSQGTHLP<br>YTFGGGTKVE IK |
| 6 | VH h38C2 | EVQLVESGGG LVQPGGSLRL SCAASGFTFS NYWMSWVRQS PEKGLEWVSE<br>IRLRSDNYAT HYAESVKGRF TISRDNSKNT LYLQMNSLRA EDTGIYYCKT<br>YFYSFSYWGQ GTLVTVSS |
| 7 | VL m38C2 | DVVMTQTPLS LPVRLGDQAS ISCRSSQSLL HTYGSPYLNW YLQKPGQSPK<br>LLIYKVSNRF SGVPDRFSGS GSGTDFTLRI SRVEAEDLGV YFCSQGTHLP<br>YTFGGGTKLE IK |
| 8 | VH m38C2 | EVKLVESGGG LVQPGGTMKL SCEISGLTFR NYWMSWVRQS PEKGLEWVAE<br>IRLRSDNYAT HYAESVKGKF TISRDDSKSR LYLQMNSLRT EDTGIYYCKY<br>YFYSFSYWGQ GTLVTVSA |
| 9 | h38C2-IgG1 LC constant region genus<br>x46 = V or A,<br>x84 = V or L | RTVAAPSVFI FPPSDEQLKS GTASVVCLLN NFYPREAKVQ WKVDNxLQSG<br>NSQESVTEQD SKDSTYSLSS TLTLSKADYE KHKxYACEVT HQGLSSPVTK<br>SFNRGEC |
| 10 | h38C2-IgG1 LC constant region Km(1) | RTVAAPSVFI FPPSDEQLKS GTASVVCLLN NFYPREAKVQ WKVDNVLQSG<br>NSQESVTEQD SKDSTYSLSS TLTLSKADYE KHKLYACEVT HQGLSSPVTK<br>SFNRGEC |

SEQUENCE LIST

| SEQ ID NO: | Description | Sequence |
|---|---|---|
| 11 | h38C2-IgG1 LC constant region Km(1, 2) | RTVAAPSVFI FPPSDEQLKS GTASVVCLLN NFYPREAKVQ WKVDNALQSG NSQESVTEQD SKDSTYSLSS TLTLSKADYE KHKLYACEVT HQGLSSPVTK SFNRGEC |
| 12 | h38C2-IgG1 LC constant region Km(3) | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 13 | H38C2 IgG1 HC constant region | AS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 14 | h38C2-IgG2 HC: | AS TKGPSVFPLA PCSRSTSEST AALGCLVKDY FPEPVTVSWN SGALTSGVHT FPAVLQSSGL YSLSSVVTVP SSNFGTQTYT CNVDHKPSNT KVDKTVERKC CVECPPCPAP PVAGPSVFLF PPKPKDTLMI SRTPEVTCVV VDVSHEDPEV QFNWYVDGVE VHNAKTKPRE EQFNSTFRVV SVLTVVHQDW LNGKEYKCKV SNKGLPSSIE KTISKTKGQP REPQVYTLPP SREEMTKNQV SLTCLVKGFY PSDIAVEWES NGQPENNYKT TPPMLDSDGS FFLYSKLTVD KSRWQQGNVF SCSVMHEALH NHYTQKSLSL SPGK |

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including, for example without limitation, scFv, single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9): 1126-1136). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

Two types of human light chain constant regions are known: lambda (CL-λ) and kappa (CL-κ). There are three known CL-κ variants, based on the polymorphisms V/A at position 46 and A/L at position 84 (numbering according to SEQ ID NO:9). The 3 identified CL-κ polymorphisms are Km(1):$V^{46}/L^{84}$ Km(1,2): $A^{46}/L^{84}$, and Km(3)$A^{46}/V^{84}$). Antibodies of the present invention may therefore comprise a constant kappa domain according to any one of SEQ ID NOs:9, 10, 11 or 12, or variants thereof that comprise no more than 5, 4, 3, 2, or 1 amino acid insertions, substitutions or deletions. It is understood by the skilled person that residue $R^1$ of SEQ ID NOs:9, 10, 11 and 12 by some counting methods may be included in the variable domain, and that the constant domains may therefore also be considered as beginning from residue $T^2$ of said sequences.

The term "antigen binding portion" of an antibody, as used herein, refers to one or more fragments of an intact antibody that retain the ability to specifically bind to a given antigen (e.g., target X). Antigen binding functions of an antibody can be performed by fragments of an intact antibody. Examples of binding fragments encompassed within the term "antigen binding portion" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., 1989 Nature 341:544-546), and an isolated complementarity determining region (CDR).

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987). When choosing FR to flank subject CDRs, e.g., when humanizing or optimizing an antibody, FRs from antibodies which contain CDR1 and CDR2 sequences in the same canonical class are preferred. A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modelling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The contents of US2006205670 (U.S. Pat. No. 7521425) are incorporated herein by reference. US2006205670 (U.S. Pat. No. 7521425) describes a number of compositions and techniques directly applicable to the present application, in particular at paragraphs [0153]-[0233], describing antibodies, useful fragments and variants and modifications thereof, combining sites and CDRs, antibody preparation, expression, humanization, amino acid modification, glycosylation, ADCC, CDC, increasing serum half life of antibodies, expression vectors, mammalian host systems, and folding, amongst other elements of antibody technology.

"Combining site", as used herein, (also known as the antibody binding site) refers to the region of the immunoglobulin or Ig domains that combine (or can combine) with the determinant of an appropriate antigen (or a structurally similar protein). The term generally includes the CDRs and the adjacent framework residues that are involved in antigen binding.

"Aldolase antibodies" as used herein, refers to antibodies containing combining site portions that, when unencumbered (for example by conjugation), catalyze an aldol addition reaction between an aliphatic ketone donor and an aldehyde acceptor. Aldolase antibodies are capable of being generated by immunization of an immune-responsive animal with an immunogen that includes a 1,3 diketone hapten of the formula:

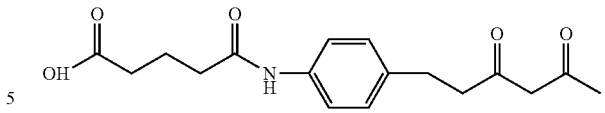

coupled to a carrier protein, and further characterized by having a lysine with a reactive ε-amino group in the combining site of the antibody. Aldolase antibodies are further characterized by their catalytic activity being subject to inhibition with the 1,3-diketone hapten by formation of a complex between the 1,3-diketone hapten and the ε-amino group of the lysine of the catalytic antibody.

As discussed, in certain embodiments, certain antibodies that can be used in conjunction with compounds of the invention may require a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue (e.g. WO 01/22922). The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site. In some embodiments, the amino acid is cysteine, and the reactive group of the side chain is a sulfhydryl group. In other embodiments, the amino acid residue is lysine, and the reactive group of the side chain is the ε-amino group. In some embodiments, the amino acid is Lys93 on the heavy chain according to Kabat numbering. In some embodiments, the amino acid is Lys-99 on HC h38C2 (SEQ ID NO:4).

Catalytic antibodies are one source of antibodies with suitable combining sites that comprise one or more reactive amino acid side chains. Such antibodies include aldolase antibodies, beta lactamase antibodies, esterase antibodies, and amidase antibodies.

One embodiment comprises an aldolase antibody such as the mouse monoclonal antibodies mAb 33F12 and mAb 38C2, as well as suitably chimeric and humanized versions of such antibodies (e.g. h38C2, SEQ ID NOs:3 and 4). Mouse mAb 38C2 (and h38C2) has a reactive lysine near to but outside HCDR3, and is the prototype of a new class of catalytic antibodies that were generated by reactive immunization and mechanistically mimic natural aldolase enzymes. See C. F. Barbas 3$^{rd}$ et al., Science 278:2085-2092 (1997). Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019;

hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases. Aldolase antibodies and methods of generating aldolase antibodies are disclosed in U.S. Pat. Nos. 6,210,938, 6,368,839, 6,326,176, 6,589,766, 5,985,626, and 5,733,75, which are incorporated herein by reference.

Compounds of the invention may also be formed by linking a compound of the invention to a reactive cysteine, such as those found in the combining sites of thioesterase and esterase catalytic antibodies. Suitable thioesterase catalytic antibodies are described by K. D. Janda et al., Proc. Natl. Acad. Sci. U.S.A. 91:2532-2536 (1994). Suitable esterase antibodies are described by P. Wirsching et al., Science 270: 1775-1782 (1995). Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

The antibody may be a humanized antibody. Where compounds of the invention are covalently linked to the combining site of an antibody, and such antibodies are humanized, it is important that such antibodies be humanized with retention of high linking affinity for the Z group. Various forms of humanized murine aldolase antibodies are contemplated. One embodiment uses the humanized aldolase catalytic antibody h38c2 IgG1 or h38c2 Fab with human constant domains $C_K$ and $C_{\gamma1}$1. C. Rader et al., J. Mol. Bio. 332:889-899 (2003) discloses the gene sequences and vectors that may be used to produce h38c2 Fab and h38c2 IgG1. Human germline $V_k$ gene DPK-9 and human $J_k$ gene JK4 were used as frameworks for the humanization of the kappa light chain variable domain of m38c2, and human germline gene DP-47 and human $J_H$ gene JH4 were used as frameworks for the humanization of the heavy chain variable domain of m38c2. FIG. 7A of US2006205670 (herein incorporated by reference) illustrates a sequence alignment between the variable light and heavy chains in m38c2, h38c2, and human germlines. h38c2 may utilize IgG1, IgG2, IgG3, or IgG4 constant domains, including any of the allotypes thereof. In certain embodiments of compounds of the invention wherein the antibody is h38c2 IgG1 with the G1m(f) allotype, Z binds to the side chain of the lysine residue at position 99 of the heavy chain. Another embodiment uses a chimeric antibody comprising the variable domains ($V_L$ and $V_H$) of h38c2 (SEQ ID NOs:5 and 6) and the constant domains from an IgG1, IgG2, IgG3, or IgG4. The antibody may be a full-length antibody, Fab, Fab', $F(ab')_2$, $F_v$, $dsF_v$, $scF_v$, $V_H$, $V_L$, diabody, or minibody. The antibody may be a full length antibody, and may be selected from the group consisting of IgG1, IgG2, $IgG_{2\Delta a}$, IgG3, IgG4, $IgG_{4\Delta b}$, $IgG_{4\Delta c}$, $IgG_4$ S228P, $IgG_{4\Delta b}$ S228P and $IgG_{4\Delta c}$ S228P. The antibody or antigen binding portion thereof may comprise the $V_H$ and $V_L$ domains from h38c2. The antibody may be an antibody comprising the $V_L$ and $V_H$ domains from h38c2 and a constant domain selected from the group consisting of IgG1, IgG2, $IgG_{2\Delta a}$, IgG3, IgG4, $IgG_{4\Delta b}$, $IGg_{4\Delta c}$, $IgG_4$ S228P, $IgG_{4\Delta b}$ S228P and $IgG_{4\Delta c}$ S228P. The antibody may be h38C2 IgG1 (SEQ ID NOs:3 and 4). The antibody may be h38C2 IgG2 (SEQ ID NOs:3 and 14). The antibody may be a humanized version of a murine aldolase antibody comprising a constant region from a human IgG, IgA, IgM, IgD, or IgE antibody. In another embodiment, the antibody is a chimeric antibody comprising the $V_L$ and $V_H$ region from a murine aldolase antibody and a constant region from a human IgG, IgA, IgM, IgD, or IgE antibody. In some embodiments, the antibody comprises the $V_L$ and $V_H$ regions from m38C2 (SEQ ID NOs:7 and 8). In further embodiments, the antibody is a fully human version of a murine aldolase antibody comprising a polypeptide sequence from natural or native human IgG, IgA, IgM, IgD, or IgE antibody. In some aspects, the antibody may comprise a light chain variable region ($V_L$) comprising a $V_L$ CDR1, $V_L$ CDR2, and $V_L$ CDR3 of the $V_L$ sequence shown in SEQ ID NO:5; and a heavy chain variable region ($V_H$) comprising a $V_H$ CDR1, $V_H$ CDR2, and $V_H$ CDR3 of the $V_H$ sequence shown in SEQ ID NO:6. As outlined above, the CDRs may be determined by a number of known methods of the art.

In some aspects, the antibody the antibody comprises a light chain at least 95% identical to SEQ ID NO:3 and a heavy chain at least 95% identical to SEQ ID NO:4. The light chain may be at least 96% identical to SEQ ID NO:3. The light chain may be at least 96% identical to SEQ ID NO:3. The light chain may be at least 97% identical to SEQ ID NO:3. The light chain may be at least 98% identical to SEQ ID NO:3. The light chain may be at least 99% identical to SEQ ID NO:3. The heavy chain may be at least 96% identical to SEQ ID NO:4. The heavy chain may be at least 97% identical to SEQ ID NO:4. The heavy chain may be at least 98% identical to SEQ ID NO:4. The heavy chain may be at least 99% identical to SEQ ID NO:4. In some aspects, the light chain may differ from SEQ ID NO:3 by one amino acid. In some aspects, the heavy chain may differ from SEQ ID NO:4 by one amino acid. In some aspects, the differences between the light chain and SEQ ID NO:3 may be located in the constant region only. In some aspects, the differences between the heavy chain and SEQ ID NO:4 may be located in the constant region only.

In some aspects, the antibodies of the present invention comprise a light chain comprising a light chain constant region comprising a sequence selected from the group consisting of SEQ ID NOs:9, 10, 11, and 12, or variants thereof comprising between 1 and 5 amino acid substitutions, deletions or insertions, and a light chain variable region comprising SEQ ID NO:3.

In some aspects, the antibodies of the present invention comprise a heavy chain comprising a heavy chain constant region comprising a sequence selected from the group consisting of SEQ ID NOs:13, and 14, or variants thereof comprising between 1 and 5 amino acid substitutions, deletions or insertions, and a heavy chain variable region comprising SEQ ID NO:4.

In some aspects, the antibodies of the present invention comprise a light chain constant region comprising a sequence selected from the group consisting of SEQ ID NOs:9, 10, 11, and 12, or variants thereof comprising between 1 and 5 amino acid substitutions, deletions or insertions, and a heavy chain constant region comprising a sequence selected from the group consisting of SEQ ID NOs:13, and 14, or variants thereof comprising between 1 and 5 amino acid substitutions, deletions or insertions. In some aspects, the heavy chain is SEQ ID NO:13, or variants thereof comprising between 1 and 5 amino acid substitutions, deletions or insertions.

Amino acid sequence modification(s) of the antibodies described herein are contemplated. For example, it may be desirable to improve the binding affinity and/or other biological properties of the antibody. Amino acid sequence variants of an antibody are prepared by introducing appropriate nucleotide changes into the antibody nucleic acid, or by peptide synthesis. Such modifications include, for example, deletions from, insertions into, and/or substitutions of residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

An antibody or antibody portion of the invention can be derivatized or linked to another molecule (e.g. another peptide or protein). In general, the antibodies or portion thereof is derivatized such that the ability of the linker to covalently conjugate to the antibody combining is not affected adversely by the derivatization or labelling. Accordingly, the antibodies and antibody portions of the invention are intended to include both intact and modified forms of the antibodies described herein. E.g. an antibody or antibody portion of the invention can be functionally linked (by chemical coupling, genetic fusion, noncovalent association or otherwise) to one or more other molecular entities, such as another antibody (e.g. a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

In other embodiments, the antibody or antigen binding portion thereof of the invention may be a fusion antibody or an antibody linked to another polypeptide. In some aspects, only the variable regions of the antibody are linked to the polypeptide. In some aspects, the antibody is covalently conjugated to a peptide in such a way so as to not interfere with the binding ability of the combining site.

The polypeptide may be a therapeutic agent, such as a targeting agent, peptide, protein agonist, protein antagonist, metabolic regulator, hormone, toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody. By "peptide", it is understood that the term encompasses chains of amino acids commonly referred to as peptides, polypeptides and proteins. In some aspects, the peptide is at least three amino acids in length. In some aspects, the peptide is less than about 500 amino acids in length. In some aspects, the peptide is less than about 300 amino acids in length. In some aspects, the peptide is less than about 200 amino acids in length. In some aspects, the peptide is less than about 150 amino acids in length. In some aspects, the peptide is less than about 100 amino acids in length. In some aspects, the peptide is less than about 80 amino acids in length. In some aspects, the peptide is less than about 70 amino acids in length. In some aspects, the peptide is less than about 60 amino acids in length. In some aspects, the peptide is less than about 50 amino acids in length. In some aspects, the peptide is less than about 40 amino acids in length.

One type of derivatized antibody is produced by crosslinking two or more antibodies (of the same type or of different types, e.g. to create bispecific antibodies). Suitable crosslinkers include those that are heterobifunctional, having two distinctly reactive groups separated by an appropriate spacer (e.g. m-maleimidobenzoyl-N-hydroxysuccinimide ester) or homobifunctional (e.g. disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. When an antibody is labelled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labelled with biotin, and detected through indirect measurement of avidin or streptavidin binding. An antibody may be labelled with a magnetic agent, such as gadolinium. An antibody may also be labelled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The antibody may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding. In some aspects, antibodies of the invention relate to h38C2. In some aspects, h38C2 comprises SEQ ID NO:3 and 4 and variants thereof. In this context, "variants thereof" relates to antibodies that comprise a light chain variable region ($V_L$) comprising a $V_L$ CDR1, $V_L$ CDR2, and $V_L$ CDR3 of the $V_L$ sequence shown in SEQ ID NO:5; and a heavy chain variable region ($V_H$) comprising a $V_H$ CDR1, $V_H$ CDR2, and $V_H$ CDR3 of the $V_H$ sequence shown in SEQ ID NO:6. Preferably, the h38C2 is an IgG1 antibody. Preferably the h38C2 variant comprises the $V_L$ as set forth in SEQ ID NO:5 and the $V_H$ as set forth in SEQ ID NO:6, and further comprises a light chain constant region at least 95% identical to one or more of SEQ ID NOs:9, 10, 11 and 12, and a heavy chain constant region at least 95% identical to SEQ ID NO:13. In some aspects, the identity of each constant chain independently to one of SEQ ID NO:12 or 13 may be at least 96%, at least 97%, at least 98% or at least 99%. In some aspects, the light chain constant region differs by no more than 5 amino acid residues from one or more of SEQ ID NOs:9, 10, 11 and 12. In some aspects, the light chain constant region comprises SEQ ID NO:12. In some aspects, the light chain constant region differs by no more than 5, 4, 3, 2, or 1 amino acid from SEQ ID NO:12.

EXAMPLES

The versatility of the invention is illustrated by the following Examples, which illustrate typical embodiments of the invention and are not limiting of the claims or specification in any way.

Example 1

Summary of Experimental Conditions for the Preparation of Compound 13

Several routes to generate 13 were explored. In the past, KF on alumina has been employed in several types of transformations to promote a slow deprotonation of the azetidinone, but low conversion to 13 was observed over a 3-day period when this approach was tried (data not shown).

Experimental Conditions
1. A first route to generate 13 employed Cl₂SO to make the acid chloride 10 and n-BuLi to deprotonate azetidinone 11. In a first flask, acid 9 was treated with Cl₂SO to prepare acid chloride 10. Upon reaction completion, excess Cl₂SO was removed by distillation and the acid chloride was dissolved in THF. In a second flask azetidinone 11 was treated with n-BuLi in THF at the specified temperature. The acid chloride solution prepared in the first flask was added to the second flask and the mixture warmed to RT. After aqueous workup, the product was purified by chromatography.
2. The second route to generate 13 employed (COCl)₂ to make the acid chloride 10 and LiHMDS to deprotonate azetidinone 11. A similar protocol was employed as for the first route, above.
3. The third route explored used CDI/DIPEA. CU was added to a solution of acid 9 in CH₂Cl₂. After 1 hr at RT, 2-azetidinone (11) was added and the mixture is stirred at RT for the desired amount of time.
4. The fourth route explored was a combination of T3P and DIPEA. To a solution of acid 9,2-azetidinone 11, and DIPEA in a suitable solvent was added a 50% solution of T3P in EtOAc. The mixture was stirred at the desired temperature for the specified amount of time. Upon reaction completion, an aqueous workup was performed and compound 13 was purified by recrystallization from a suitable solvent.

The best results were obtained from the fourth route, using DIPEA/T3P.

Example 2

Synthesis of 13

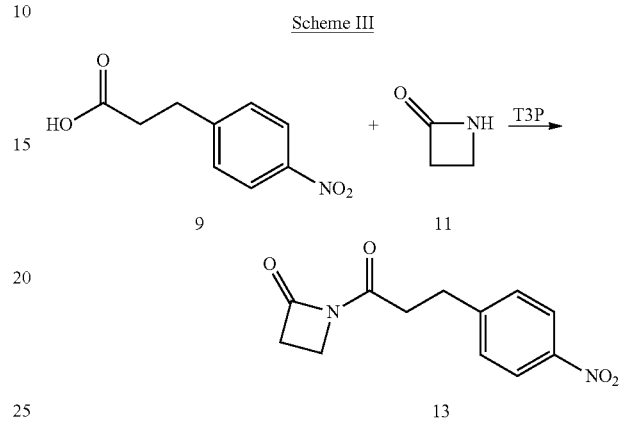

Scheme III

TABLE 1

Summary of experimental conditions for the coupling of acid 9 with 2-azetidinone (11).

| | Equiv 11 | Base (Equiv) | Other reagents (Equiv) | Temp. (° C.) | Solvent | Reaction time (h) | Yield (%) |
|---|---|---|---|---|---|---|---|
| 1 | 1.2 | BuLi (1.3) | Cl₂SO (5), | −70 to 0 | THF | 2 | 2 |
| 1 | 0.85 | BuLi (1.3) | Cl₂SO (5) | −70 to 0 | THF | 2 | 55 |
| 2 | 1.2 | LiHMDS (1.1) | (COCl)₂ (2) | −30 to 0 | THF | 18 | 17 |
| 3 | 1.2 | DIPEA (1) | CDI (1.05 equiv) | RT | CH₂Cl₂ | 1 | 0 |
| 4 | 1.2 | TEA (5) | T3P (1.5 equiv) | RT | THF | 1 | 0 |
| 4 | 1.2 | pyridine (7) | T3P (2 equiv) | 0 | DMF | 1 | 0 |
| 4 | 1.2 | DIPEA (5) | T3P (1 equiv) | 0 | DMF | 18 | 59 (IPA recryst) |
| 4 | 1.2 | DIPEA (5) | T3P (1 equiv) | 0 | MeCN | 18 | 31 (IPA recryst) |
| 4 | 1.5 | DIPEA (5) | T3P (1 equiv) | 2 h @ 0-5, then 18 h RT | MeCN | 20 | 40 (hexanes/IPA recryst) |
| 4 | 1.35 | DIPEA (3) | T3P (1 equiv) | RT | MeCN | 18 | 46 (IPA recryst) |
| 4 | 1.2 | DIPEA (5) | T3P (1 equiv) | RT | MeCN | 18 | 39 (IPA recryst) |
| 4 | 1.5 | DIPEA (5) | T3P (1.5 equiv) | RT | MeCN | 3.5 | 55 (IPA recryst) |
| 4 | 1.5 | DIPEA (5) | T3P (1.5 equiv) | RT | MeCN | 2 | 59-65 (IPA recryst) |

It was found that the preparation of acid chloride 10 using Cl₂SO or oxalyl chloride and the subsequent reaction with the anion of 2-azetidinone prepared via deprotonation with BuLi or LiHMDS led to the desired product 13 but generally gave low yield and purity.

The activation of acid 9 with CU was readily achieved, but the subsequent coupling with 2-azetidinone or its anion failed in solvents such as CH₂Cl₂, THF, and EtOAc, most likely due to the low nucleophilicity of this substrate.

To a solution of 3-(4-nitrophenyl)propanoic acid (9, 440 g, 2.25 mol), 2-azetidinone (11, 240 g, 3.37 mol), and DIPEA (1.46 kg, 11.3 mol) in MeCN (4.4 L) was added a 50% (wt/wt) solution of 1-propanephosphonic acid anhydride (T3P) in EtOAc (2.15 kg, 3.38 mol) over 1 hr while the internal temperature was held at 20-25° C. After the resulting mixture had been stirred at 22° C. for 20 hrs, HPLC analysis showed 0.9% of unreacted 9.

The reaction was concentrated under reduced pressure to about 2 L and the residue was taken up in i-PrOAc (6.6 L) at 30-35° C. The organic layer was washed with 10% aqueous citric acid (4 L). The aqueous layer was back-extracted with i-PrOAc (2.7 L) and to the combined organic extracts was added Darco G-60 (90 g). The mixture was stirred at 25° C. for 4 hrs and filtered through celite. The celite filter was washed with i-PrOAc (0.5 L) and the filtrates were concentrated under reduced pressure to about 1 L. 2-Propanol (2.2 L) was added and the distillation was resumed to a final volume of about 1 L. 2-Propanol (2.2 L) was added and the mixture was cooled to 3° C. and held at this temperature for 1 hr. The solid was filtered and washed with 2-propanol (0.55 L). The wet cake was transferred back to the reactor and dissolved in EtOAc (3.24 L). Darco G-60 (90 g) was added and the mixture was stirred at 25° C. for 2 hrs. The suspension was filtered through celite and the celite pad was washed with EtOAc (0.5 L). The filtrates were concentrated under reduced pressure to about 1 L and 2-propanol (1.4 L) was added. The solution was concentrated to about 1 L and additional 2-propanol (1.4 L) was added. The suspension was cooled to 3° C. and held at this temperature for 1 hr. The solid was filtered, washed with 2-propanol (0.5 L), and dried at 30-35° C. under vacuum for 8 hrs to give 273 g (49%) of 13.

HPLC retention time: 2.68 min. HPLC purity: 98.0% (a/a). Mp: 104-106° C. $^1$H NMR (400 MHz, DMSO-$d_6$) δ ppm 2.88-3.05 (m, 6 H) 3.42 (t, J=5.27 Hz, 2 H) 7.44-7.53 (m, 2 H) 8.07-8.16 (m, 2 H). $^{13}$C NMR (100 MHz, DMSO-$d_6$) δ ppm 29.37, 36.05, 36.89, 37.00, 123.83, 130.06, 146.38, 149.49, 166.20, 169.38. MS (ES+): 249 (M+H)$^+$.

Example 3

Synthesis of 14b

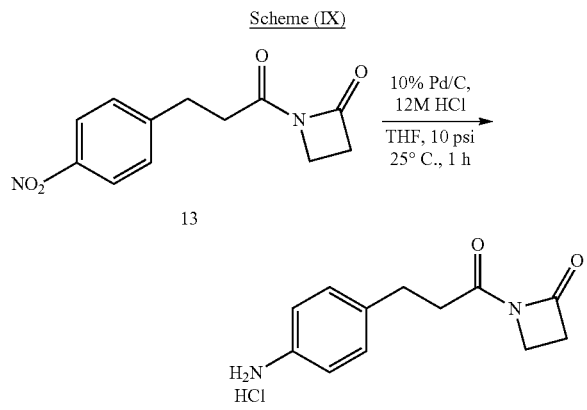

One hypothesis explored was that it was necessary to isolate compound 14 as a solid, in order facilitate long term storage. Accordingly, an improved process was devised for the generation of a salt form of compound 14; compound 14b. To a 1-L Atlantis reactor was added 10% palladium on carbon (Pd/C) (50.00 mg), THF (11.00 mL), and compound 13 (0.5 g). The reactor was sealed and hydrogenated at 10 psi and 25° C. for 1 hr. HPLC indicates complete reaction. The catalyst was removed by filtration. Compound 14 was isolated as a solution. HPLC purity >99%.

Formation and Isolation of HCl Salt:

A 190 mL solution from the nitro reduction carried out by containing the free base compound 14 (5.85 g) was cooled to 0-5° C. HCl (12 M, 1.5 mL) was added to give a yellowish suspension. The slurry was concentrated under vacuum to ~60 mL. Isopropyl acetate (117 mL) was added over 30 min. The slurry was reconcentrated under vacuum to a final volume of 60 mL. The slurry was granulated for 30 min at 0-5° C. and then filtered. The solids were dried in vacuum oven at 40° C. overnight to give 6.6 g of HCl salt 14b.

While an improvement over the previous process, the above method has the disadvantages of still being relatively time and resource consuming. Accordingly, the counterintuitive decision was made to isolate compound 14 as a free base, despite the potential disadvantages of stability of the compound in solution, and the likely concomitant requirement to use the solution immediately.

Example 4

Summary of Conditions for Preparation of Compound 14

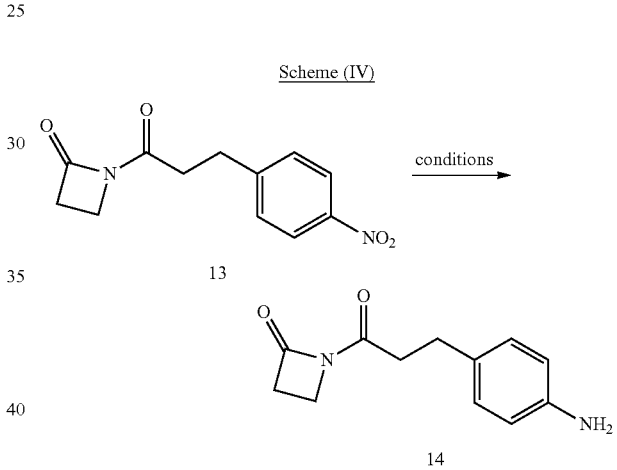

Compound 13 was dissolved in THF and 10% Pd/C added. The reaction was then hydrogenated at 10 psig for 16 hrs at about 25° C. Upon reaction completion, the catalyst was filtered off and the filtrates containing aniline 14 used in the next step (coupling with diglycolic anhydride 15). In assays, altering the volume of THF (e.g. from about 20 to about 60 volumes) or the reaction time (e.g. from about 1 to about 16 hours) did not alter the yield or purity of the reaction; accordingly these variables were determined to be discretionary.

Example 5

Activated Carbon Screen

10% wt equivalent of 10% palladium and carbon were charged dry under nitrogen to a reactor followed by a solution of starting material in 10 volumes of tetrahydrofuran. A portion of additive was added to each and hydrogenated at 50 psi at RT overnight. The complete reaction was filtered to remove the catalyst and the resulting filtrate analyzed for undesired side products. The results from the carbon screen are shown in Table 2.

TABLE 2

Levels of impurity 16 after carbon treatment screen.

| Carbon | Recovery | % of 16 by HPLC |
| --- | --- | --- |
| CGSP | 82% | 0.2438 |
| SX-Plus | 91% | 0.6257 |
| Darco S-51HF | 93% | 0.44 |
| E Supra USP | 91% | 0.3332 |
| SX-Ultra | 91% | 0.3585 |
| CASP | 92% | 0.5264 |
| Darco G-60 | 90% | 0.2633 |

Example 6

Summary of Reaction Conditions for Preparing Compound 6

To a solution of compound 14 in the corresponding solvent is added diglycolic anhydride (15). A base such as DIPEA can be added but it is not necessary. The reaction is stirred for the specified amount of time at the desired temperature. After an aqueous workup, the crude material is purified via slurry in a suitable solvent.

TABLE 3

Summary of experimental conditions for the coupling of aniline 14 with diglycolic anhydride (15) to produce 6, using 1 equiv of 15, at RT.

| Base | Solvent | Reaction time (h) | Yield (%) |
| --- | --- | --- | --- |
| DIPEA (1.1 equiv) | CH$_2$Cl$_2$ | 2 | 68% (hexanes trituration) |
| DIPEA (1.1 equiv) | CH$_2$Cl$_2$ | 2 | 50% (IPA trituration) |
| No base | THF | 0.5 | 57-64% (IPA trituration) |
| No base | THF | 0.5 | 74-94% (MeOAc trituration) |

Example 7

Selection of 7$^{th}$ Solvent

An equal amount of compounds 14 (free base) and 15 were dissolved in 20 volumes of THF (20 mL/g of 14). The mixture was stirred at RT until reaction completion (about 30 min). The solvent was removed under reduced pressure and the solid residue was triturated in 5 volumes of 7$^{th}$ solvent (one of hexane, 2-propanol, methyl acetate or i-propyl acetate). The solids were filtered and dried, and assessed for yield and purity (Table 5). Use of hexane gave a 68% yield of 97% purity. Use of 2-propanol gave only a 50% yield. Use of methyl acetate gave an 80% yield of 96.8% purity. Use of i-propyl acetate gave an 80% yield of approximately 95.5% purity.

Example 8

Synthesis of compound 6

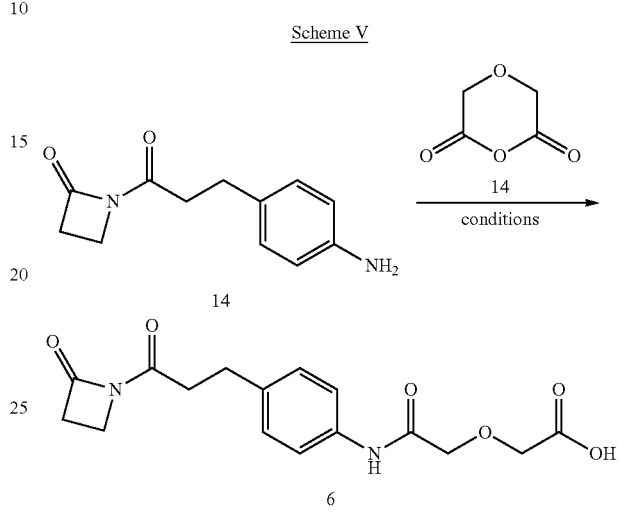

Scheme V

A 30-L hydrogenation reactor was charged with nitro compound 13 (142 g, 0.57 mol), 10% Pd/C (14 g), and THF (8.52 L). Stirring was started and the mixture was hydrogenated at 10 psig and 25° C. for 1 hr. After HPLC analysis showed complete consumption of the starting material, the mixture was filtered through a celite-precoated 0.5-micron cartridge filter and the filter was washed with THF (3 L). The filtrates containing aniline 14 were transferred to a 20-L jacketed reactor and diglycolic anhydride (15, 75 g, 0.65 mol) was added. After 15 min at 22° C., HPLC analysis of the mixture showed complete consumption of 14 and the reaction was concentrated to 2 L under reduced pressure. The residue was seeded with a small amount of acid 6 crystals (1.06 g) and, after 15 min, i-PrOAc (1.78 L) was added over a 1-h period. The suspension was concentrated under reduced pressure to 1.5 L and the residue was cooled to 3° C. After 1 hr, the solid was filtered, washed with cold i-PrOAc (0.5 L) and dried under vacuum at 40° C. to give 160 g (84%) of acid 6. Analysis showed residual THF (0.60% wt/wt) and i-PrOAc (0.62% wt/wt).

This material was reworked as follows to improve color and reduce the amount of residual solvent. Acid 6 (150 g, 0.45 mol) was dissolved in THF (5.25 L) at 30° C. Activated carbon Darco KBB (30 g) was added and the mixture was stirred for 1 hr at this temperature. The suspension was filtered through celite and the celite pad was washed with THF (0.5 L). The filtrates were concentrated under reduced pressure to 1.5 L and to the residue was added i-PrOAc (3 L) over 30 min. The mixture was held at RT (e.g. about 20° C.) for 2 hrs and it was then concentrated under reduced pressure to 1.5 L. The suspension was cooled to 3° C., stirred for 1 hr, and filtered. The solid was washed with i-PrOAc (80 mL) and dried under vacuum at 40° C. for 12 hrs to give 120 g (80% yield) of 6.

Analysis showed residual THF (0.13% wt/wt) and i-PrOAc (0.27% wt/wt). HPLC retention time: 2.18 min. HPLC purity: 99.3% (a/a). Mp: 139-140° C. $^1$H NMR (400 MHz, DMSO-d$_6$) δ ppm 2.72-2.90 (m, 4H) 3.00 (t, J=5.27 Hz, 2H) 3.38-3.42 (m, 2 H) 3.43 (s, 1 H) 4.12 (s, 2 H) 4.16 (s, 2 H) 7.10-7.16 (m, 2 H) 7.47-7.53 (m, 2 H) 9.77 (s, 1 H) 12.84 (br. s., 1 H). $^{13}$C NMR (100 MHz, DMSO-d$_6$) δ ppm 29.16, 35.98, 36.84, 37.89, 68.54, 70.89, 120.09, 128.95, 136.24, 136.84, 166.20, 168.10. MS (ES+): 335 (M+H)$^+$.

Example 9

Preparation of Compound 6 from Compounds 9 and 11

Scheme X

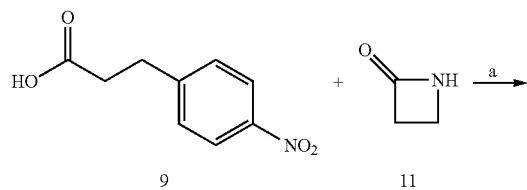

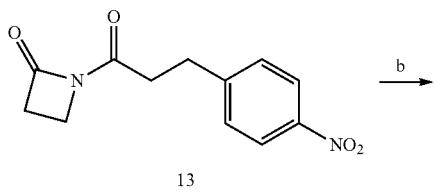

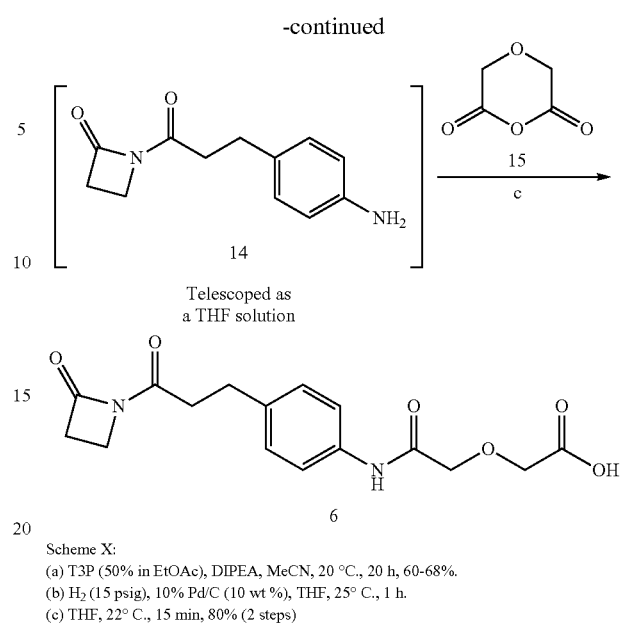

Scheme X:
(a) T3P (50% in EtOAc), DIPEA, MeCN, 20 °C., 20 h, 60-68%.
(b) H$_2$ (15 psig), 10% Pd/C (10 wt %), THF, 25° C., 1 h.
(c) THF, 22° C., 15 min, 80% (2 steps)

Example 10

Summary of Conditions for Preparation of Compound 20

Acid 6 and pentafluorophenol (19) were dissolved in the corresponding solvent. The coupling agent was added and the reaction stirred for the specified amount of time at the desired temperature. After an aqueous workup, crude 20 was purified by either chromatography or slurry in a suitable solvent.

TABLE 4

Summary of experimental conditions for the coupling of acid 6 with pentafluorophenol (19).

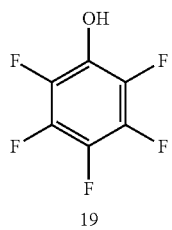

19

| Equivalents | Coupling reagent | Temp. (° C.) | Solvent | Reaction time (h) | Yield (%) |
|---|---|---|---|---|---|
| 1.1 | EDC·HCl (1.1 equiv) | 0 to rt | CH$_2$Cl$_2$ | 18 | 77% (IPA slurry) |
| 1 | EDC·HCl (1.2 equiv) | 0 to rt | DMF | 18 | 62% (IPA slurry) |
| 1.1 | DCC (1.05 equiv) | 0 to rt | THF | 18 | 65% (after chromatography) |
| 1.1 | DCC (1.05 equiv) | 0 to rt | THF | 18 | 79% (IPA slurry) |

Example 11

Synthesis of Pentafluorophenol Ester 20

Scheme VI

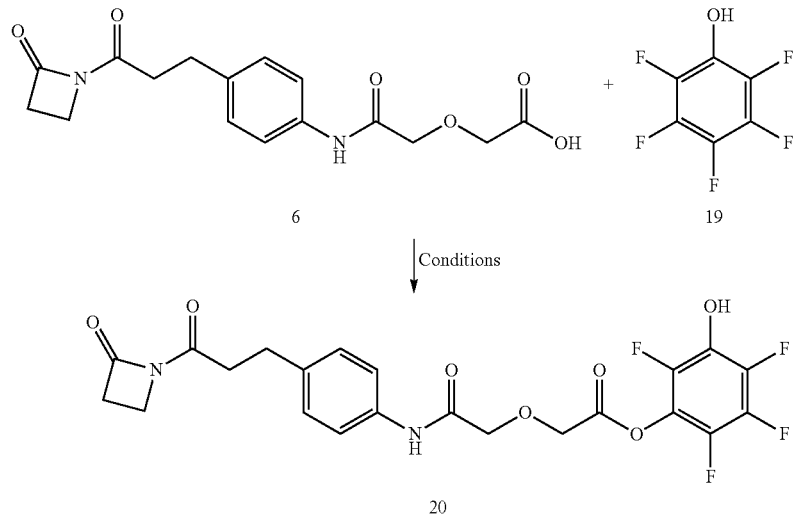

Scheme VI Conditions: DCC, THF, 0° C. to RT, 18 hr, 80-85% yield.

To a cold (3-5° C.) solution of acid 6 (80 g, 239 mmol) and pentafluorophenol (19, 49 g, 266 mmol) in THF (1.1 L) was added a solution of N,N'-dicyclohexylcarbodiimide (52 g, 252 mmol) in THF (400 mL) over 10 min. After 15 min, the mixture was warmed to 22° C. and stirred for 18 hr. HPLC analysis showed complete reaction. The suspension was filtered to remove the dicyclohexylurea byproduct and the solid was washed with THF (110 mL). The filtrates were concentrated to about 1.8 L and acetone (1.58 L) was added. The suspension was cooled to 10° C. and stirred for 1.5 hr. The remaining dicyclohexylurea was filtered off and the solid was washed with acetone (25 mL). The filtrates were concentrated to about 1.8 L and 2-propanol (2.75 L) was added. The slurry was stirred at RT (e.g. about 20° C.) for 16 hr and the solid was filtered, washed with 2-propanol (110 mL) and dried under vacuum at 40° C. for 16 hr to give 95 g (83%) of pentafluorophenol ester 20 as a white solid.

HPLC retention time: 3.25 min. HPLC purity: 96.6%. Mp: 94-99° C. $^1$H NMR (400 MHz, CDCl$_3$) δ ppm 2.85-3.07 (m, 7 H) 3.53 (t, J=5.27 Hz, 2 H) 4.26 (s, 2 H) 4.62 (s, 2 H) 7.10-7.22 (m, 2 H) 7.40-7.53 (m, 2 H) 8.47 (s, 1 H). $^{13}$C NMR (100 MHz, CDCl$_3$) δ ppm 29.37, 35.83, 36.50, 37.98, 67.89, 69.03, 71.46, 71.83, 120.08, 120.16, 128.97, 128.08, 135.07, 136.87, 165.03, 166.13, 166.24, 170.10. MS (ES+): 501 (M+H)$^+$.

Example 12 Experimental Conditions for Preparation of Compound 3

The peptide 2a (SEQ ID NO:1) was dissolved in a suitable solvent and the temperature of the resulting solution was adjusted to the desired value. Pentafluoro ester 20 and base were added and the reaction stirred for the specified amount of time at the desired temperature. If an anti-solvent was employed to precipitate product 3 from solution, the anti-solvent was added at the same temperature that the coupling between 2 and 20 is run. The mixture was then allowed to warm to RT and stirred for 1 hr. Product 3 was the isolated by filtration.

TABLE 5

Summary of experimental conditions for the coupling of peptide 2 with pentafluoro ester 20.

| 20 (equiv) | Base (equiv.) | Solvent (volumes) | Anti-solvent (Vol) | Temp. (° C.) | Reaction time (h) | Yield (%) | Comments |
|---|---|---|---|---|---|---|---|
| 3 | NMM (20) | DMF (20) | MTBE | 20 | 0.3 | Not isolated | High level of impurities |
| 3 | NMM (20) | NMP (20) | MTBE | 20 | 0.3 | Not isolated | High level of impurities |
| 3 | DIPEA (20) | DMF (20) | MTBE | 20 | 0.3 | Not isolated | High level of impurities |
| 3 | DIPEA(20) | NMP (20) | MTBE | 20 | 0.3 | Not isolated | High level of impurities |
| 1 | NMM (20) | DMF (20) | MTBE | 20 | 0.3 | Not isolated | Product oiled out |

TABLE 5-continued

Summary of experimental conditions for the coupling of peptide 2 with pentafluoro ester 20.

| 20 (equiv) | Base (equiv.) | Solvent (volumes) | Anti-solvent (Vol) | Temp. (° C.) | Reaction time (h) | Yield (%) | Comments |
|---|---|---|---|---|---|---|---|
| 1.2 | NMM (20) | DMF (20) | EtOAc | 20 | 0.3 | Not isolated | Product oiled out |
| 1.5 | NMM (20) | DMF (20) | THF | 20 | 0.3 | Not isolated | Product oiled out |
| 1 | NMM (20) | NMP (20) | MTBE | 20 | 0.3 | Not isolated | Product oiled out |
| 1.2 | NMM (20) | NMP (20) | EtOAc | 20 | 0.3 | Not isolated | Product oiled out |
| 1.5 | NMM (20) | NMP (20) | THF | 20 | 0.3 | Not isolated | Product oiled out |
| 2 | NMM (20) | DMF (20) | MTBE | 20 | 0.3 | Not isolated | HPLC purity: 78% |
| 3 | NMM (20) | DMF (20) | MTBE | 20 | 0.3 | Not isolated | HPLC purity: 84% |
| 3 | NMM (20) | MeOH (40) |  | 20 |  |  | No desired product detected |
| 3 | NMM (20) | MeCN (40) |  | 20 |  |  | No desired product detected |
| 4 | NMM (20) | DMSO | 2-MeTHF (80) | 20 | 1 | Not isolated | HPLC purity: 88% |
| 4 | NMM (20) | DMF | 2-MeTHF (80) | 20 | 1 | Not isolated | HPLC purity: 94% |
| 4 | NMM (20) | DMAc | 2-MeTHF (80) | 20 | 1 | Not isolated | HPLC purity: 90% |
| 4 | NMM (1) | DMF (13)/MeCN (13) |  | 20 | 2 |  | Incomplete reaction |
| 4 | NMM (1.3) | DMF (13)/MeCN (13) |  | 20 | 2 |  | Incomplete reaction |
| 4 | NMM (1.5) | DMF (13)/MeCN (13) |  | 20 | 2 |  | Incomplete reaction |
| 5 | NMM (1) | DMF (13)/MeCN (13) |  | 20 | 2 |  | Incomplete reaction |
| 5 | NMM (1.3) | DMF (13)/MeCN (13) |  | 20 | 2 |  | Incomplete reaction |
| 5 | NMM (1.5) | DMF (13)/MeCN (13) |  | 20 | 2 |  | Incomplete reaction |
| 4 | NMM (1.5) | DMF (26) | MeCN (9) | 20 | 0.5 | 80% | HPLC purity: 99.2% |
| 4 | NMM (1.5) | DMF (15) | MeCN (9) | 20 | 0.5 | 81% | HPLC purity: 92% due to presence of pentafluroester byproducts not detected with previous HPLC method |
| 2 | NMM (1.5) | DMF (15) |  | 0 | 0.5 | Not isolated | Pentafluorester impurities level below 3% |
| 3 | NMM (1.5) | DMF (15) |  | 16 | 0.5 | Not isolated | Pentafluorester impurities level: 6% |
| 1.2 | NMM (1.5) | DMF (15) |  | −20 | 2 | Not isolated | Pentafluorester impurities level < 1% but incomplete reaction |
| 1.5 | NMM (1.5) | DMF (15) |  | −20 | 2 | Not isolated | Pentafluorester impurities level < 1% but incomplete reaction |
| 2 | NMM (1.5) | DMF 15 |  | −20 | 2 | Not isolated | Pentafluorester impurities level < 1% but incomplete reaction |

TABLE 5-continued

Summary of experimental conditions for the coupling of peptide 2 with pentafluoro ester 20.

| 20 (equiv) | Base (equiv.) | Solvent (volumes) | Anti-solvent (Vol) | Temp. (°C.) | Reaction time (h) | Yield (%) | Comments |
|---|---|---|---|---|---|---|---|
| 1.5 | NMM (1.5) | DMF (15) |  | −20 | 8 | Not isolated | Incomplete reaction |
| 3 | NMM (1.5) | DMF (15) |  | −20 | 4 | Not isolated | Complete reaction. Pentafluorester impurities level: 2.2% |
| 4 | NMM (1.5) | DMF (15) |  | −20 | 5 | Not isolated | Complete reaction. Pentafluorester impurities level: 3.7% |
| 3 | NMM (1.5) | DMF (15) | MeCN (144) | −15 | 4.5 | 79 | Final conditions. Unreacted starting material: 1.96%. HPLC purity: 97%. Pentafluorester impurities level: 1.19% |

Example 13

Synthesis of Peptide-Linker Conjugate 3

To a cold (−15° C.) solution of peptide 2 (100 g, 35.2 mmol) in DMF (0.95 L) was added NMM (4.8 mL, 43.6 mmol) followed by pentafluorophenol ester 20 (50 g, 100 mmol) in small portions over 5 min. The mixture was stirred at −15° C. for 7 hrs at which point HPLC analysis showed less than 1% of unreacted 2. The mixture was filtered through a 0.45 micron in-line filter and added to a second reactor containing MeCN (12.8 L) at RT (e.g. about 20° C.) over 5 min. A white precipitate formed immediately. The first reactor was washed with DMF (100 mL) and this wash was added to the second reactor through the in-line filter. The slurry was stirred at RT (e.g. about 20° C.) for about 1 hr and the solid was filtered, washed with MeCN (3×1 L), and dried under vacuum at RT (e.g. about 20° C.) for 6 hr to give 94 g (86%) of 3 as a white solid. GC headspace showed residual DMF (4.5% wt/wt) and MeCN (0.95% wt/wt). With the goal of reducing solvent content to meet specifications, the solid was passed through a #20 hand-sieve and then slurried in MeCN (10 L) at about RT for 1 hr with good agitation. The solid was filtered, washed with MeCN (2×1 L) and dried at 30° C. for 24 hrs and at 40° C. for an additional 24 hrs to give 91 g of 3 (97% recovery, 83% overall yield). Residual DMF (0.05% wt/wt) and MeCN (0.19% wt/wt). HPLC purity: 96.5% (a/a). HPLC retention time: 17.99 min. MS (ES+): 3156.6 Da $(M+H)^+$.

Scheme VII: Final conjugation and isolation conditions for peptide-linker conjugate 3.

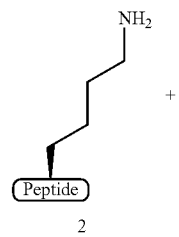

2

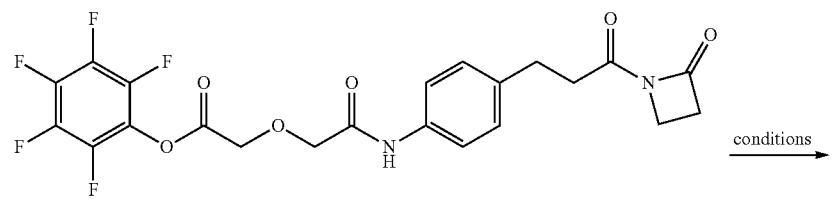

20
(3 equiv)

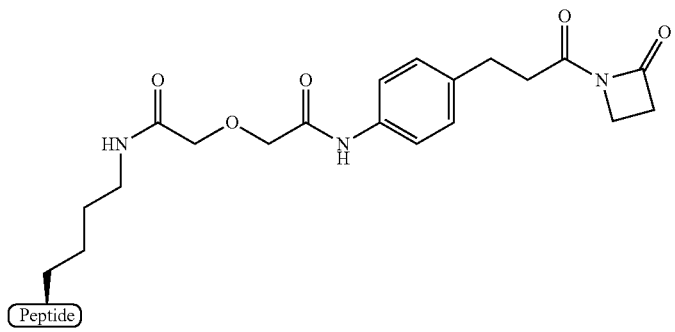

3

Conditions: NMM (1.3 equiv), DMF (15 vol), −15 to −18° C., 7 h. Filtration to remove insolubles (0.45 micron). Drip in filtrates into MeCN (~144 vol) to precipitate product. Final composition: MeCN/DMF 9/1. Wash filter with DMF (1 vol). Stir at RT for 1-2 hrs. Filter under $N_2$. Wash cake with 100% MeCN (3×10 vol). Dry at RT (e.g. about 20° C.). Reslurry in MeCN (100 vol) to remove residual DMF. Dry 1 at 40° C. under vacuum Yield: 83%.

Example 14

Conjugation of Acid 6 with Peptide 2 to Form Conjugate 3

Acid 6 was originally activated as its N-hydroxysuccinimido ester prior to coupling with peptide 2. This approach was explored by treating acid 6 with N-hydroxysuccinimide (7) using N,N'-dicyclohexylcarbodiimide (DCC) as coupling reagent to generate intermediate 8. It proved difficult to isolate intermediate 8 by crystallization.

In addition, efforts to isolate intermediate 8 by chromatography on silica demonstrated signs of instability of intermediate 8 when in contact with silica were observed by TLC analysis.

Even though 8 was isolated as a foamy solid in an excellent 92% yield after chromatography, both HPLC and $^1$H NMR analyses showed a mixture of two major components. One of them was identified as desired 8 but increasing amounts of the second component were noticed after the solid had been set aside for only a few hours.

Further investigation resulted in the identification of morpholine-3,5-dione 18 as the second component by LC-MS, which formed via intramolecular displacement of the N-hydroxysuccinimido group by the anilide nitrogen on the molecule.

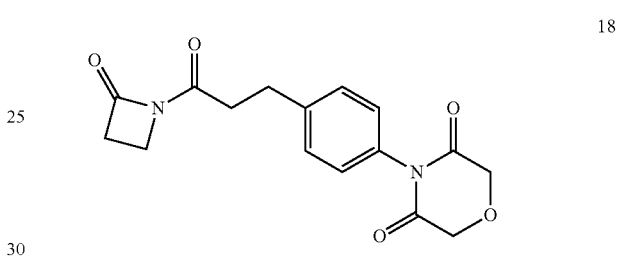

18

This cyclic byproduct became the major constituent of the isolated solid after only a few days at RT. Since this side-reaction was envisioned to become even more problematic on scale due to the longer timelines for processing and isolation, a search for an alternative activating group for acid 6 was undertaken.

Based on the information obtained from experimentation related to the N-hydroxysuccinimido ester, it became clear that a fine balance between reactivity toward the amino group on the lysine residue of peptide 2 and stability to prevent morpholine-3,5-dione 18 formation was necessary.

Example 15

Improving the Impurity Profile

The reaction between peptide 2 and compound 20 was very fast (<30 min) when run at RT (e.g. about 20° C.) and the purities of the isolated material were in the 90-95% range. Up to 4 major impurities were detected that caused a drop in purity compared to the purity of the peptide 2 starting material.

These 4 byproducts were characterized as pentafluorophenol ester derivatives of peptide-linker conjugate 3 based on MS data (all of them displayed the same mass) and, when combined together, they amounted to 7-8%. Interestingly, each impurity is a distinct monoester corresponding to the four different carboxylic acid groups on the peptide backbone and no impurities with multiple esters were detected. Therefore, it appears that once a pentafluorophenol monoester derivative forms, further esterification on that same molecule is extremely slow. The structures of these impurities are shown below.

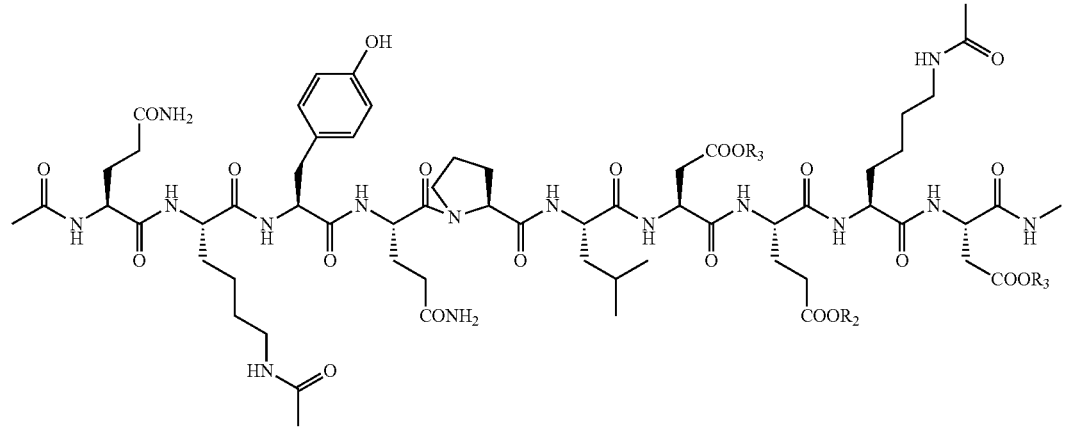

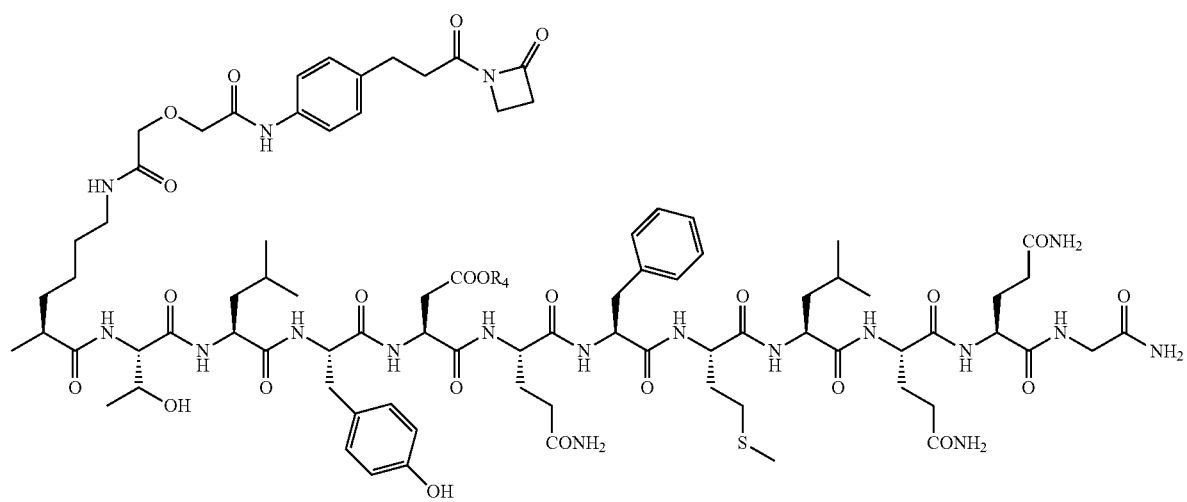

$R_1, R_2, R_3, R_4 = H$ or $C_6F_5$

This fact is difficult to rationalize based on the existing physical separation between the acid groups. It was therefore desirable to minimize their presence in order to obtain ≥95% purity specification for peptide-linker conjugate 3. A major driving force for this was that any attempts to upgrade the chemical purity of peptide-linker conjugate 3 by trituration or recrystallization had failed due to the extremely low solubility of peptide-linker conjugate 3 and related byproducts.

A final study was carried out to determine the stability of the pentafluorophenol ester impurities that were identified during the peptide-linker conjugation reaction. It was reasoned that these byproducts would also couple to the monoclonal antibody during the final process to prepare the drug substance and might complicate the final purification of 5. As a result, a sample of peptide-linker conjugate 3 with high pentafluorophenol ester impurities levels was placed in the same 50:50 20 mM histidine/propylene glycol buffer at pH 6.5 that is employed to conjugate peptide-linker 3 with monoclonal antibody 4. The results are shown in Table 6. After only 30 min, one of the three impurities was not detectable and the levels of the other two had decreased considerably. At the same time, the overall purity had increased by about the same amount. After 60 min, the remaining 2 had almost completely vanished and the purity of 3 stayed unchanged. This result seems to indicate that these impurities are short-lived in this aqueous medium and revert back to the desired product 3.

TABLE 6

Pentafluorophenol ester impurities time-dependent stability study in 50:50 20 mM histidine/propylene glycol buffer at pH 6.5.

| | Time point (Minutes) | | | | |
|---|---|---|---|---|---|
| | 0 | 30 | 60 | 90 | 120 |
| Purity (1, %) | 95.6 | 96.5 | 96.5 | 96.6 | 96.7 |
| Impurity 1 (%) | 0.75 | 0.26 | 0.09 | n/d | n/d |
| Impurity 2 (%) | 0.53 | n/d | n/d | n/d | n/d |
| Impurity 3 (%) | 0.68 | 0.14 | 0.05 | n/d | n/d | n/d: not detected.

Example 16

Improved Process for Preparing 3

Scheme XI:
(a) T3P (50% in EtOAc), DIPEA, MeCN, 20° C., 20 h, 60-68%.
(b) H₂ (15 psig), 10% Pd/C (10 wt %), THF, 25° C., 1 h.
(c) THF, 22° C., 15 min, 80% (2 steps).
(d) DCC, THF, 0° C. to rt, 18 h, 80-85%.
(e) NMM (1.3 equiv), DMF (15 vol), -15 to -18° C., 7

Example 17

Preparation of Conjugate 3 Using PNP Esters

Scheme XIII

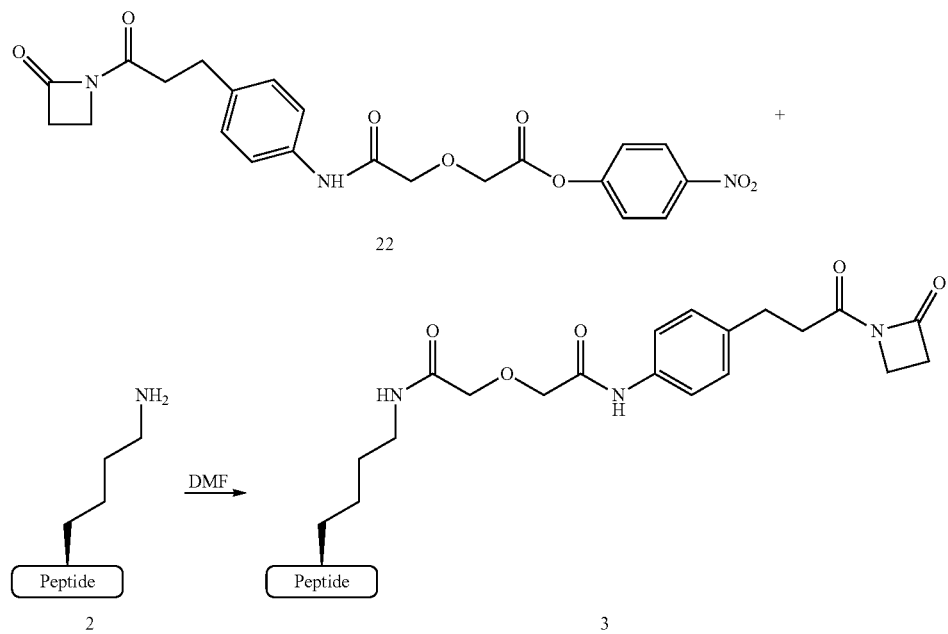

To a solution of compound 6 (0.5 g, 0.0015 moles, 1 equiv.) in THF (10 mL) compound 21 (p-nitrophenol) (0.23 g, 0.00165 moles, 1.1 equiv.) was added. The mixture was stirred at 0-5° C. The mixture was slightly cloudy. To this mixture DCC (0.325 g, 0.0016 moles, 1.05 equiv.) was added. The mixture was stirred at RT overnight. Next day the slurry was filtered through buchner funnel to remove precipitated DCU. The filtrate was evaporated to dryness on a rotary evaporator. The residue was slurried in 8 mL of isopropanol and stirred at 0-5° C. for 1 hr. The product slurry was filtered, washed with 5 mL of isopropanol and dried under high vacuum overnight, to provide a yield of 0.531 g (68%) of compound 22.

Compound 22 (0.3 g, 0.00066 moles, 3 equiv.) was placed in 35 mL round bottom flask. Solids were dissolved in 5 mL of DMF. To the solution of peptide 2a (SEQ ID NO:1) free-base (0.624 g, 0.000225 moles, 1 equiv.) was added as a solid. The reaction mixture was stirred at 0-5° C. for 8 hr. At the end of reaction period, HPLC analysis of the reaction mixture indicated that all of peptide 2a had disappeared. The mixture was added slowly in a dropwise manner to 150 mL of acetonitrile. The precipitated product slurry was stirred at room temperature for 3 hrs. The slurry was filtered through Buchner funnel using Whatman #2 filter paper. The slurry was filtered within 10 min. The product cake was washed with 15 mL of acetonitrile. The product compound 3d was dried under high vacuum for 16 hrs to afford a white product; compound 3d, in a yield of 0.612 g (86%).

Example 18

Summary of Reaction Completions and Product Purities

1. Reaction completion and product purity for compounds 6, 13, 14, and 20 were evaluated by HPLC using the following conditions: Column: Zorbax SB-CN 3.5 µm, 3×75 mm. Column temperature: 45° C. Detection: UV @ 210 nm. Mobile phase: A: water (0.05% TFA); B: MeCN. Gradient: 0 min: 95/5; 3.7 min: 5/95; 4.3 min: 5/95; 4.4 min: 95/5. Flow: 1.2 mL/min.

2. Reaction completion for peptide-linker conjugate 3 was evaluated by HPLC using the following conditions: Column: XBridge BEH130 C18 3.5 µm, 4.6×150 mm. Column temperature: 30° C. Detection: UV @ 210 nm. Mobile phase: A: 60/40 water/MeOH (0.1% formic acid); B: 60/40 MeCN/MeOH (0.085% formic acid). Gradient: 0 min: 95/5; 3 min: 95/5; 20 min: 60/40; 23 min: 0/100; 25 min: 0/100; 25.1 min: 95/5; 30 min: 95/5. Flow: 1 mL/min.

3. Product purity for compound 3 was evaluated by HPLC using the following conditions: Column: YMC-Pack ODS-A, 250×4.6 mm I.D., S-5 µm 12 nm, P/N AA12S05-2546WT. Column temperature: 60° C. Autosampler temperature: 5° C. Injection volume: 25 µL. Detection: UV @ 220 nm. Mobile phase: A: 0.1 M $NaClO_4$, pH adjusted to 3.1 with $H_3PO_4$; B: 0.1% TFA in ACN. Dissolving solvent: 1:1 Water/Dimethylformamide. Sample concentration: 1 mg/mL. Gradient: 0 min: 73/27; 2 min: 73/27; 32 min: 70/30; 42 min: 50/50; 42.1 min: 73/27; 50 min: 73/27 min. Flow: 1.5 mL/min.

4. $^1$H NMR and $^{13}$C NMR spectra were recorded on a 400 MHz spectrometer in either $CDCl_3$ or DMSO-$d_6$ as both solvent and internal standard. Mass data for compounds 6, 13, 14, and 20 was obtained on a Agilent 1100 Series LC/MSD SL spectrometer (ESI). Mass data for 3 was obtained using a MicroMass Q-ToF Global mass spectrometer (ESI).

Example 19

Conjugation of 3b with h38C2 Antibody

Conjugation of 3b was performed at a temperature range of between about 5° C. to about 35° C. The solution of 3b in a mixture of cosolvent and histidine buffer was added to a solution of h38C2 antibody (SEQ ID NO:3 and SEQ ID NO:4) in the buffer mixture containing histidine, glycine and sucrose. The conjugation was performed for about 2-about 24 hr. At the end of conjugation reaction the mixture was filtered through a 0.2 micron filter. The solution was then passed through Q-membrane filter to remove remaining residual peptide 3b. The solution was then concentrated and diafiltered through UF-DF membrane using histidine/glycine buffer solution at the desired pH; preferably pH 6.5. The concentrated solution of peptide-linker-antibody 5 was then diluted with histidine/glycine buffer containing polysorbate 20 and sucrose to the desired concentration; preferably to about 20 mg/mL.

Example 20

Change in the Cosolvent of the Conjugation Process

The process for the formation of the drug substance 5 was originally described in U.S. Pat. No. 8,288,349 whose contents are hereby incorporated. The original process involved use of propylene glycol as the cosolvent in the conjugation process between peptide-linker 3 and the antibody h38C2. Peptide-linker 3b has very low solubility in the solvent propylene glycol. Also, compounds of the type 3, in particular 3b, exist in two different solid forms, one being completely amorphous and the other solid form exhibits partial crystalline morphology. Both solid forms exhibit different solubility characteristics in different solvents and buffers. The more amorphous solid form is usually more soluble in different solvents and buffer solutions. However, it is difficult to control conditions of the process for preparation of 3b that would consistently result in the formation and isolation of only the solid form with higher solubility in the conjugation mixture. The manufacturing process of 3b typically affords the product as a mixture of two different solid forms. This renders the conjugation mixture during preparation of 5 heterogeneous, making kinetics of the conjugation reaction variable. During preparation of bioconjugate 5, it is desirable to have a conjugation mixture as a homogeneous solution at the beginning of the reaction in order to afford consistent reaction kinetics and more robust manufacturing process.

Surprisingly it was found that with DMSO as solvent, both the solid forms of 3b were readily soluble at ambient temperature at the desired concentration of 12 mg/mL and up to 100 mg/mL. In solvents other than DMSO such as acetonitrile and methanol, the more crystalline solid form had limited solubility, as shown in Table 7.

TABLE 7

Comparison of solubility of 3b in different solvents.

| Solvent | Solubility (mg/ml) |
| --- | --- |
| Acetonitrile | <0.01 |
| Methanol | <0.01 |
| Acetone | <0.01 |
| DMSO | >100 |
| THF | 0.01 |
| Acetonitrile/Water (2:1 v/v) | 0.39 |
| Acetonitrile/Water (1:1 v/v) | 0.73 |
| THF/Water (2:1 v/v) | 0.12 |
| Acetone/Water (2:1 v/v) | 0.43 |
| Methanol/Water (2:1 v/v) | |

In the original process, propylene glycol was used as a cosolvent primarily to assist in the dispersion of the hydrophobic peptide-linker 3b in the aqueous histidine buffer solution at pH 6.5. In the propylene glycol/histidine buffer mixture, both solid forms of 3b dissolve slowly over period of 2-3 hours albeit at different rates. This renders the conjugation mixture at the beginning of the conjugation reaction heterogeneous, making kinetics of the conjugation reaction variable. During preparation of bioconjugate 5, it was found to be advantageous to have a conjugation mixture as a homogeneous solution at the start of the reaction in order to afford predictable reaction rate. It was discovered that replacing propylene glycol with DMSO (up to 10% v/v) as cosolvent in the conjugation process of 5 resulted the reaction mixture that was homogeneous. This in turn afforded more consistent and predictable reaction rate of the conjugation process and a more robust manufacturing process for formation of 5.

The h338C2 used in the process consists of a mixture of mAb species that contain fully conjugatable mAb, partially conjugatable mAb, and non-conjugatable mAb. The conjugation of h38C2 with the peptide 3b affords 5 as a mixture of conjugate containing fully conjugated two loaded (+2) species, partially loaded species (+1) and unconjugatable mAb (0 loaded species).

In order to investigate the impact of different conjugation reaction variables on the reaction rate, product quality and yield, a set of experiments were executed using design of experiments (DOE) approach. Three parameters were chosen for evaluation: pH of the conjugation mixture, temperature of the conjugation and the ratio of peptide to starting antibody. Other parameters such as composition of the buffer solution (20 mM histidine buffer), antibody concentration (16.7 mg/mL) and concentration of DMSO in solution (7%) were kept constant. The centre point for each parameter was pH6.5, 20° C. and a peptide:antibody ratio of 2.4:1. The low levels tested were pH5.5, 5° C. and a ratio of 1.8, and the high levels were pH7.5, 35° C. and a ratio of 3.

Several experiments whose variable values were at the center-point of all the parameter ranges were selected to provide information on possible non-linear effects. The protocol for these experiments was briefly as follows: Peptide 3b (25 mg) was placed in a 20 mL vial equipped with a magnetic stir bar. The solid was dissolved in DMSO (2.1 mL). Histidine buffer (20 mM, pH 6.5, 2.1 mL) was added to the solution. The mixture was stirred for 90 mins at 20° C. The solution of antibody h38C2 (25.13 mL, 19.9 mg/mL) was added to a separate jacketed reactor. To this solution was added the solution of peptide 3b in DMSO/histidine buffer with a syringe over 2-3 min period. The mixture was stirred at 20° C. The reaction was monitored for completion by SEC and HIC chromatography methods. The protocol for the remaining tests as identical, except in the respective pH, temperature and ratio of peptide:antibody. The in-situ yield of 5 and time of reaction completion (hours) were evaluated by HIC and SEC chromatographic methods. Results of the DOE experiment are shown in Table 8.

TABLE 8

DOE for conjugation parameters.

| pH | Temp. | Peptide Ratio | % +2 by HIC | % +1 by HIC | % 0 by HIC | % Peptide by Org. SEC | Reaction Compl. (hr) |
| --- | --- | --- | --- | --- | --- | --- | --- |
| 5.5 | 35 | 3 | 81.7 | 17.3 | 0.9 | 10.1 | 1 |
|  |  |  | 83.6 | 15.7 | 0.7 | — | 3 |
|  |  |  | 83.9 | 15.4 | 0.7 | 10.2 | 5 |
| 5.5 | 5 | 3 | 20.3 | 48.5 | 31.2 | 15 | 1 |
|  |  |  | 37.4 | 47.2 | 15.3 | 13 | 3 |
|  |  |  | 40.5 | 47 | 12.5 | 9.4 | 5 |
|  |  |  | 73 | 25 | 2 | 8.9 | 16 |
| 5.5 | 35 | 1.8 | 57.8 | 38.3 | 3.9 | 0.6 | 1 |
|  |  |  | 58.4 | 37.6 | 4 | 0.4 | 2 |
|  |  |  | 57.8 | 38.1 | 4.1 | 0.2 | 3 |
|  |  |  | 62.4 | 35.3 | 2.3 | 0 | 16 |
| 5.5 | 5 | 1.8 | 25.5 | 49.8 | 24.7 | 9.2 | 1 |
|  |  |  | 37.1 | 53.4 | 9.5 | 3.2 | 3 |
|  |  |  | 53.3 | 39.6 | 7.1 | 1.2 | 5 |
|  |  |  | 58 | 39.4 | 5.5 | 0.8 | 7 |
|  |  |  | 61.8 | 33.8 | 4.4 | 0.6 | 11 |

TABLE 8-continued

DOE for conjugation parameters.

| pH | Temp. | Peptide Ratio | % + 2 by HIC | % + 1 by HIC | % 0 by HIC | % Peptide by Org. SEC | Reaction Compl. (hr) |
|---|---|---|---|---|---|---|---|
| 6.5 | 20 | 2.4 | 82   | 17   | 1   | 5.7  | 2 |
|     |    |     | 83.4 | 16.5 | 1   | 4.9  | 4 |
|     |    |     | 89.6 | 10.4 | 0   | 3.4  | 24 |
| 6.5 | 20 | 2.4 | 77.9 | 20.7 | 1.3 | 4.6  | 1 |
|     |    |     | 82.9 | 16.3 | 0.8 | 3.7  | 3 |
|     |    |     | 83.5 | 15.7 | 0.8 | 3.4  | 5 |
| 7.5 | 35 | 3   | 83   | 16.5 | 0.5 | 10.3 | 0.75 |
|     |    |     | 85.5 | 14   | 0.5 | 9.6  | 3 |
| 7.5 | 5  | 3   | 47.3 | 43.3 | 9.4 | 14.7 | 1 |
|     |    |     | 75.6 | 22   | 1.6 | 9.9  | 3 |
|     |    |     | 80.8 | 18.2 | 1   | 9    | 5 |
|     |    |     | 81.9 | 17.2 | 0.9 | 8.8  | 6 |
| 7.5 | 35 | 1.8 | 69.1 | 28.2 | 2.7 | 0    | 1 |
|     |    |     | 69.5 | 28   | 2.5 | 0    | 3 |
|     |    |     | 69.5 | 28.1 | 2.4 | 0    | 5 |
| 7.5 | 5  | 1.8 | 64.7 | 32.1 | 3.2 | 0.1  | 2 |
|     |    |     | 68.3 | 28   | 3.6 | 0.1  | 4 |
|     |    |     | 69.6 | 27.2 | 3.2 | 0.1  | 24 |

Conclusions from the DOE studies are as follows:
Within the given design space for the conjugation:
  At a given pH, increased yield of +2 is obtained at higher temperature and higher peptide:mAb ratio.
  At a given peptide ratio, higher yield of +2 is obtained at higher pH and higher temperature.
  At given temperature, higher pH and higher peptide ratio affords higher yield of +2.
  pH of the conjugation mixture has maximum effect on the reaction rate. At low pH the conjugation reaction is slower.
  Within the reaction design space as defined by parameters and their range limits, the optimum yield of +2 of the conjugate is obtained within the standard reaction time of 3 hrs when the peptide ratio is between 2.1-3 equiv., pH is 6.5-7.5 and temperature is between 20-30° C. However the desired product can still be obtained within the broader range limits for pH (5.5-7.5) and temperature (5-35° C.) as long as peptide ratio is between 1.8-3 equiv. and the conjugation reaction is allowed to proceed to its completion. To minimize cost of goods and maximize productivity, the conjugation reaction is normally performed with peptide/antibody ratio of 2.1 at RT, (for example, 22° C.) and pH of 6.5. At higher temperatures (e.g. 30-35° C.) and at higher pH (e.g. about pH7.5) the degradation of peptide 3b occurs at a faster rate. Addition of significant excess of peptide 3b to the conjugation mixture can potentially lead to formation of more process related impurities, particularly at high pH conditions. Therefore, while the process can operate within the defined parameters, it is preferable to operate within the optimized ranges.

In some aspects, the invention provides for a method of conjugation of peptide-linker to an antibody as herein described, comprising
(i) dissolving compound 3b in DMSO; preferably at between about 5 and about 100 mg/ml, more preferably at between about 10 and about 15 mg/ml, most preferably at about 12 mg/ml; preferably for a duration of at least about 1 min, at least about 5 mins, and preferably at least about 15 mins (as the reaction is stable, there need not be an upper limit to the duration);
(ii) adding histidine buffer (as described herein and below) (pH between about 5.5 to about 7.5), preferably about pH 6.5 to the solution of compound 3b made in (i); preferably about an about equal volume, preferably to between about 2 and about 10 mg/ml, more preferably at between about 5 and about 8 mg/ml, most preferably at about 6 mg/ml;
(iii) Adding h38C2 antibody;
(iv) Agitating at a medium speed so as to avoid foaming the reaction mixture for at least about 1 hr, preferably at about between about 15° C. to about 35° C., more preferably at RT, and most preferably at about 22° C.;
(v) Filtration of the solution from (iv).

Accordingly, in some aspects, the invention provides for a process for conjugating a peptide of formula 3b to an antibody comprising the steps:
(i) dissolving compound 3b in DMSO:

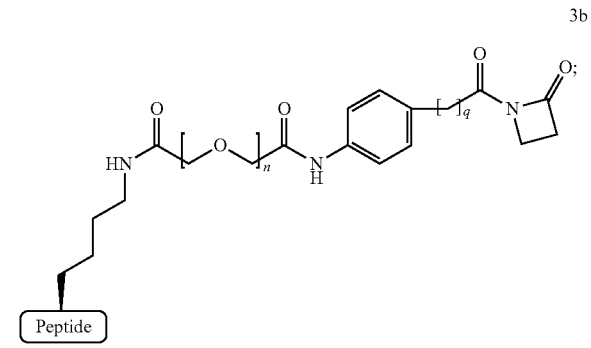

3b (ii) adding histidine buffer at pH between about 5.5 to about 7.5 to the solution of DMSO and 3b of step (i);
(iii) Adding an antibody comprising a variable light region comprising SEQ ID NO:5 and a variable heave region comprising SEQ ID NO:6 to the solution of step (ii), so as to have a peptide:antibody molar ratio of between about 1.8:1 to about 3:1;
(iv) Agitating the mixture formed in step (vi) at a medium speed so as to avoid foaming the reaction mixture for at least about 1 hr at between about pH 5.5 and about pH7.5 and at a temperature of between about 5° C. and 35° C.;
(v) Filtration of the solution from (iv) to extract the resultant peptide-linker antibody conjugate 5b.

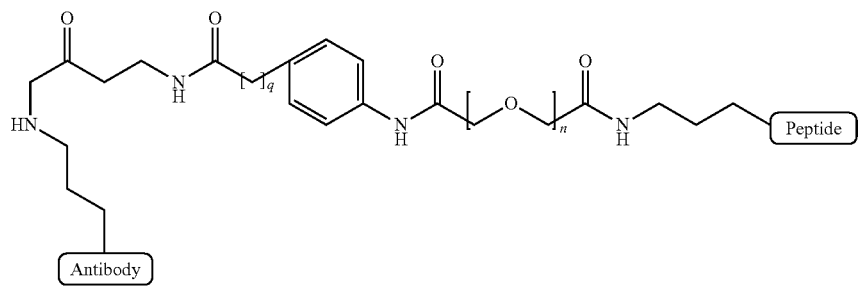

5b wherein n=1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, q=1, 2, 3, 4, or 5.

In some aspects, the antibody may be in a solution comprising between about 1 mM to about 100 mM histidine, preferably about 5 to about 20 mM, more preferably about 10 mM histidine; between about 1 and about 100 mM glycine, preferably between about 1 and about 20 mM glycine, more preferably about 10 mM glycine buffer; and further comprising between about 0.1 and about 10% (w/w) sucrose, preferably between about 0.5% and about 5% (w/w) sucrose, more preferably between about 1% and about 3% (w/w) sucrose, and most preferably about 2% (w/w) sucrose. Preferably the final concentration of the antibody in the conjugation mixture may be between about 10 and about 30 mg/ml, more preferably between about 14 and about 20 ml, most preferably about 16.7 mg/mL.

In some aspects, the agitation may be done in a stainless steel reactor with bottom mounted magnetic coupled agitator (6 bladed with 6" diameter blades) at 70 rpm or in a glass reactor using overhead mechanical agitator with Teflon paddle at 120 rpm speed. The reaction mixture may be agitated for at least about 1 hr, more preferably at least about 2 hr, more preferably between about 1 hr and overnight, further preferably between about 2 hr and about 6 hr, and most preferably about 3 hr.

In some aspects, the filtration is by a 0.2 μm filter; following which, the filtrate may be subjected to Q-filtration. Following this, the filtrate may be subjected to a UF/DF filtration, such as through a Hydrosart ultrafiltration membrane with 30 Kilodalton Molecular Weight Cut off with the buffer containing 20 mM histidine and 200 mM glycine at pH 6.5, and formulation with polysorbate 20 (0.1% w/w) and sucrose (2% w/w) followed by further 0.2 μm filtration.

In some aspect, the above reaction relates to compound 3b and compound 5b. In some aspects of the above, n=1, and the process relates to compound 3a and compound 5a. In some aspects, n=1 and q=1, and the process relates to compound 3 and compound 5.

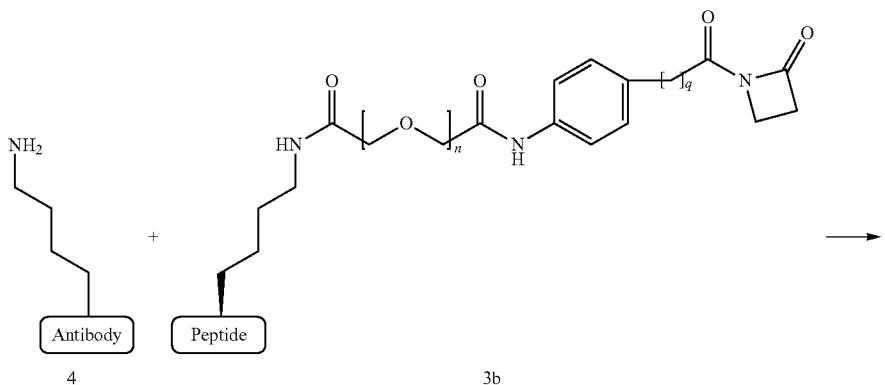

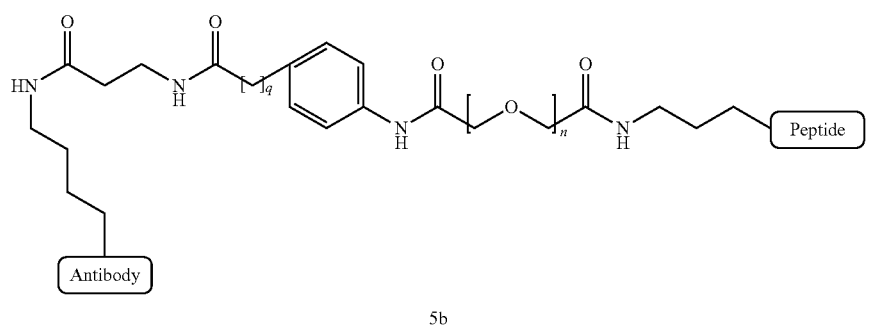

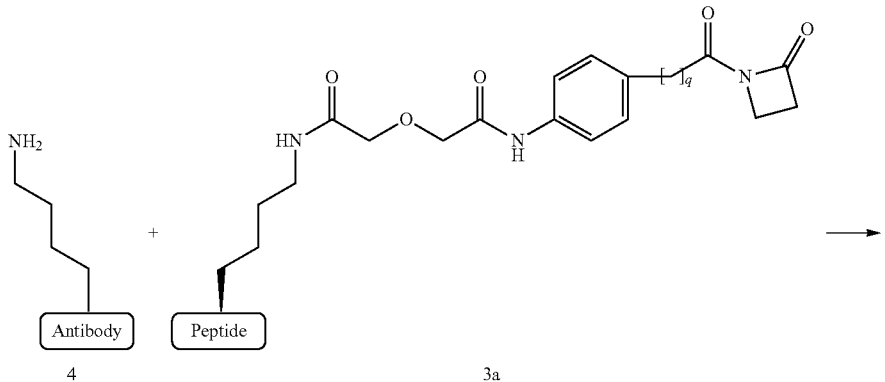

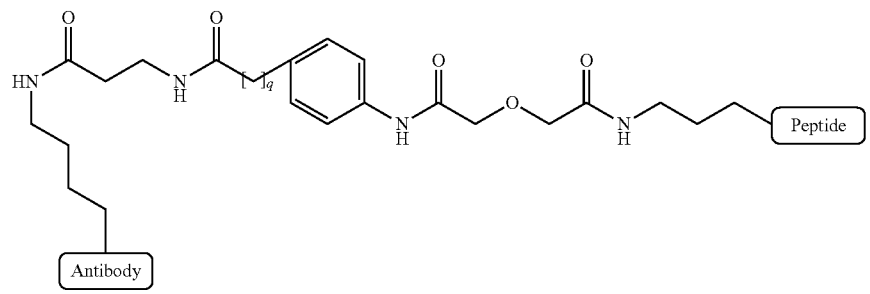
5a
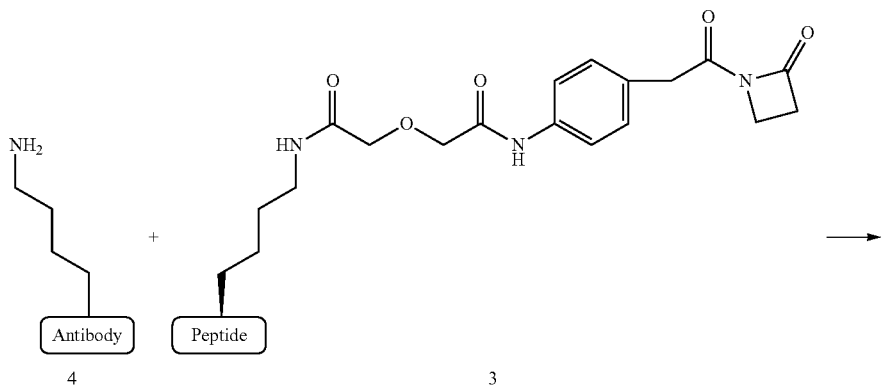
4 + 3
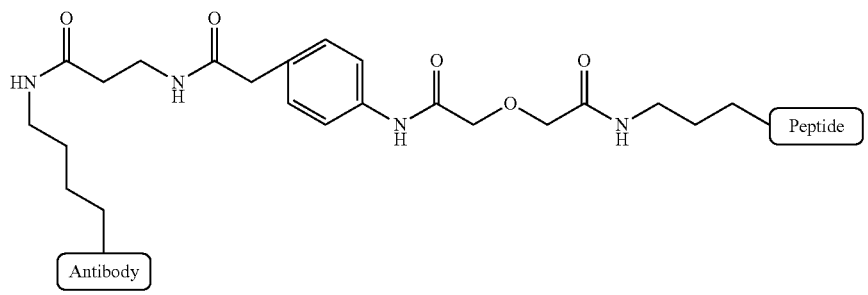
5
Example 21
Improved Process for Preparing 5 from 9 and 11
Scheme XV:
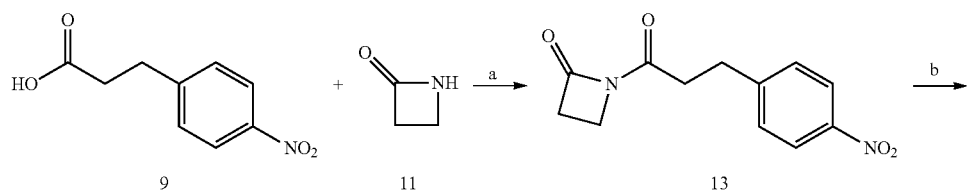
9 + 11 → 13

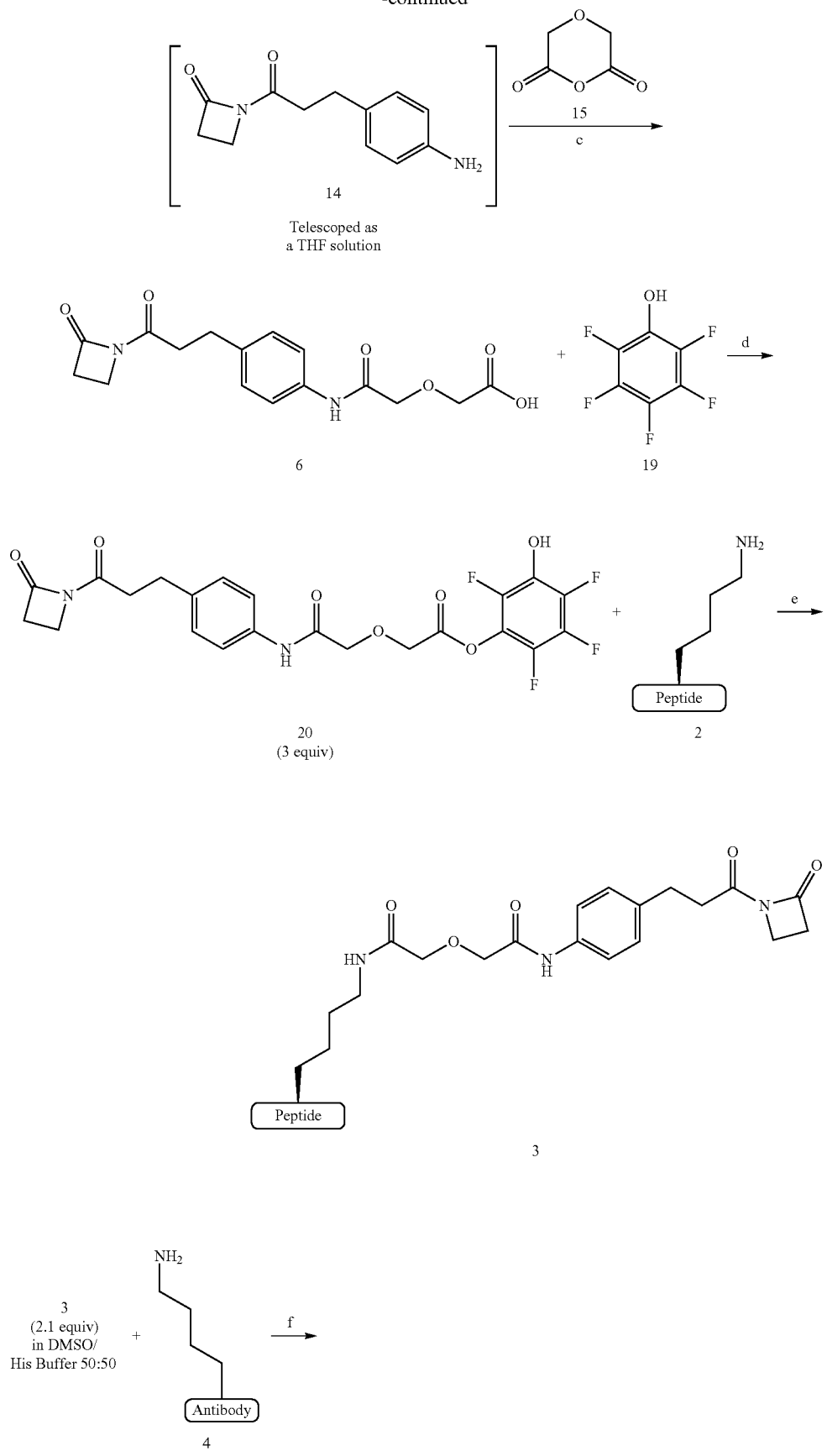

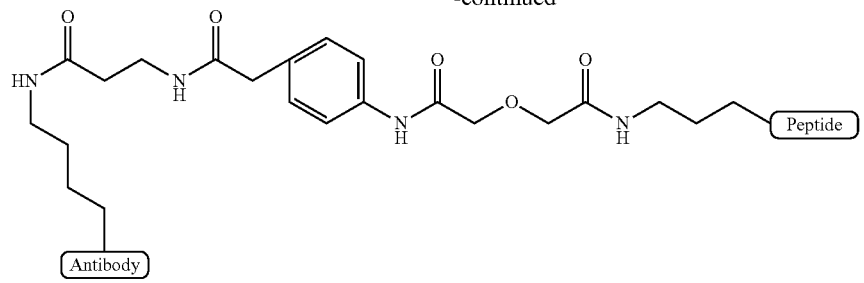

5

(a) T3P (50% in EtOAc), DIPEA, MeCN, 20° C., 20 h, 60-68%.
(b) H₂ (15 psig), 10% Pd/C (10 wt %), THF, 25° C., 1 h.
(c) THF, 22° C., 15 min, 80% (2 steps).
(d) DCC, THF, 0° C. to rt, 18 h, 80-85%.
(e) NMM (1.3 equiv), DMF (15 vol), -15 to -18° C., 7.
(f) agitation at 22° C., pH 6.5, Example 22

Improved Process for Preparing 5 from 3 and 4

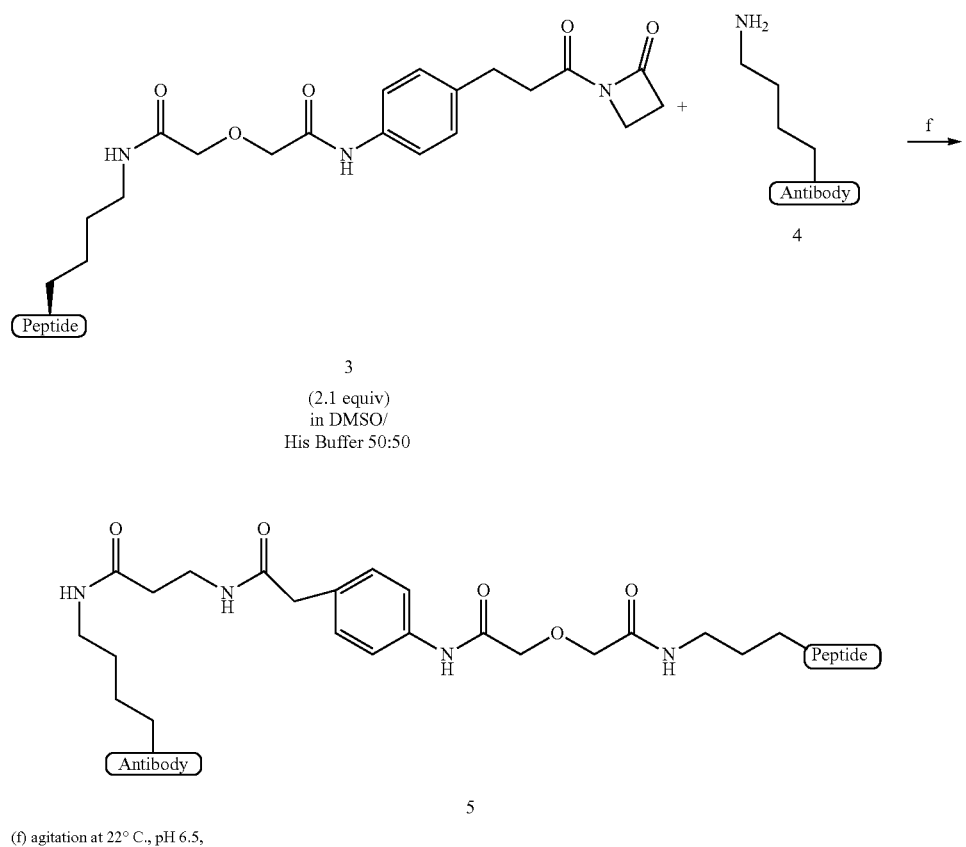

(f) agitation at 22° C., pH 6.5,

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description.

The use of the term "or" in the claims is used to mean "and/or" unless explicitly indicated to refer to alternatives only or the alternative are mutually exclusive, although the disclosure supports a definition that refers to only alternatives and "and/or."

As used herein the specification, "a" or "an" may mean one or more, unless clearly indicated otherwise. As used herein in the claim (s), when used in conjunction with the word "comprising, "the words "a" or "an" may mean one or more than one. As used herein "another" may mean at least a second or more.

The words "comprises/comprising" and the words "having/including" when used herein with reference to the present invention are used to specify the presence of stated features, integers, steps or components but does not preclude the presence or addition of one or more other features, integers, steps, components or groups thereof.

The invention claimed is:

1. A process for preparing a compound according to formula 5a

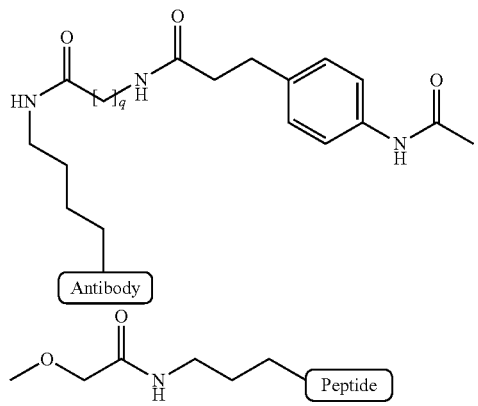

comprising
(i) reacting 9a and 11 together in the presence of 1-propanephosphonic acid anhydride (T3P) to create compound 13a

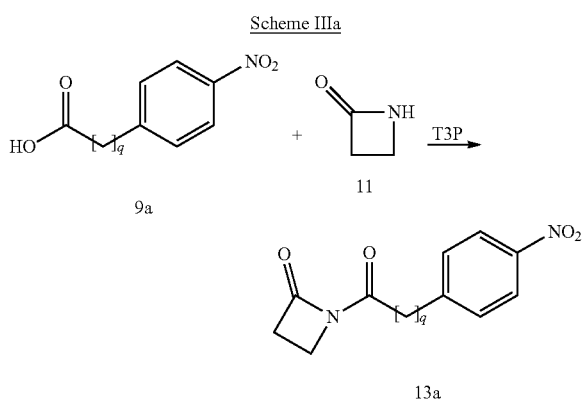

(ii) catalytic hydrogenation with Pd/C of compound 13a in a THF:H$_2$O solution of at least about 50% THF to produce a compound of formula 4a

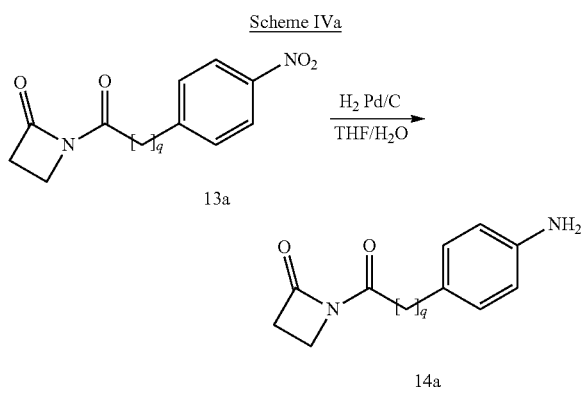

(iii) combining a solution of 14a in THF with a compound according to formula 15 in a reaction substantially free of base to produce compound 6a

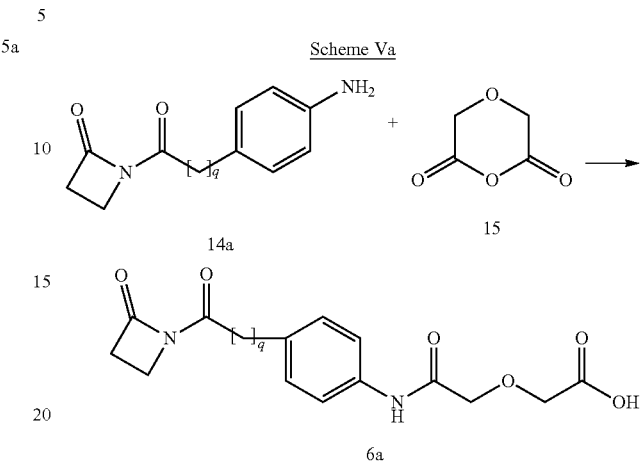

(iv) reacting a compound according to the formula 6a with a compound according to formula 19a in THF in the presence of DCC to produce compound 20a

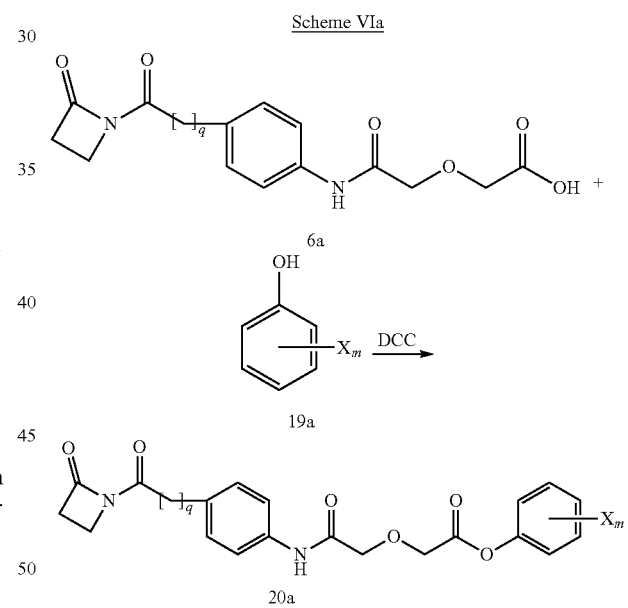

(v) combining 20a with a ε-amino containing peptide 2 dissolved in an aprotic polar 15th solvent to produce compound 3a

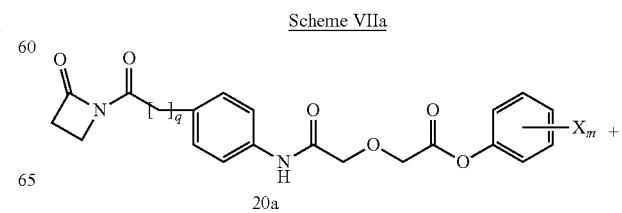

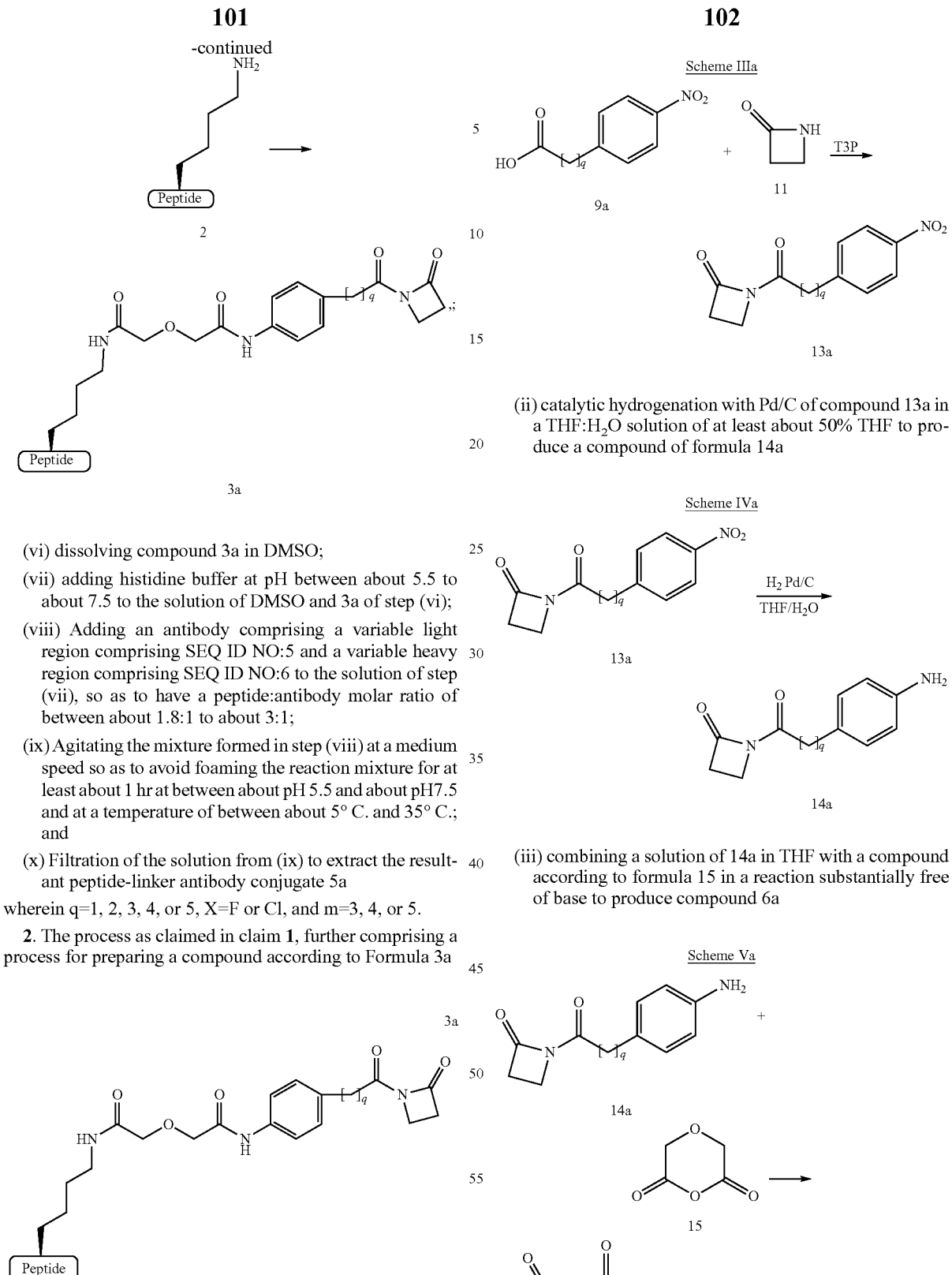

(vi) dissolving compound 3a in DMSO;

(vii) adding histidine buffer at pH between about 5.5 to about 7.5 to the solution of DMSO and 3a of step (vi);

(viii) Adding an antibody comprising a variable light region comprising SEQ ID NO:5 and a variable heavy region comprising SEQ ID NO:6 to the solution of step (vii), so as to have a peptide:antibody molar ratio of between about 1.8:1 to about 3:1;

(ix) Agitating the mixture formed in step (viii) at a medium speed so as to avoid foaming the reaction mixture for at least about 1 hr at between about pH 5.5 and about pH 7.5 and at a temperature of between about 5° C. and 35° C.; and (x) Filtration of the solution from (ix) to extract the resultant peptide-linker antibody conjugate 5a wherein q=1, 2, 3, 4, or 5, X=F or Cl, and m=3, 4, or 5.

2. The process as claimed in claim 1, further comprising a process for preparing a compound according to Formula 3a comprising (i) reacting 9a and 11 together in the presence of 1-propanephosphonic acid anhydride (T3P) to create compound 13a (ii) catalytic hydrogenation with Pd/C of compound 13a in a THF:H$_2$O solution of at least about 50% THF to produce a compound of formula 14a (iii) combining a solution of 14a in THF with a compound according to formula 15 in a reaction substantially free of base to produce compound 6a (iv) reacting a compound according to the formula 6a with a compound according to formula 19a in THF in the presence of DCC to produce compound 20a Scheme VIa

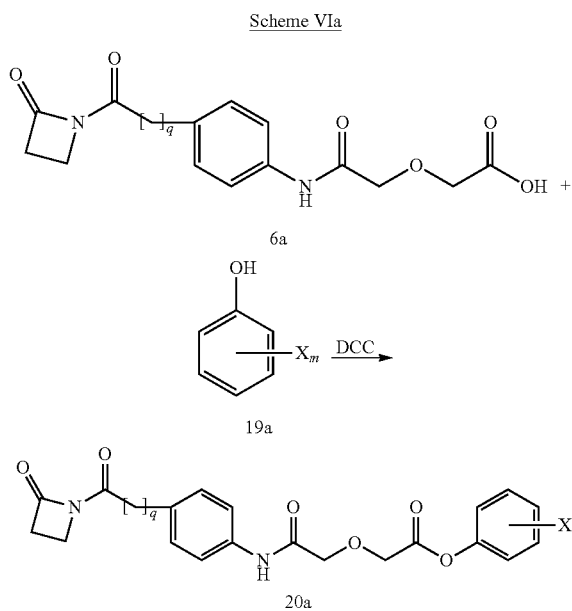

(v) combining 20a with a ε-amino containing peptide 2 dissolved in an aprotic polar 15th solvent to produce bioconjugate 3b Scheme VIIa

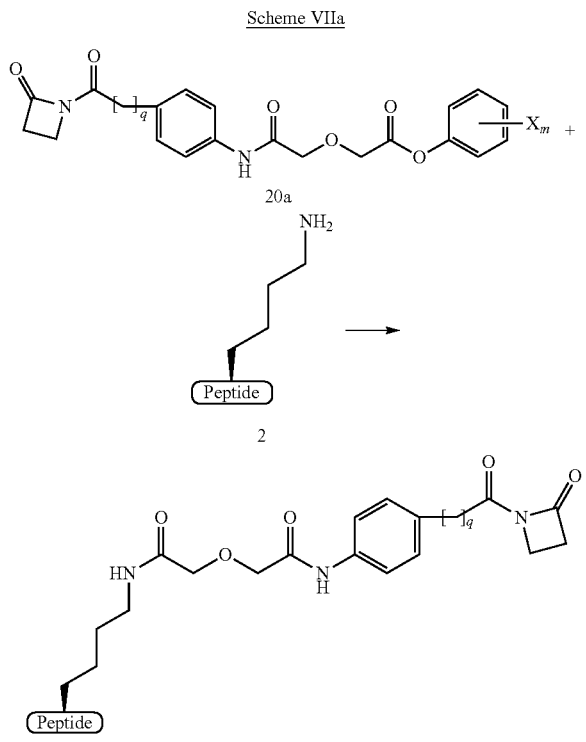

wherein q=1, 2, 3, 4, or 5, X=F or Cl, and m=3, 4, or 5.

3. The process as claimed in claim 1, further comprising a process for preparing a compound of formula 13a

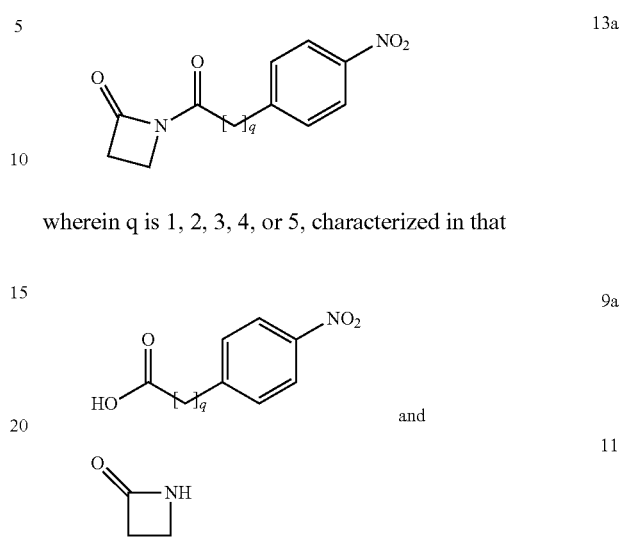

wherein q is 1, 2, 3, 4, or 5, characterized in that are reacted together in the presence of 1-propanephosphonic acid anhydride (T3P).

4. The process as claimed claims 1, wherein the reaction between 9a and 11 is carried out in the presence of a $1^{st}$ solvent selected from the group consisting of of tetrahydrofuran (THF), 2-methyltetrahydrofuran, 1-methyl-2-pyrrolidinone (NMP), N,N-dimethylformamide (DMF), N,N-dimethylacetamide (DMAc), 1-methyl-2-pyrrolidinone, ethyl acetate (EtOAc), and acetonitrile (MeCN), and preferably MeCN.

5. The process as claimed in claim 4, wherein the reaction is carried out in the presence of a $1^{st}$ base selected from the group consisting of trimethylamine, triethylamine, tributylamine, DIPEA, pyridine, DBU, DABCO, 2,3-lutidine, 2,4-lutidine, 2,5-lutidine, 2,6-lutidine, 3,4-lutidine, 3,5-lutidine, and preferably DIPEA.

6. The process as claimed in claim 1, further comprising a_process for preparing a compound of formula 4a,

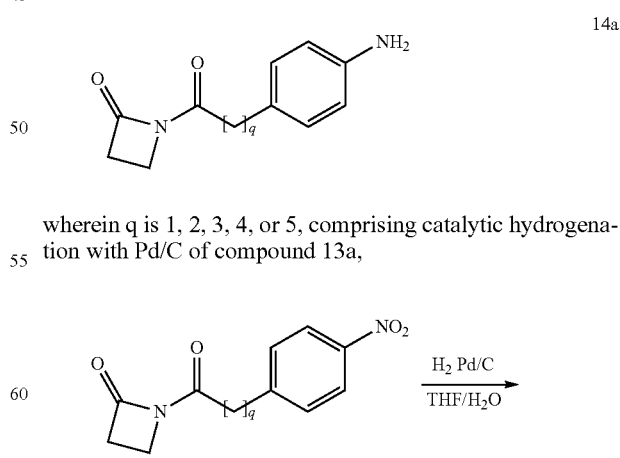

wherein q is 1, 2, 3, 4, or 5, comprising catalytic hydrogenation with Pd/C of compound 13a, and characterized in that the reaction is conducted in a THF:$H_2O$ solution of at least about 50% THF.

7. The process as claimed in claim 1, wherein the THF:H$_2$O solution comprises THF in an amount selected from the group consisting of at least about 60%, at least about 70%, at least about 80%, and at least about 90%.

8. The process as claimed in claim 1, wherein prior to hydrogenation in THF/H$_2$O, compound 13a is subjected to treatment with activated charcoal.

9. The process as claimed in claim 8, wherein the activated charcoal is selected from the group consisting of SX-Plus, Darco® S-51HF, E Supra USP, SX-Ultra, CASP, Darco® G-60 and CGSP.

10. The process as claimed in claim 1, further comprising a process for preparing a compound of formula 6a

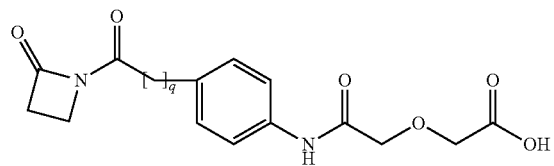
6a wherein q=1, 2, 3, 4 or 5; comprising reacting a solution of compound 14a

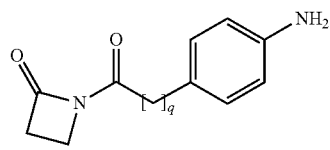
14a in a 6$^{th}$ solvent comprising THF, with compound 15

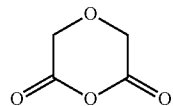
15 and characterized in that the reaction is carried out substantially free of a base.

11. The process as claimed in claim 1, wherein the compound 14a is reacted with between about 1 and about 10 equivalents of compound 15.

12. The process as claimed in claim 1, wherein the solution of compound 6a is distilled under vacuum, following which a 7$^{th}$ solvent comprising C$_1$-C$_4$ alkyl acetate is added to attain a solvent composition of between about 25%THF/75% C$_1$-C$_4$ alkyl acetate and about 100% C$_1$-C$_4$ alkyl acetate.

13. The process as claimed in claim 12, wherein the 7$^{th}$ solvent is selected from the group consisting of methyl acetate, ethyl acetate, i-propyl acetate, n-propyl acetate, n-butyl acetate, and preferably is i-propyl acetate.

14. The process as claimed in claim 12, wherein the ratio between 6$^{th}$ and 7$^{th}$ solvents is between 25:75 and 0:100.

15. The process as claimed in claim 1, further comprising a process for crystallization of a compound according to the formula 6a, comprising
(i) dissolving acid 6a in an 8$^{th}$ solvent comprising THF;
(ii) optionally treating with activated carbon and then filtering off said activated carbon;
(iii) concentrating the acid 6a in THF solution to between about 2 and about 20 vol;
(iv) adding between about 1 and about 50 vol of a 9$^{th}$ solvent consisting of 2-propanol;
(v) concentrating the solution of acid 6a in THF and 2-propanol to between about 2 and about 50 vol;
(vi) cooling the concentrated solution of acid 6 to between about −25° C. and about 10° C.

16. The process as claimed in claim 1, further comprising a process for preparing a compound according to the formula 20b comprising reacting a compound according to the formula 6b with a compound according to formula 19a in a 10$^{th}$ solvent in the presence of DCC Scheme VIa

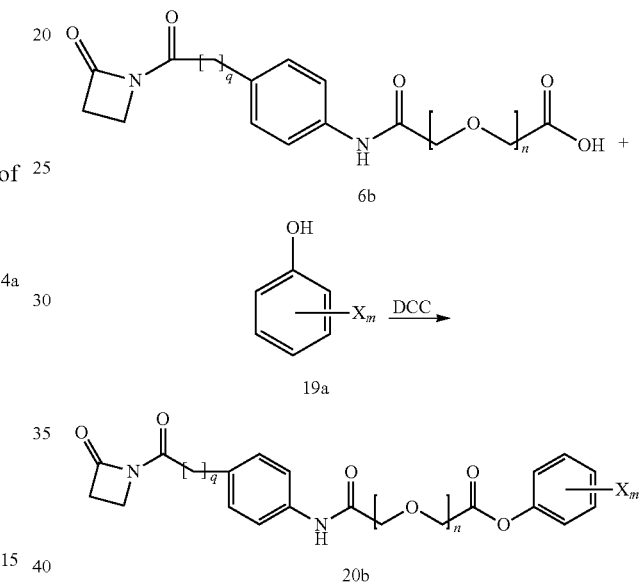

wherein q=1, 2, 3, 4, or 5, n=1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, X=F or Cl, and m=3, 4, or 5.

17. The process of claim 1, further comprising a process for conjugating an ε-amino containing peptide 2 to a linker of the formula 6b comprising:
(i) dissolving peptide 2 in an aprotic, polar 15$^{th}$ solvent,
(ii) reacting 6b with between about 1 and about 10 equivalents of 19a in THF to produce compound 20b;
(iii) combining 20b with peptide 2 to produce bioconjugate 3b Scheme XIIb

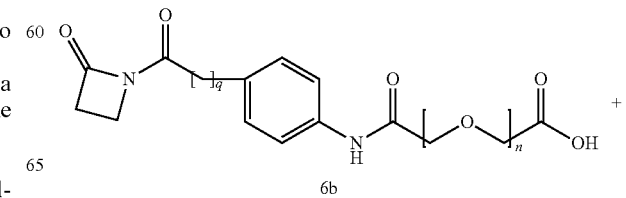

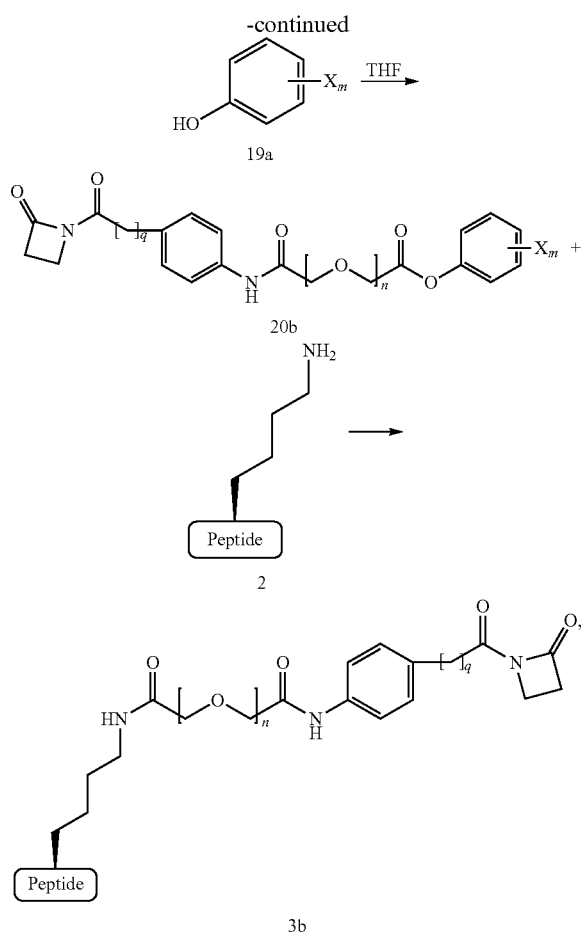

wherein n=1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, q=1, 2, 3, 4, or 5, X=F or Cl, and m=3, 4, or 5.

18. The process as claimed in claim 1, wherein at least about 1 equivalent of compound 19a is added to compound 6a or 6b.

19. The process as claimed in claim 1, wherein the DCC is added to the reaction at a temperature of between −10° C. and +10° C., and preferably between about +3° C. and +5° C.

20. The process as claimed in claims 1, wherein the reaction between compound 19a and either 6a or 6b takes place in a $10^{th}$ solvent selected from the group consisting of THF, dichloromethane, 2-methyltetrahydrofuran, N,N-dimethylformamide, and N,N-dimethylacetamide, and preferably THF.

21. The process as claimed in claim 1, wherein X is F, and m is 5.

22. The process as claimed in claim 1 wherein compound 3a or compound 3b is dissolved in DMSO at between about 5 and about 100 mg/ml, and preferably at between about 10 and about 15 mg/ml.

23. The process as claimed in claim 1, wherein the histidine buffer is added to the DMSO solution of compound 3a or 3b at an equal volume, plus or minus 10%.

24. The process as claimed in claim 1, wherein the concentration of compound 3a or compound 3b following addition of the histidine buffer is between about 2 and about 10 mg/ml, and is preferably about 6 mg/ml.

25. The process as claimed in claim 1, wherein the antibody comprises a light chain constant region comprising a sequence selected from the group consisting of SEQ ID NOs: 9, 10, 11, and 12, or variants thereof comprising between 1 and 5 amino acid substitutions, deletions or insertions, and a heavy chain constant region comprising a sequence selected from the group consisting of SEQ ID NOs:13, and 14, or variants thereof comprising between 1 and 5 amino acid substitutions, deletions or insertions.

26. The process as claimed in claim 25, whererin the antibody comprises a light chain comprising SEQ ID NO:3, or variants thereof comprising between 1 and 5 amino acid substitutions, deletions or insertions, and a heavy chain comprising SEQ ID NO:4, or variants thereof comprising between 1 and 5 amino acid substitutions, deletions or insertions.

27. The process as claimed in claimed 1, wherein q=2, n when present =1, m when present =5, and x when present =F.

* * * * *

SEQUENCE LISTING

```
<160> NUMBER OF SEQ ID NOS: 14

<210> SEQ ID NO 1
<211> LENGTH: 22
<212> TYPE: PRT
<213> ORGANISM: Artificial Sequence
<220> FEATURE:
<223> OTHER INFORMATION: Ang2 binding peptide based on Exendin 4
<220> FEATURE:
<221> NAME/KEY: MISC_FEATURE
<222> LOCATION: (2)..(2)
<223> OTHER INFORMATION: X = Acyl Lysine
<220> FEATURE:
<221> NAME/KEY: MISC_FEATURE
<222> LOCATION: (9)..(9)
<223> OTHER INFORMATION: X = Acyl Lysine

<400> SEQUENCE: 1

Gln Xaa Tyr Gln Pro Leu Asp Glu Xaa Asp Lys Thr Leu Tyr Asp Gln
1               5                   10                  15

Phe Met Leu Gln Gln Gly
            20

<210> SEQ ID NO 2
<211> LENGTH: 24
<212> TYPE: PRT
<213> ORGANISM: Artificial Sequence
<220> FEATURE:
<223> OTHER INFORMATION: Ang2 binding peptide based on Exendin 4
<220> FEATURE:
<221> NAME/KEY: MISC_FEATURE
<222> LOCATION: (1)..(1)
<223> OTHER INFORMATION: absent
<220> FEATURE:
<221> NAME/KEY: MISC_FEATURE
<222> LOCATION: (3)..(3)
<223> OTHER INFORMATION: X = Acyl Lysine
<220> FEATURE:
<221> NAME/KEY: MISC_FEATURE
<222> LOCATION: (10)..(10)
<223> OTHER INFORMATION: X = Acyl Lysine
<220> FEATURE:
<221> NAME/KEY: MISC_FEATURE
<222> LOCATION: (24)..(24)
<223> OTHER INFORMATION: absent

<400> SEQUENCE: 2

Xaa Gln Xaa Tyr Gln Pro Leu Asp Glu Xaa Asp Lys Thr Leu Tyr Asp
1               5                   10                  15

Gln Phe Met Leu Gln Gln Gly Xaa
            20
```

<210> SEQ ID NO 3
<211> LENGTH: 219
<212> TYPE: PRT
<213> ORGANISM: Artificial Sequence
<220> FEATURE:
<223> OTHER INFORMATION: Humanized murine monoclonal antibody - h38C2
      light chain

<400> SEQUENCE: 3

Glu Leu Gln Met Thr Gln Ser Pro Ser Ser Leu Ser Ala Ser Val Gly
1               5                   10                  15

Asp Arg Val Thr Ile Thr Cys Arg Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 4
<211> LENGTH: 448
<212> TYPE: PRT
<213> ORGANISM: Artificial Sequence
<220> FEATURE:
<223> OTHER INFORMATION: Humanized murine monoclonal antibody - h38C2
      heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

```
Leu Tyr Leu Gln Met Asn Ser Leu Arg Ala Glu Asp Thr Gly Ile Tyr
                 85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 5
<211> LENGTH: 112
<212> TYPE: PRT
<213> ORGANISM: Artificial Sequence
<220> FEATURE:
<223> OTHER INFORMATION: Humanized murine monoclonal antibody - variable
      light chain h38c2

<400> SEQUENCE: 5
```

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

<210> SEQ ID NO 6
<211> LENGTH: 118
<212> TYPE: PRT
<213> ORGANISM: Artificial Sequence
<220> FEATURE:
<223> OTHER INFORMATION: Humanized murine monoclonal antibody - variable
      heavy chain h38c2

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65              70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser
        115

<210> SEQ ID NO 7
<211> LENGTH: 112
<212> TYPE: PRT
<213> ORGANISM: Artificial Sequence
<220> FEATURE:
<223> OTHER INFORMATION: Murine monoclonal antibody - variable light
      m38C2

<400> SEQUENCE: 7

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Arg Ile
 65                  70                  75                  80

Ser Arg Val Glu Ala Glu Asp Leu Gly Val Tyr Phe Cys Ser Gln Gly
                 85                  90                  95

Thr His Leu Pro Tyr Thr Phe Gly Gly Gly Thr Lys Leu Glu Ile Lys
            100                 105                 110
```

<210> SEQ ID NO 8
<211> LENGTH: 118
<212> TYPE: PRT
<213> ORGANISM: Artificial Sequence
<220> FEATURE:
<223> OTHER INFORMATION: Murine monoclonal antibody - variable heavy m38C2

<400> SEQUENCE: 8

```
Glu Val Lys Leu Val Glu Ser Gly Gly Gly Leu Val Gln Pro Gly Gly
 1               5                  10                  15

Thr Met Lys Leu Ser Cys Glu Ile Ser Gly Leu Thr Phe Arg Asn Tyr
             20                  25                  30

Trp Met Ser Trp Val Arg Gln Ser Pro Glu Lys Gly Leu Glu Trp Val
         35                  40                  45

Ala Glu Ile Arg Leu Arg Ser Asp Asn Tyr Ala Thr His Tyr Ala Glu
 50                  55                  60

Ser Val Lys Gly Lys Phe Thr Ile Ser Arg Asp Ser Lys Ser Arg
 65                  70                  75                  80

Leu Tyr Leu Gln Met Asn Ser Leu Arg Thr Glu Asp Thr Gly Ile Tyr
                 85                  90                  95

Tyr Cys Lys Tyr Tyr Phe Tyr Ser Phe Ser Tyr Trp Gly Gln Gly Thr
            100                 105                 110

Leu Val Thr Val Ser Ala
            115
```

<210> SEQ ID NO 9
<211> LENGTH: 107
<212> TYPE: PRT
<213> ORGANISM: Homo sapiens
<220> FEATURE:
<221> NAME/KEY: MISC_FEATURE
<222> LOCATION: (46)..(46)
<223> OTHER INFORMATION: X = V or A
<220> FEATURE:
<221> NAME/KEY: MISC_FEATURE
<222> LOCATION: (84)..(84)
<223> OTHER INFORMATION: X = V or L

<400> SEQUENCE: 9

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Xaa Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Xaa Tyr Ala Cys Glu Val Thr His Gln Gly Leu Ser Ser
                 85                  90                  95
```

```
Pro Val Thr Lys Ser Phe Asn Arg Gly Glu Cys
            100                 105
```

<210> SEQ ID NO 10
<211> LENGTH: 107
<212> TYPE: PRT
<213> ORGANISM: Homo sapiens

<400> SEQUENCE: 10

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Val Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 11
<211> LENGTH: 107
<212> TYPE: PRT
<213> ORGANISM: Homo sapiens

<400> SEQUENCE: 11

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 12
<211> LENGTH: 107
<212> TYPE: PRT
<213> ORGANISM: Homo sapiens

<400> SEQUENCE: 12

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
            50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 326
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325
```